(12) United States Patent
Kim et al.

(10) Patent No.: US 9,419,230 B2
(45) Date of Patent: Aug. 16, 2016

(54) COMPOUND FOR ORGANIC OPTOELECTRONIC DEVICE, ORGANIC LIGHT EMITTING DIODE INCLUDING THE SAME, AND DISPLAY DEVICE INCLUDING THE ORGANIC LIGHT EMITTING DIODE

(71) Applicants: Hyung-Sun Kim, Uiwang-si (KR); Eun-Sun Yu, Uiwang-si (KR); Mi-Young Chae, Uiwang-si (KR)

(72) Inventors: Hyung-Sun Kim, Uiwang-si (KR); Eun-Sun Yu, Uiwang-si (KR); Mi-Young Chae, Uiwang-si (KR)

(73) Assignee: CHEIL INDUSTRIES, INC., Gumi-si, Kyeongsangbuk-do (KR)

(*) Notice: Subject to any disclaimer, the term of this patent is extended or adjusted under 35 U.S.C. 154(b) by 387 days.

(21) Appl. No.: 13/914,008

(22) Filed: Jun. 10, 2013

(65) Prior Publication Data
US 2013/0292659 A1 Nov. 7, 2013

Related U.S. Application Data

(63) Continuation of application No. PCT/KR2011/007539, filed on Oct. 11, 2011.

(30) Foreign Application Priority Data

Dec. 8, 2010 (KR) .......................... 10-2010-0124889

(51) Int. Cl.
*H01L 51/50* (2006.01)
*H01L 51/00* (2006.01)
(Continued)

(52) U.S. Cl.
CPC .......... *H01L 51/0072* (2013.01); *C07D 209/82* (2013.01); *C07D 209/88* (2013.01); *C07D 401/14* (2013.01); *C07D 403/14* (2013.01); *C07D 405/14* (2013.01); *C07D 409/14* (2013.01); *C07D 413/14* (2013.01); *C07D 471/04* (2013.01); *C09K 11/06* (2013.01); *H01L 51/0067* (2013.01); *H01L 51/0074* (2013.01); *H05B 33/10* (2013.01); *C09K 2211/1007* (2013.01); *C09K 2211/1011* (2013.01);
(Continued)

(58) Field of Classification Search
None
See application file for complete search history.

(56) References Cited

U.S. PATENT DOCUMENTS

2002/0045061 A1 4/2002 Hosokawa
2004/0110031 A1 6/2004 Fukuda et al.
(Continued)

FOREIGN PATENT DOCUMENTS

JP 2002-302516 A 10/2002
JP 2004-018787 A 1/2004
(Continued)

OTHER PUBLICATIONS

Promarak et al., Synthesis and properties of stable amorphous hole-transporting molecules for electroluminescent devices, 2006, Tetrahedron Letters, vol. 47, pp. 8949-8952.*
(Continued)

*Primary Examiner* — Gregory Clark
(74) *Attorney, Agent, or Firm* — Lee & Morse, P.C.

(57) ABSTRACT

A compound for an organic optoelectronic device, an organic light emitting diode including the same, and a display device including the organic light emitting diode are disclosed, and the compound for an organic optoelectronic device represented by Chemical Formula 1 is provided to manufacture an organic optoelectronic device having improved life-span characteristics due to excellent electrochemical and thermal stability, and high luminous efficiency at a low driving voltage.

18 Claims, 5 Drawing Sheets

(51) Int. Cl.

| | | |
|---|---|---|
| *C07D 209/82* | (2006.01) | |
| *C07D 209/88* | (2006.01) | |
| *C09K 11/06* | (2006.01) | |
| *H05B 33/10* | (2006.01) | |
| *C07D 401/14* | (2006.01) | |
| *C07D 405/14* | (2006.01) | |
| *C07D 413/14* | (2006.01) | |
| *C07D 403/14* | (2006.01) | |
| *C07D 409/14* | (2006.01) | |
| *C07D 471/04* | (2006.01) | |

(52) U.S. Cl.
CPC . *C09K2211/1029* (2013.01); *C09K 2211/1044* (2013.01); *C09K 2211/1059* (2013.01); *C09K 2211/1088* (2013.01); *H01L 51/0059* (2013.01); *H01L 51/0081* (2013.01); *H01L 51/0085* (2013.01); *H01L 51/5016* (2013.01)

(56) References Cited

U.S. PATENT DOCUMENTS

| | | | |
|---|---|---|---|
| 2004/0164292 A1* | 8/2004 | Tung | G02F 1/133603 257/40 |
| 2008/0269461 A1 | 10/2008 | Van Dijken et al. | |
| 2012/0280221 A1 | 11/2012 | Yu et al. | |

FOREIGN PATENT DOCUMENTS

| | | | | |
|---|---|---|---|---|
| JP | 2004-178895 | A | 6/2004 | |
| JP | 2009-021336 | A | 1/2009 | |
| JP | 2009-263579 | A | 11/2009 | |
| JP | 2009-267255 | * | 11/2009 | ............. H01L 51/50 |
| JP | 2009-267257 | A | 11/2009 | |
| KR | 10 2002-0026866 | A | 4/2002 | |
| KR | 10 2008-0092890 | A | 10/2008 | |
| KR | 10 2009-0028943 | A | 3/2009 | |
| KR | 10 2009-0051599 | A | 5/2009 | |
| WO | WO 2006/114377 | A1 | 11/2006 | |
| WO | WO 2009/060757 | A1 | 5/2009 | |
| WO | WO 2009/060780 | A1 | 5/2009 | |

OTHER PUBLICATIONS

Hyun, et al.; "Synthesis and electroluminescent properties of *para*- and *meta*-tolyl carbazyl derivatives;" Science Direct, Thin Solid Films; 2006; pp. 127-131; vol./Issue 209; Elsevier, USA.

Kim, et al.; "New host materials with high triplet energy level for blue-emitting electrophosphorescent device;" Science Direct, Synthetic Metals; 2007; pp. 743-750; vol./Issue 157; Elsevier; USA.

International Search Report in PCT/KR2011/007539, dated Jun. 8, 2012 (Kim, et al.).

* cited by examiner

COMPOUND FOR ORGANIC OPTOELECTRONIC DEVICE, ORGANIC LIGHT EMITTING DIODE INCLUDING THE SAME, AND DISPLAY DEVICE INCLUDING THE ORGANIC LIGHT EMITTING DIODE

CROSS-REFERENCE TO RELATED APPLICATIONS

This application is a continuation of pending International Application No. PCT/KR2011/007539, entitled "Compound for Organic Optoelectronic Device, Organic Light Emitting Diode Including the Same, and Display Device Including the Organic Light Emitting Diode," which was filed on Oct. 11, 2011, the entire contents of which are hereby incorporated by reference.

The present application claims priority under 35 U.S.C. §119 to Korean Patent Application No. 10-2010-0124889, filed on Dec. 8, 2010, in the Korean Intellectual Property Office, and entitled: "Compound for Organic Optoelectronic Device, Organic Light Emitting Diode Including the Same, and Display Device Including the Organic Light Emitting Diode," which is incorporated by reference herein in its entirety.

BACKGROUND

1. Field

Embodiments relate to a compound for an organic optoelectronic device, an organic light emitting diode including the same, and a display device including the organic light emitting diode.

2. Description of the Related Art

An organic photoelectric device may use a charge exchange between an electrode and an organic material by using holes or electrons. An organic optoelectronic device may be classified in accordance with its driving principles. A first organic optoelectronic device is an electronic device driven as follows: excitons are generated in an organic material layer by photons from an external light source; the excitons are separated into electrons and holes; and the electrons and holes are transferred to different electrodes as a current source (voltage source).

A second organic optoelectronic device is an electronic device driven as follows: a voltage or a current is applied to at least two electrodes to inject holes and/or electrons into an organic material semiconductor positioned at an interface of the electrodes, and the device is driven by the injected electrons and holes.

Examples of the organic optoelectronic device includes an organic photoelectronic device, an organic light emitting diode, an organic solar cell, an organic photoconductor drum, an organic transistor, and the like, which use a hole injecting or transport material, an electron injecting or transport material, or a light emitting material.

For example, an organic light emitting diode (OLED) has recently drawn attention due to an increasing demand for flat panel displays. In general, organic light emission refers to conversion of electrical energy into photo-energy.

SUMMARY

Embodiments are directed to a compound for an organic optoelectronic device represented by the following Chemical Formula 1,

[Chemical Formula 1]

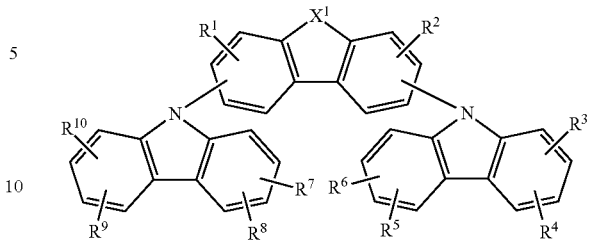

In the above Chemical Formula 1, $X^1$ may be —NR'—, —O—, —Se—, —PR'— or —S—, the R' may be hydrogen; deuterium; a substituted or unsubstituted C1 to C20 alkyl group; a substituted or unsubstituted C6 to C30 aryl group; or a substituted or unsubstituted C2 to C30 heteroaryl group having electron characteristics; $R^1$ to $R^{10}$ may be the same or different and may independently be hydrogen; deuterium; a substituted or unsubstituted C1 to C20 alkyl group; a substituted or unsubstituted C6 to C30 aryl group; or a substituted or unsubstituted C2 to C30 heteroaryl group having electron characteristics; and at least one of the $R^1$ to $R^{10}$ or R' may be a substituted or unsubstituted C6 to C30 aryl group having electron characteristics; or a substituted or unsubstituted C2 to C30 heteroaryl group having electron characteristics.

Embodiments are also directed to a compound for an organic optoelectronic device represented by the following Chemical Formula 2,

[Chemical Formula 2]

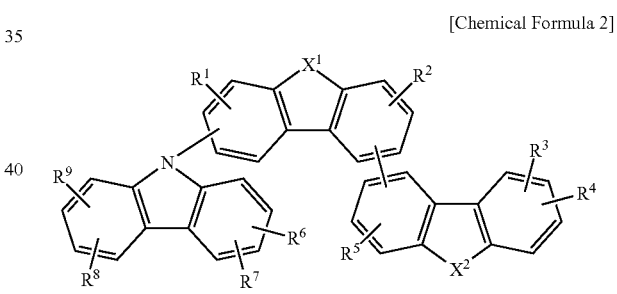

In the above Chemical Formula 2, $X^1$ may be —NR'—, —O—, —Se—, —PR'— or —S—, $X^2$ may be —NR"—, —O—, —Se—, —PR"— or —S—, wherein the R' and R" may be the same or different and may independently be hydrogen; deuterium; a substituted or unsubstituted C1 to C20 alkyl group; a substituted or unsubstituted C6 to C30 aryl group; or a substituted or unsubstituted C2 to C30 heteroaryl group having electron characteristics; $R^1$ to $R^9$ may be the same or different and may independently be hydrogen; deuterium; a substituted or unsubstituted C1 to C20 alkyl group; a substituted or unsubstituted C6 to C30 aryl group; or a substituted or unsubstituted C2 to C30 heteroaryl group having electron characteristics; and at least one of the $R^1$ to $R^9$, R' or R" may be a substituted or unsubstituted C6 to C30 aryl group having electron characteristics; or a substituted or unsubstituted C2 to C30 heteroaryl group having electron characteristics.

Embodiments are also directed to a compound for an organic optoelectronic device represented by the following Chemical Formula 3,

[Chemical Formula 3]

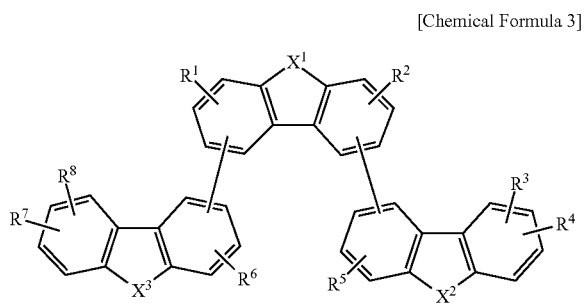

In the above Chemical Formula 3, $X^1$ may be —NR'—, —O—, —Se—, —PR'— or —S—, $X^2$ may be —NR''—, —O—, —Se—, —PR''— or —S—, $X^3$ may be —NR'''—, —O—, —Se—, —PR'''— or —S—, the R' to R''' may be the same or different and may independently be hydrogen; deuterium; a substituted or unsubstituted C1 to C20 alkyl group; a substituted or unsubstituted C6 to C30 aryl group; or a substituted or unsubstituted C2 to C30 heteroaryl group having electron characteristics; $R^1$ to $R^8$ may be the same or different and may independently be hydrogen; deuterium; a substituted or unsubstituted C1 to C20 alkyl group; a substituted or unsubstituted C6 to C30 aryl group; or a substituted or unsubstituted C2 to C30 heteroaryl group having electron characteristics; and at least one of the $R^1$ to $R^8$ or R' to R''' may be a substituted or unsubstituted C6 to C30 aryl group having electron characteristics; or a substituted or unsubstituted C2 to C30 heteroaryl group having electron characteristics.

Embodiments are also directed to a compound for an organic optoelectronic device represented by the following Chemical Formula 4,

[Chemical Formula 4]

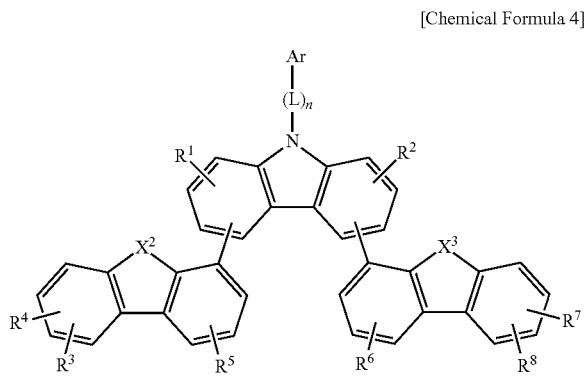

In the above Chemical Formula 4, $X^2$ and $X^3$ may be the same or different and may independently be —NR'—, —O—, —Se—, —PR'— or —S—, the R' may be hydrogen; deuterium; a substituted or unsubstituted C1 to C20 alkyl group; a substituted or unsubstituted C6 to C30 aryl group; or a substituted or unsubstituted C2 to C30 heteroaryl group having electron characteristics; $R^1$ to $R^8$ may be the same or different and may independently be hydrogen; deuterium; a substituted or unsubstituted C1 to C20 alkyl group; a substituted or unsubstituted C6 to C30 aryl group; or a substituted or unsubstituted C2 to C30 heteroaryl group having electron characteristics; L may be a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C2 to C30 heteroarylene group, or a combination thereof, n may be an integer ranging from 1 to 2, and Ar may be a substituted or unsubstituted C6 to C30 aryl group having electron characteristics; or a substituted or unsubstituted C2 to C30 heteroaryl group having electron characteristics.

Embodiments are also directed to a compound for an organic optoelectronic device represented by one of Chemical Formulae 1a to 33a.

Embodiments are also directed to a compound for an organic optoelectronic device represented by one of Chemical Formulae 1b to 33b.

Embodiments are also directed to a compound for an organic optoelectronic device represented by one of Chemical Formulae 1c to 37c.

Embodiments are also directed to a compound for an organic optoelectronic device represented by one of Chemical Formulae 1d to 33d.

Embodiments are also directed to an organic light emitting diode including an anode, a cathode, and at least one organic thin layer between the anode and the cathode. At least one organic thin layer includes the compound for an organic optoelectronic device described above.

Embodiments are also directed to a display device including the organic light emitting diode.

BRIEF DESCRIPTION OF THE DRAWINGS

Features will become apparent to those of skill in the art by describing in detail example embodiments with reference to the attached drawings in which.

DETAILED DESCRIPTION

Figure 1:
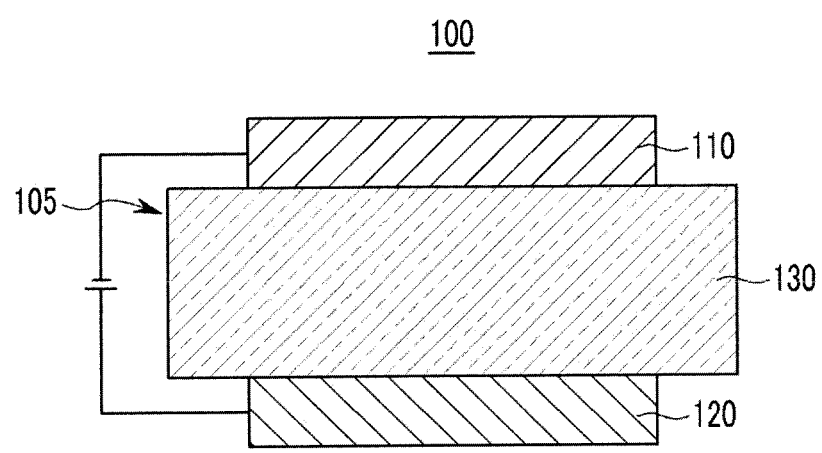
FIGS. 1 to 5 are cross-sectional views showing organic light emitting diodes according to various embodiments, including a compound for an organic optoelectronic device according to an example embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art. In the drawing figures, the dimensions of layers and regions may be exaggerated for clarity of illustration. Like reference numerals refer to like elements throughout.

In the present specification, when a definition is not otherwise provided, "substituted" refers to one substituted with a C1 to C30 alkyl group; a C1 to C10 alkylsilyl group; a C3 to C30 cycloalkyl group; a C6 to C30 aryl group; a C2 to C30 heteroaryl group; a C1 to C10 alkoxy group; a fluoro group, a C1 to C10 trifluoroalkyl group such as a trifluoromethyl group, and the like; or a cyano group.

In the present specification, when a definition is not otherwise provided, "hetero" refers to one including 1 to 3 heteroatoms selected from the group of N, O, S, and P, and remaining carbons in one functional group.

In the specification, when a definition is not otherwise provided, "alkyl group" may refer to "a saturated group" without any alkene group or alkyne group; or "an unsaturated alkyl group" with at least one alkene group or alkyne group. The "alkene group" may refer to a substituent of at least one carbon-carbon double bond of at least two carbons, and the "alkyne group" may refer to a substituent of at least one carbon-carbon triple bond of at least two carbons. The alkyl group may be branched, linear, or cyclic.

The alkyl group may be a C1 to C20 alkyl group, and specifically a C1 to C6 lower alkyl group, a C7 to C10 medium-sized alkyl group, or a C11 to C20 higher alkyl group.

For example, a C1 to C4 alkyl group may have 1 to 4 carbon atoms and may be selected from the group of methyl, ethyl, propyl, iso-propyl, n-butyl, iso-butyl, sec-butyl, and t-butyl.

Typical examples of alkyl group may be a methyl group, an ethyl group, a propyl group, an isopropyl group, a butyl group, an isobutyl group, a t-butyl group, a pentyl group, a hexyl group, an ethenyl group, a propenyl group, a butenyl group, a cyclopropyl group, a cyclobutyl group, a cyclopentyl group, a cyclohexyl group, and the like.

"Aromatic group" may refer to a substituent including all element of the cycle having p-orbitals which form conjugation. Examples may include an aryl group and a heteroaryl group.

"Aryl group" may refer to a monocyclic or fused ring polycyclic (i.e., rings sharing adjacent pairs of carbon atoms) substituent.

"Heteroaryl group" may refer to an aryl group including 1 to 3 heteroatoms selected from the group of N, O, S, and P, and remaining carbons in one functional group. The aryl group may be a fused ring cyclic group where each cycle may include the 1 to 3 heteroatoms.

The number of atoms in the aryl group and heteroaryl group is a sum of a carbon atom number and a non-carbon atom number.

A compound for an organic optoelectronic device according to an example embodiment has a structure including a core moiety including three carbazoles or carbazole-based derivatives bonded to each other and selective substituents bonded with the core moiety.

In the present specification, the carbazole-based derivative may be a structure where a nitrogen of a substituted or unsubstituted carbazole or carbazolyl group is a heteroatom except nitrogen.

At least one of the substituents bonded to the core moiety may be a substituent having improved electron characteristics.

Accordingly, the compound may satisfy requirements of an emission layer by complementing improved hole characteristics of its carbazole structure with electron characteristics. For example, the compound may be used as a host material for an emission layer.

In this specification, hole characteristics refer to characteristics that holes formed in the anode is easily injected into the emission layer and transported in the emission layer due to conductive characteristic according to HOMO level.

In this specification, electron characteristics refer to characteristics that electrons formed in the cathode is easily injected into the emission layer and transported in the emission layer due to conductive characteristics according to LUMO level.

The compound for an organic optoelectronic device includes a core moiety and various substituents for substituting the core moiety and thus may have various energy bandgaps. Accordingly, the compound may be used in an electron injection layer (EIL) and transport layer or a hole injection layer (HIL) and transport layer.

The compound may have an appropriate energy level depending on the substituents and thus may fortify electron transport capability of an organic photoelectric device and bring about excellent effects on efficiency and driving voltage and also, may provide excellent electrochemical and thermal stability and thus improve a life-span characteristic during the operation of the organic photoelectric device.

According to an example embodiment, a compound for an organic optoelectronic device represented by the following Chemical Formula 1 is provided.

[Chemical Formula 1]

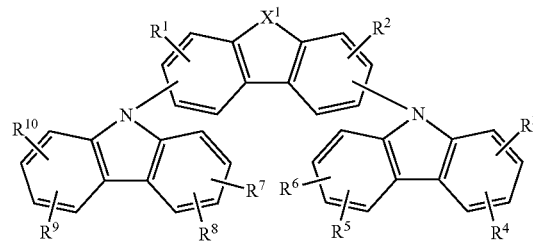

In the above Chemical Formula 1, $X^1$ may be —NR'—, —O—, —Se—, —PR'— or —S—, wherein the R' may be hydrogen; deuterium; a substituted or unsubstituted C1 to C20 alkyl group; a substituted or unsubstituted C6 to C30 aryl group; or a substituted or unsubstituted C2 to C30 heteroaryl group having electron characteristics; $R^1$ to $R^{10}$ may be the same or different and may independently be hydrogen; deuterium; a substituted or unsubstituted C1 to C20 alkyl group; a substituted or unsubstituted C6 to C30 aryl group; or a substituted or unsubstituted C2 to C30 heteroaryl group having electron characteristics; at least one of the $R^1$ to $R^{10}$ or R' may be a substituted or unsubstituted C6 to C30 aryl group having electron characteristics; or a substituted or unsubstituted C2 to C30 heteroaryl group having electron characteristics.

The compound represented by the above Chemical Formula 1 may include carbazole or carbazole-based derivative having excellent bipolar characteristics as a core.

A substituent having a pi-bond of the $R^1$ to $R^{10}$ and R' increases a triplet energy bandgap by controlling the total π-conjugation length of a compound, and may thus be useful for an emission layer of organic optoelectronic device (e.g., organic light emitting diode) as phosphorescent host.

In addition, an appropriate combination of the substituents may provide a compound having excellent thermal stability or resistance against oxidation.

An appropriate combination of the substituents may provide a compound having an asymmetric bipolar characteristic. The asymmetric bipolar characteristic may improve hole and electron transport capability and thus luminous efficiency and performance of a device.

In addition, the substituents may be adjusted to make the structure of a compound bulky and thus decrease crystallinity of the compound. Accordingly, the compound having low crystallinity may improve a life-span of a device.

As described above, one of the substituents of the compound may be a substituted or unsubstituted C6 to C30 aryl group having electron characteristics; or a substituted or unsubstituted C2 to C30 heteroaryl group having electron characteristics.

The substituted or unsubstituted C6 to C30 aryl group having electron characteristics may be a substituted or unsubstituted triperylenyl group, a substituted or unsubstituted fluorenyl group, a substituted or unsubstituted spirofluorenyl group, a substituted or unsubstituted terphenyl group, a substituted or unsubstituted pyrenyl group, a substituted or unsubstituted perylenyl group, a substituted or unsubstituted phenanthrenyl group or a combination thereof.

Specific examples of the substituted or unsubstituted C2 to C30 heteroaryl group having electron characteristics may be a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof.

The $X^1$ may be —NR'—, wherein the R' may be a substituted or unsubstituted C6 to C30 aryl group having electron characteristics; or a substituted or unsubstituted C2 to C30 heteroaryl group having electron characteristics. Thus, as a core, the carbazole-based derivative may be carbazole, which provide more effective hole characteristics.

In another example embodiment, a compound for an organic optoelectronic device represented by the following Chemical Formula 2 is provided.

[Chemical Formula 2]

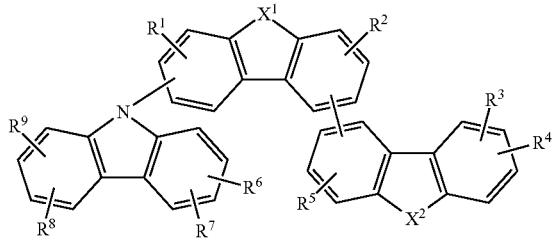

In the above Chemical Formula 2, $X^1$ may be —NR'—, —O—, —Se—, —PR'— or —S—, $X^2$ may be —NR"—, —O—, —Se—, —PR"— or —S—, the R' and R" may be the same or different and may independently be hydrogen; deuterium; a substituted or unsubstituted C1 to C20 alkyl group; a substituted or unsubstituted C6 to C30 aryl group; or a substituted or unsubstituted C2 to C30 heteroaryl group having electron characteristics; $R^1$ to $R^9$ may be the same or different and may independently be hydrogen; deuterium; a substituted or unsubstituted C1 to C20 alkyl group; a substituted or unsubstituted C6 to C30 aryl group; or a substituted or unsubstituted C2 to C30 heteroaryl group having electron characteristics; and at least one of the $R^1$ to $R^9$, R' or R" may be a substituted or unsubstituted C6 to C30 aryl group having electron characteristics; or a substituted or unsubstituted C2 to C30 heteroaryl group having electron characteristics.

The above Chemical Formula 2 has a structure where a binding position of one carbazole in the above Chemical Formula 1 is changed into carbon-carbon. Such a structure may maintain appropriate energy band of a bicarbazole, and additional substituents having electron transfer/transport characteristics may be introduced.

The substituent having electron characteristics is the same as in the above Chemical Formula 1 and thus descriptions thereof are not repeated.

In another example embodiment, a compound for an organic optoelectronic device represented by the following Chemical Formula 3 is provided.

[Chemical Formula 3]

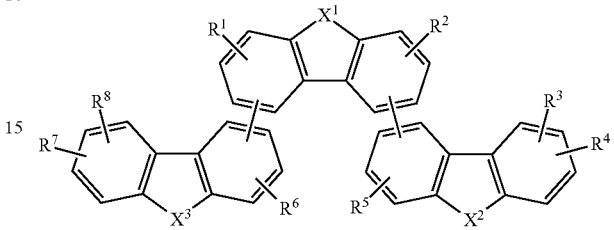

In the above Chemical Formula 3, $X^1$ may be —NR'—, —O—, —Se—, —PR'— or —S—, $X^2$ may be —NR"—, —O—, —Se—, —PR"— or —S—, $X^3$ may be —NR'"—, —O—, —Se—, —PR'"— or —S—, the R' to R'" may be the same or different and may independently be hydrogen; deuterium; a substituted or unsubstituted C1 to C20 alkyl group; a substituted or unsubstituted C6 to C30 aryl group; or a substituted or unsubstituted C2 to C30 heteroaryl group having electron characteristics; $R^1$ to $R^8$ may be the same or different and may independently be hydrogen; deuterium; a substituted or unsubstituted C1 to C20 alkyl group; a substituted or unsubstituted C6 to C30 aryl group; or a substituted or unsubstituted C2 to C30 heteroaryl group having electron characteristics; and at least one of the R' to $R^8$ or R' to R'" may be a substituted or unsubstituted C6 to C30 aryl group having electron characteristics; or a substituted or unsubstituted C2 to C30 heteroaryl group having electron characteristics.

The above Chemical Formula 3 has a structure where carbazole-based derivatives in the above Chemical Formula 1 have carbon-carbon bonds. When all carbazole-based derivatives of a core have carbon-carbon bonds, a substituent having electron transfer/transport characteristics may be introduced while minimizing changes of conjugation lengths of a whole compound that may cause changes of an energy band.

The substituent having electron characteristics is the same as described in the above Chemical Formula 1 and thus descriptions thereof are not repeated.

The $X^1$ may be —NR'—, the $X^2$ may be —NR"—, and the $X^3$ may be —NR'"—. Thus, all carbazole-based derivatives of the above Chemical Formula 3 may be carbazole. As shown above, a three-carbazole bonded structure may be present in a core, and more effective hole characteristics and bipolar characteristics may be obtained.

At least one of the R' to R'" may be a substituted or unsubstituted C6 to C30 aryl group having electron characteristics; or a substituted or unsubstituted C2 to C30 heteroaryl group having electron characteristics. Thus, in the three-carbazole bonded structure as a core, a substituent having electron characteristics may be bonded to at least one of each nitrogen.

When the substituent having electron characteristics is bonded at a nitrogen position of carbazole, bipolar characteristics of a material may be improved due to a substituent having electron transfer/transport characteristics while minimizing changes of conjugation lengths that may cause changes of an energy band.

In another example embodiment, a compound for an organic optoelectronic device represented by the following Chemical Formula 4 is provided.

[Chemical Formula 4]

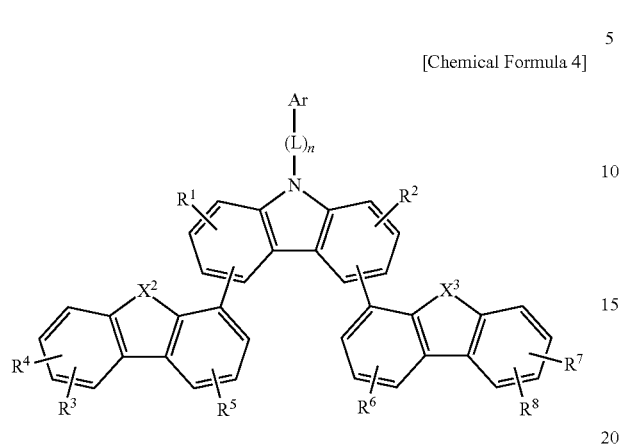

In the above Chemical Formula 4, $X^2$ and $X^3$ may be the same or different and may independently be —NR'—, —O—, —Se—, —PR'— or —S—, the R' may hydrogen; deuterium; a substituted or unsubstituted C1 to C20 alkyl group; a substituted or unsubstituted C6 to C30 aryl group; or a substituted or unsubstituted C2 to C30 heteroaryl group having electron characteristics; $R^1$ to $R^8$ may be the same or different and may independently be hydrogen; deuterium; a substituted or unsubstituted C1 to C20 alkyl group; a substituted or unsubstituted C6 to C30 aryl group; or a substituted or unsubstituted C2 to C30 heteroaryl group having electron characteristics; L may a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C2 to C30 heteroarylene group, or a combination thereof, n may an integer ranging from 1 to 2, and Ar may a substituted or unsubstituted C6 to C30 aryl group having electron characteristics; or a substituted or unsubstituted C2 to C30 heteroaryl group having electron characteristics.

The above Chemical Formula 4 has a structure where binding positions (e.g., 4-positions of dibenzofuran and dibenzothiophene) of both derivatives bonded to carbazole of a core are specified. The binding structure may have a spatially distorted structure and coplanarity. As a conjugation length is shorter, a HOMO/LUMO energy bandgap and a gap of triplet excitation energy are higher. As a phosphorescent red is shifted to green and blue, an energy gap of a dopant increases and accordingly an energy bandgap of a host material should increase device which are favorable for improvement of luminous efficiency and life-span.

The $X^2$ and $X^3$ may be the same. In case of such a structure, there may be advantages of easy synthesis and a high purity material.

Ar may a substituted or unsubstituted C6 to C30 aryl group having electron characteristics; or a substituted or unsubstituted C2 to C30 heteroaryl group having electron characteristics, and may the same as in the above described embodiment and thus descriptions thereof are not repeated.

L may a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C2 to C30 heteroarylene group, or a combination thereof.

The compound for an organic optoelectronic device may be a compound represented by, e.g., one of the following Chemical Formulae 1a to 33a.

[Chemical Formula 1a]

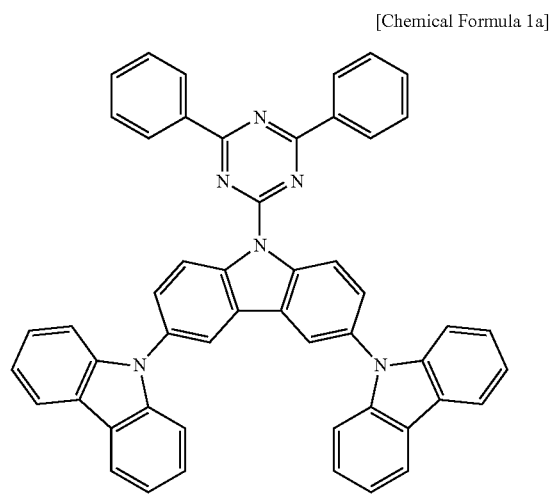

[Chemical Formula 2a]

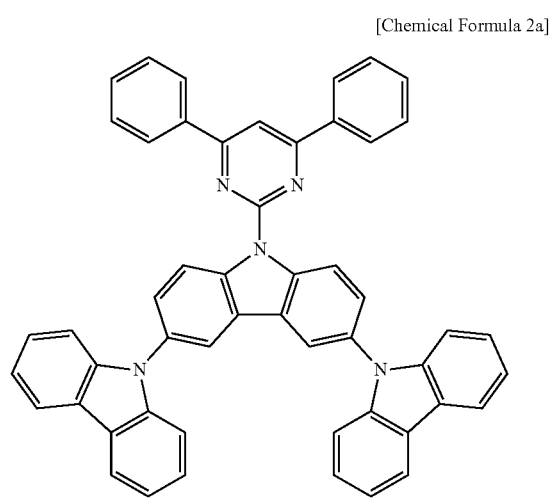

[Chemical Formula 3a]

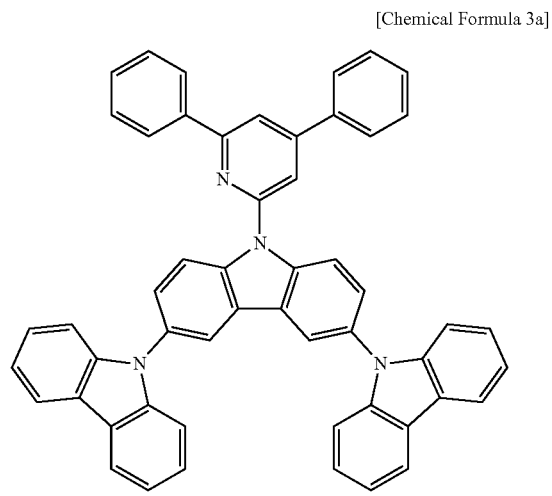

[Chemical Formula 4a]
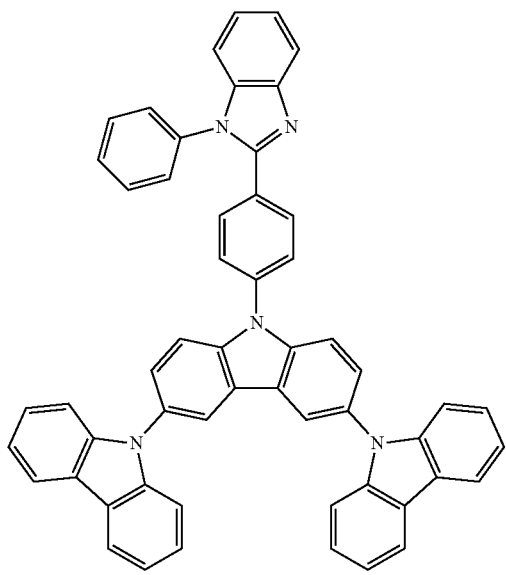
[Chemical Formula 5a]
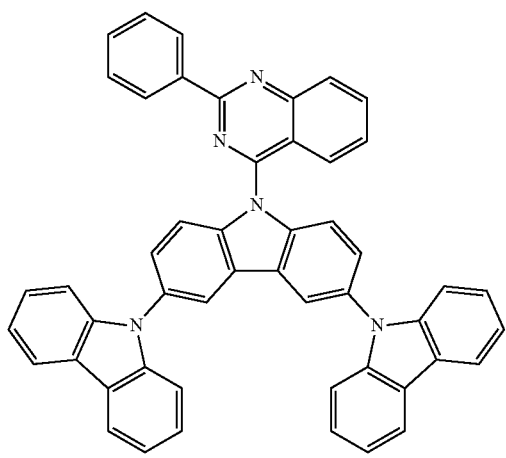
[Chemical Formula 6a]
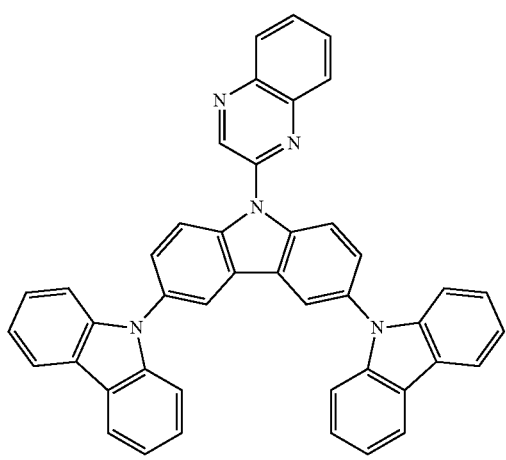
[Chemical Formula 7a]
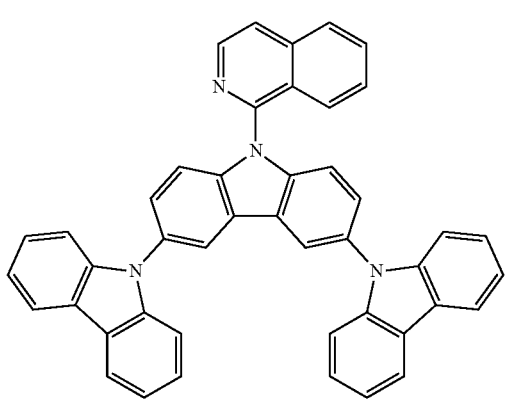
[Chemical Formula 8a]
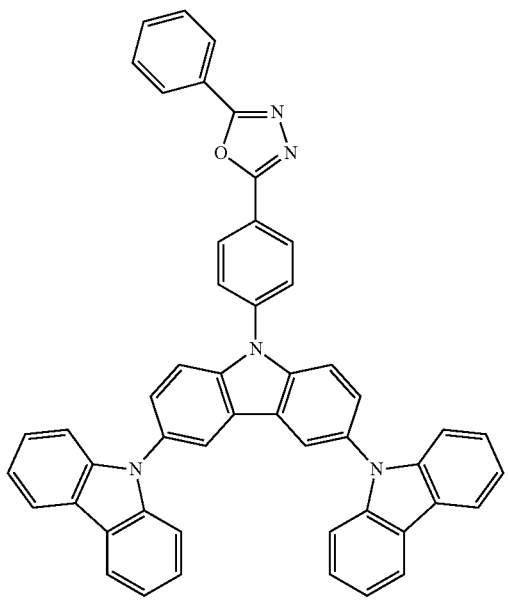
[Chemical Formula 9a]
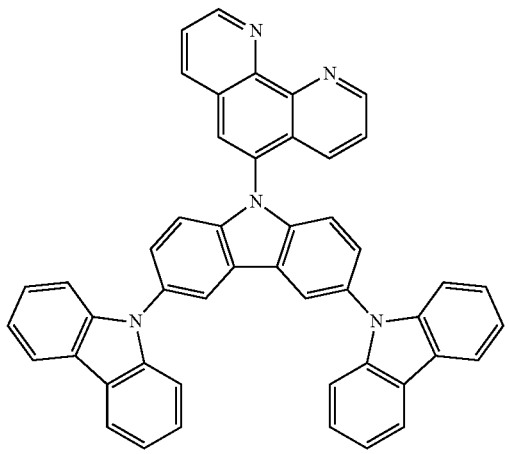

[Chemical Formula 10a]
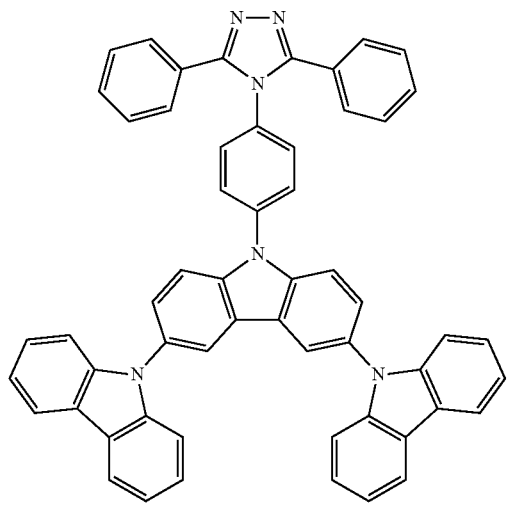
[Chemical Formula 11a]
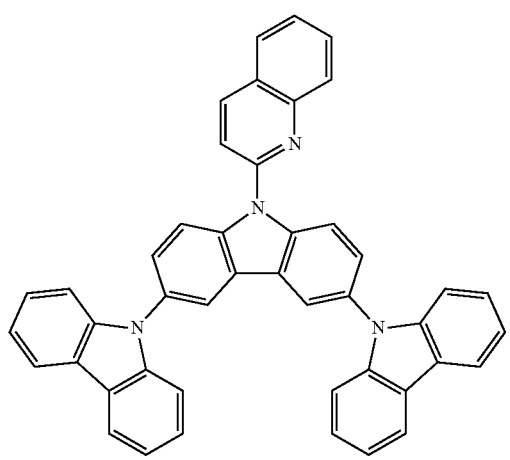
[Chemical Formula 12a]
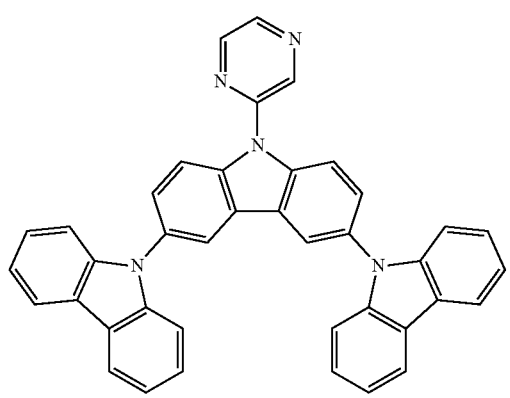
[Chemical Formula 13a]
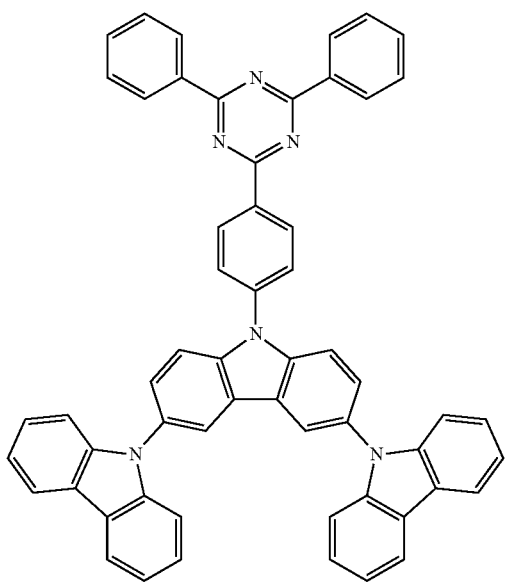
[Chemical Formula 14a]
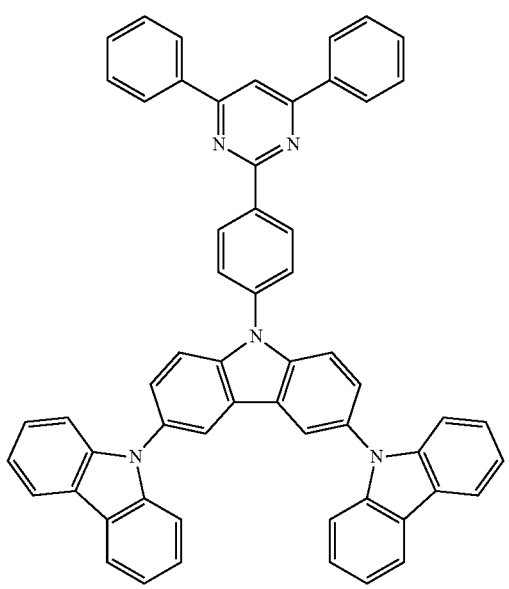

[Chemical Formula 15a]
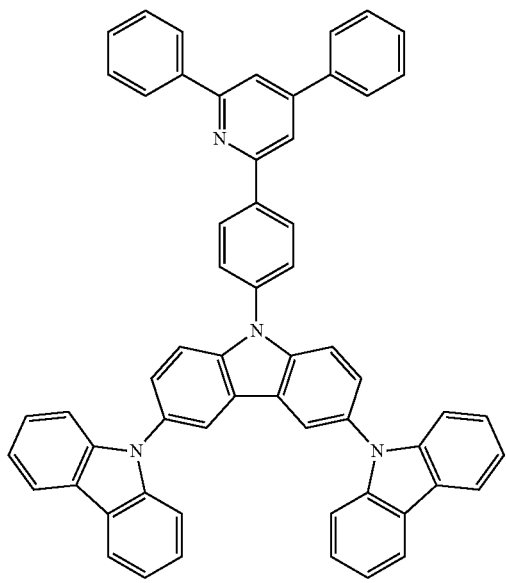
[Chemical Formula 16a]
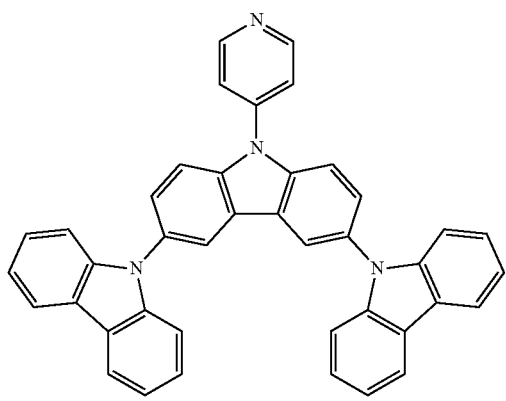
[Chemical Formula 17a]
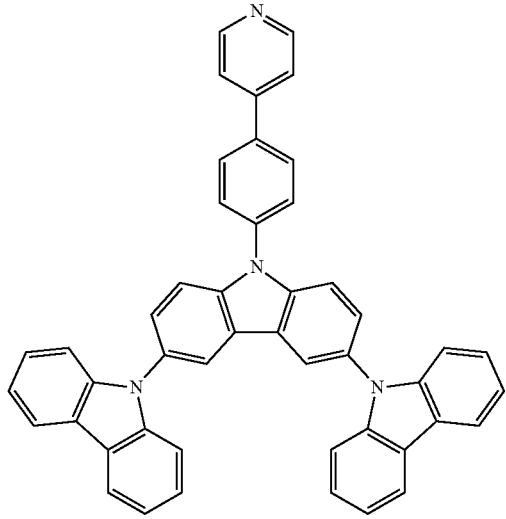
[Chemical Formula 18a]
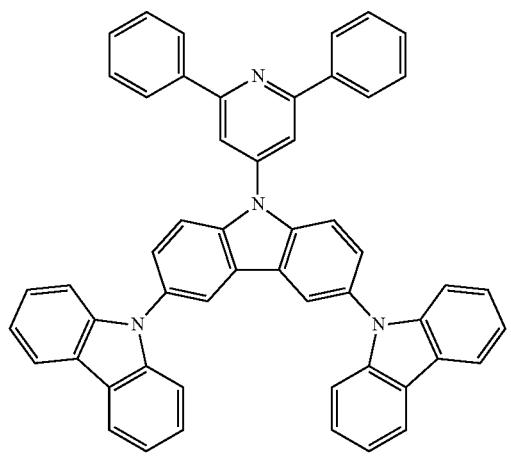
[Chemical Formula 19a]
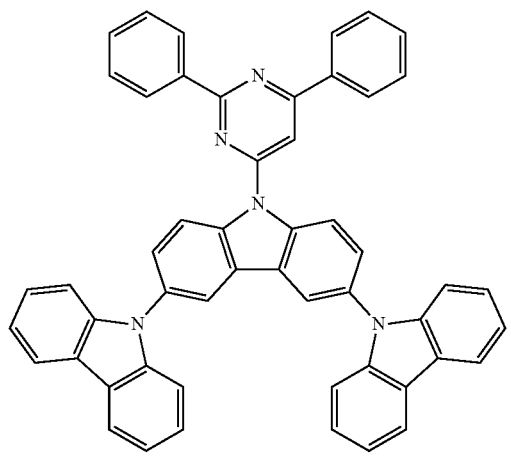
[Chemical Formula 20a]
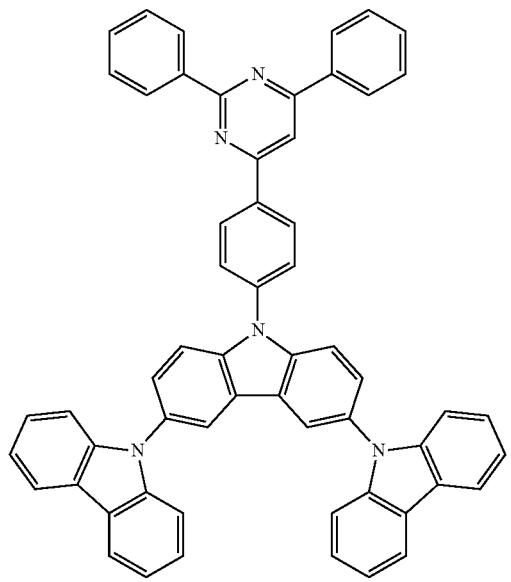

[Chemical Formula 21a]
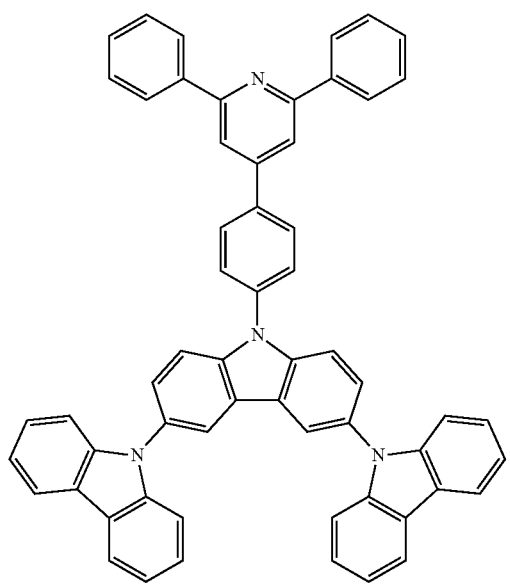
[Chemical Formula 22a]
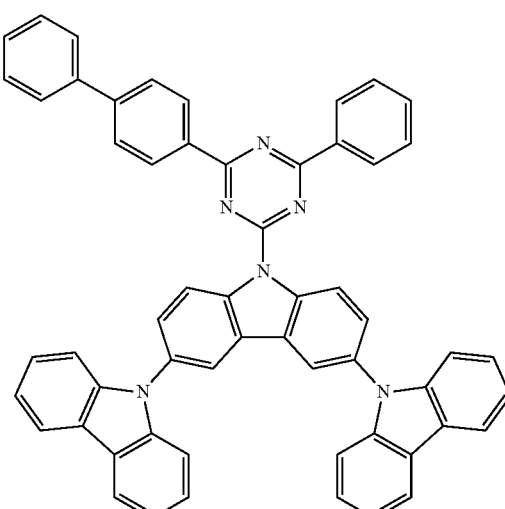
[Chemical Formula 23a]
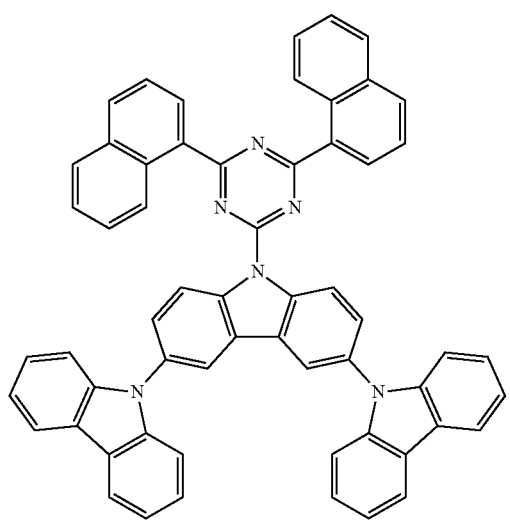
[Chemical Formula 24a]
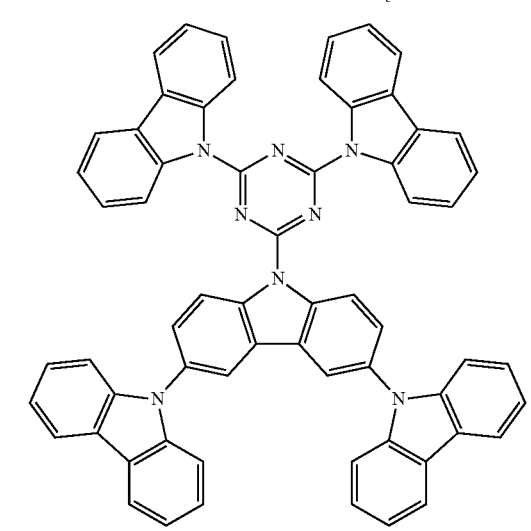
[Chemical Formula 25a]
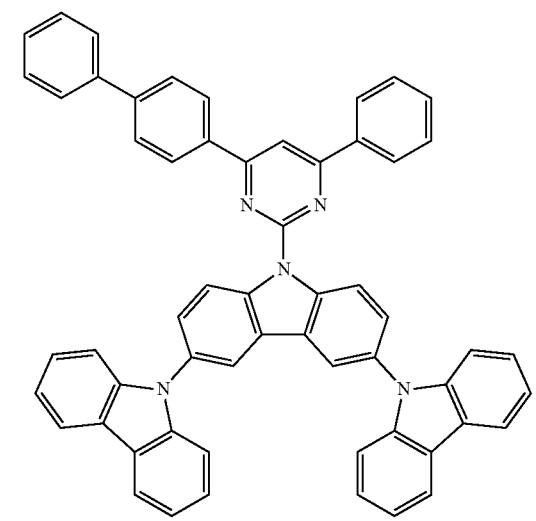
[Chemical Formula 26a]
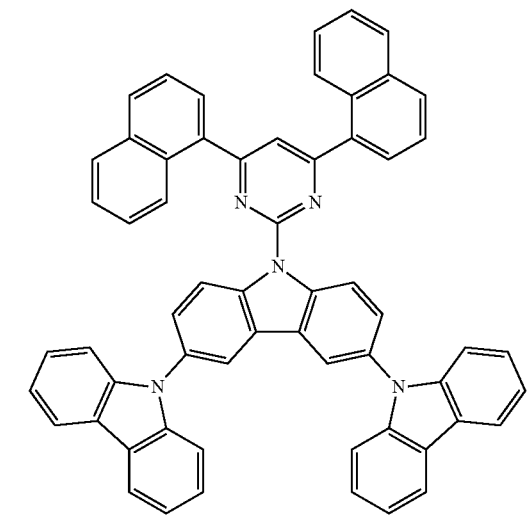

[Chemical Formula 27a]
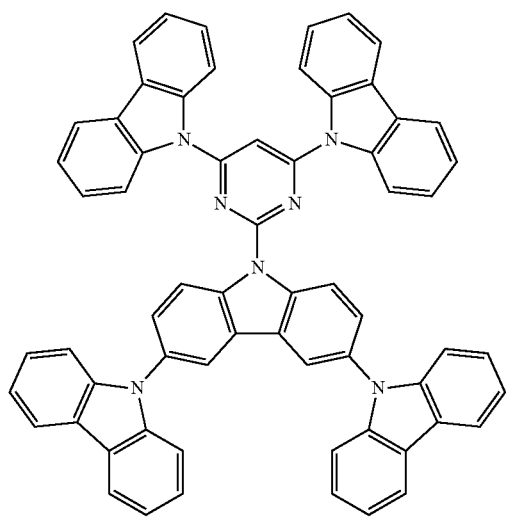
[Chemical Formula 28a]
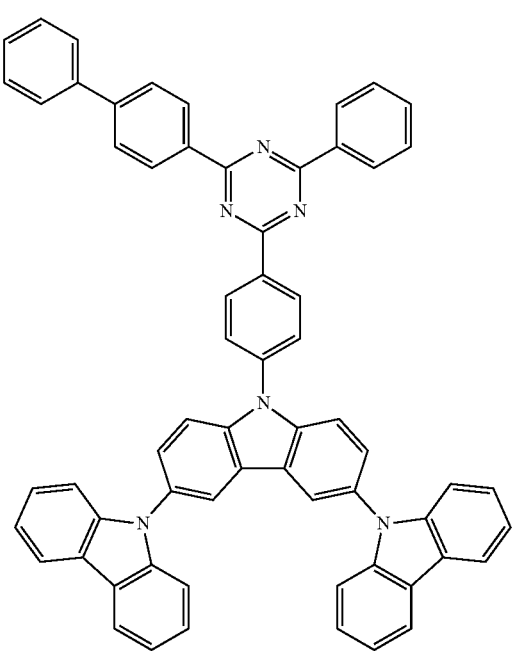
[Chemical Formula 29a]
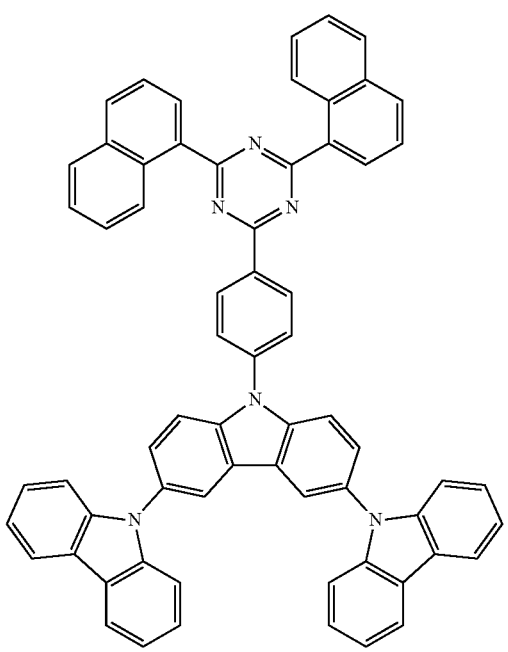
[Chemical Formula 30a]
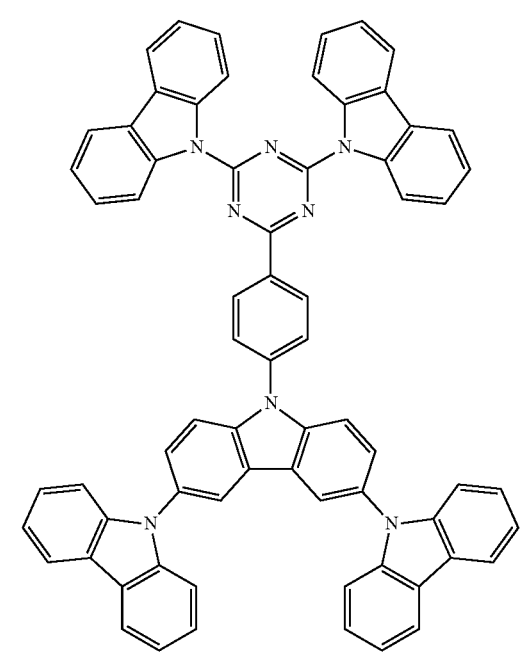

[Chemical Formula 31a]
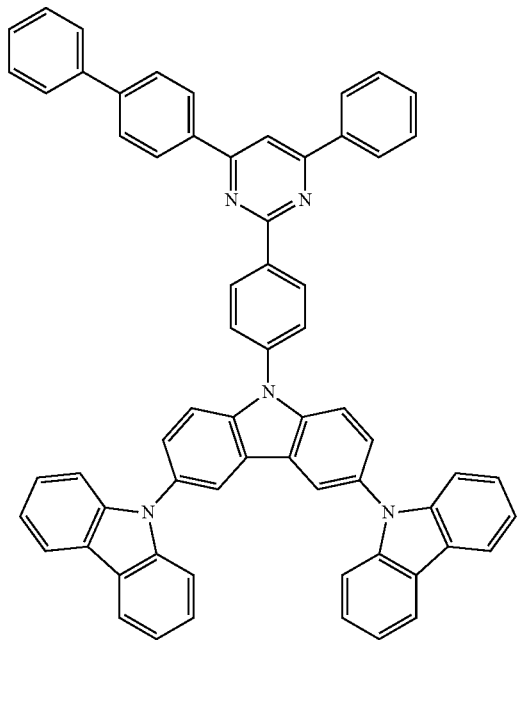
[Chemical Formula 32a]
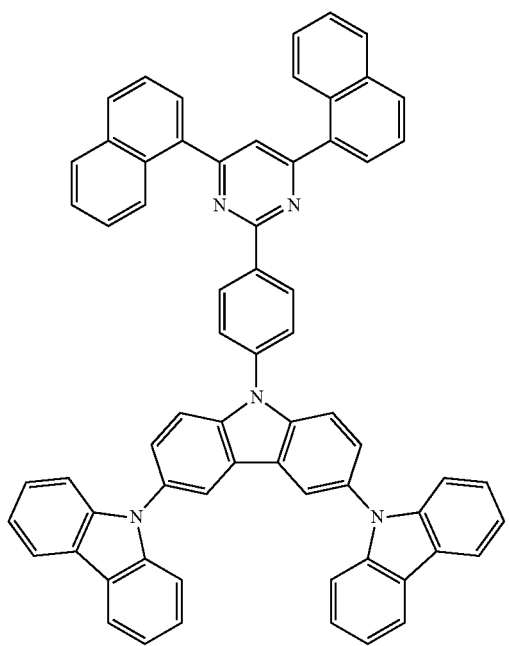
[Chemical Formula 33a]
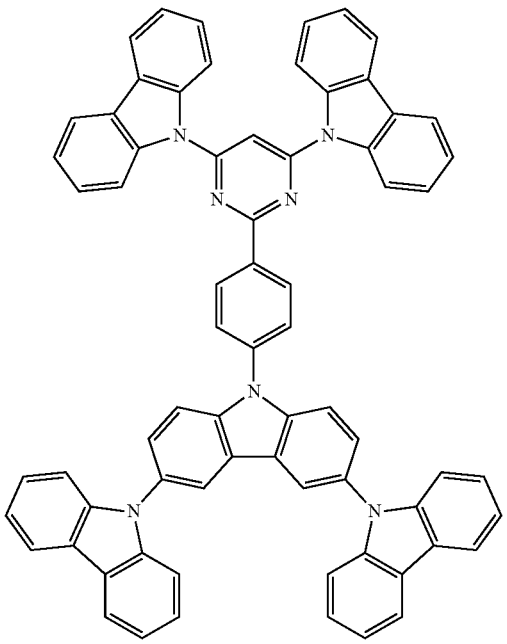
The compound for an organic optoelectronic device may be a compound represented by, e.g., one of the following Chemical Formulae 1b to 33b.
[Chemical Formula 1b]
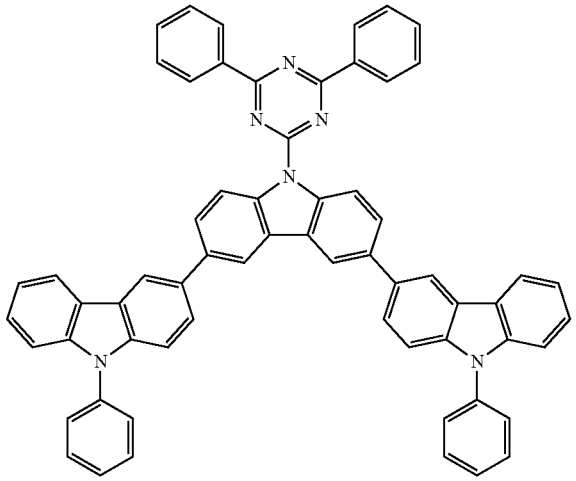

[Chemical Formula 2b]
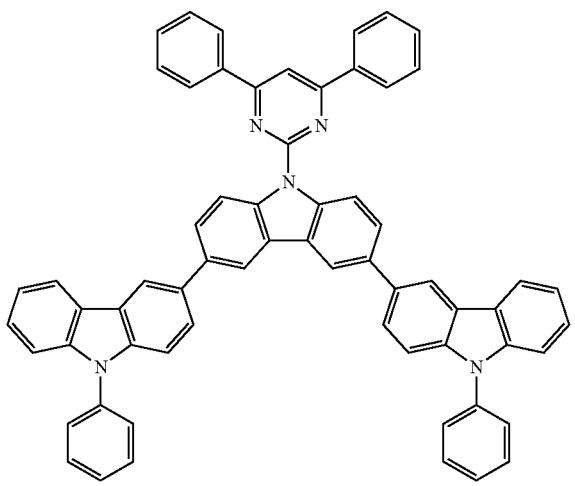
[Chemical Formula 3b]
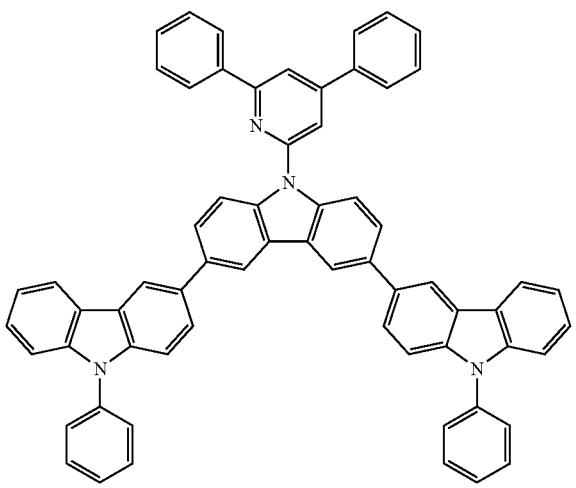
[Chemical Formula 4b]
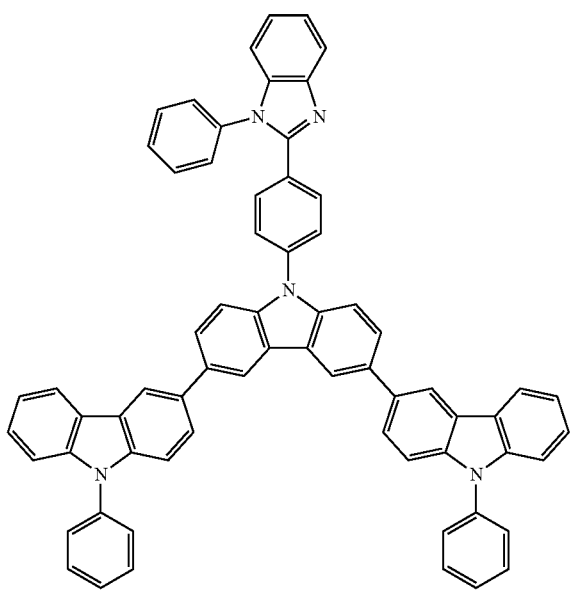
[Chemical Formula 5b]
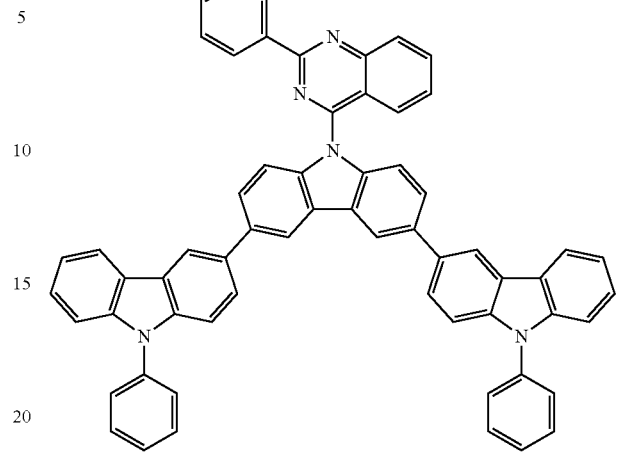
[Chemical Formula 6b]
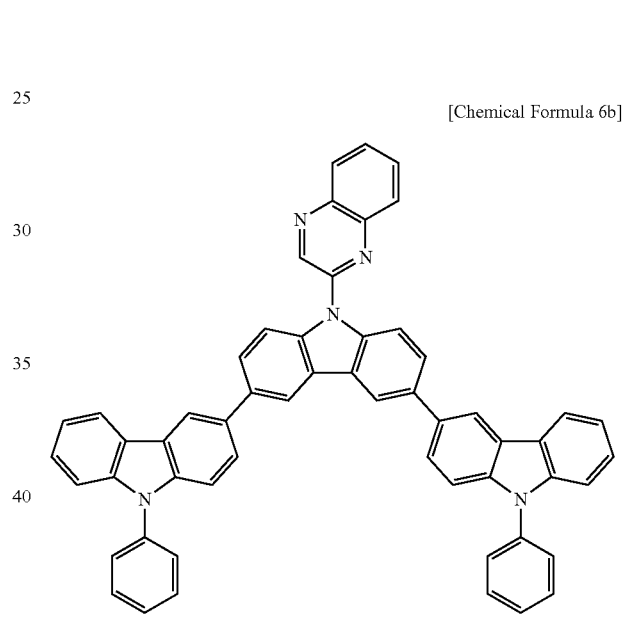
[Chemical Formula 7b]
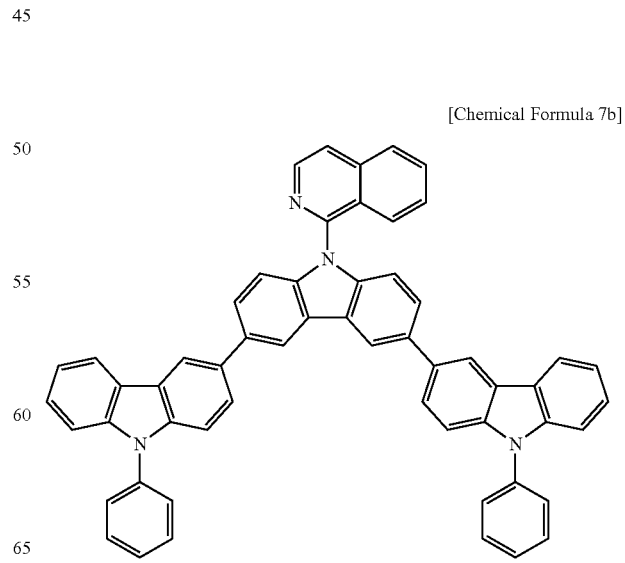

[Chemical Formula 8b]
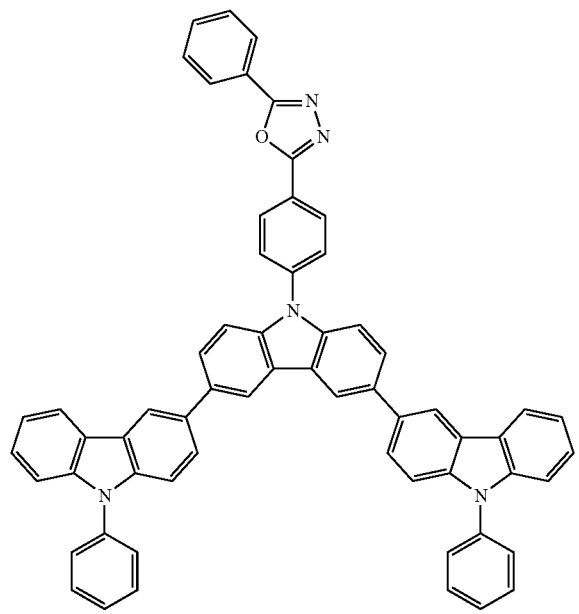
[Chemical Formula 9b]
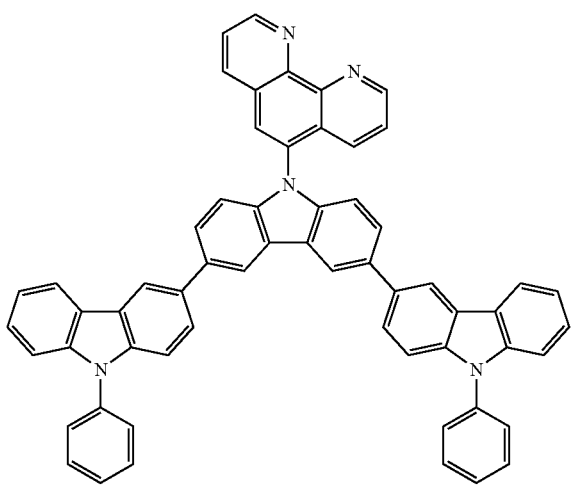
[Chemical Formula 10b]
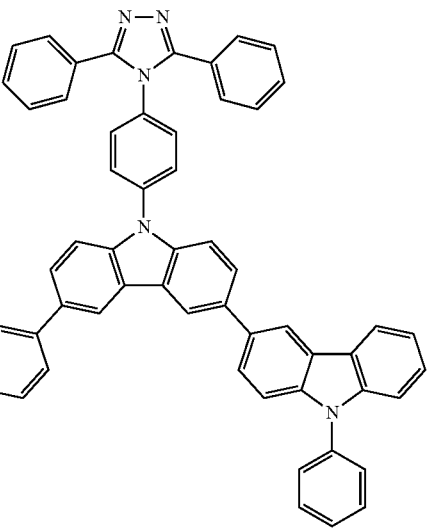
[Chemical Formula 11b]
[Chemical Formula 12b]

[Chemical Formula 13b]
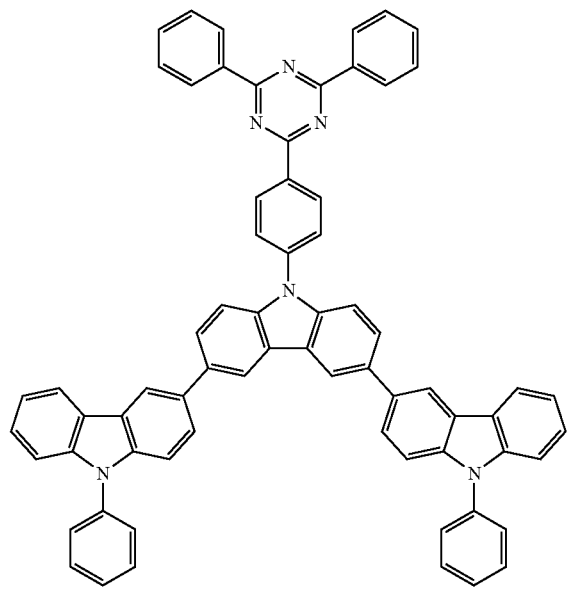
[Chemical Formula 14b]
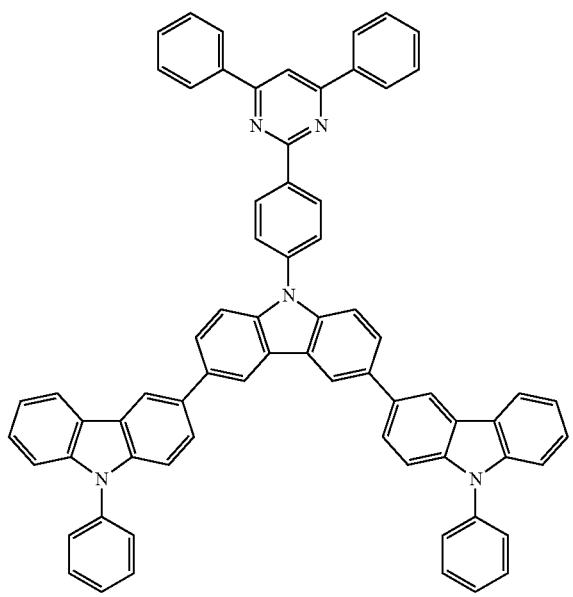
[Chemical Formula 15b]
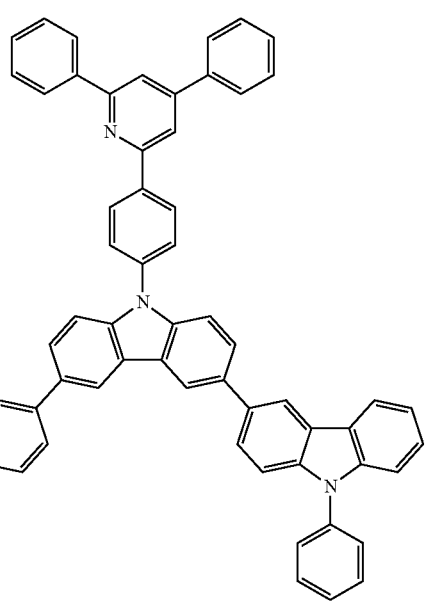
[Chemical Formula 16b]
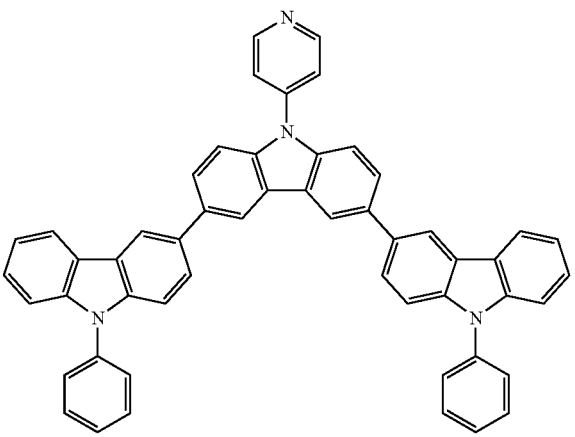
[Chemical Formula 17b]
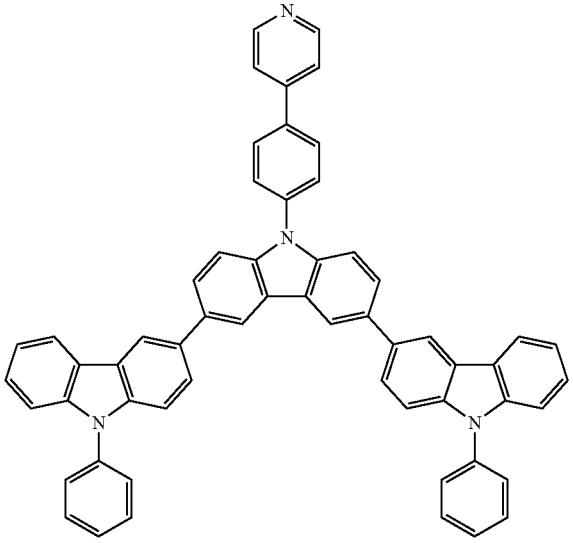

[Chemical Formula 18b]
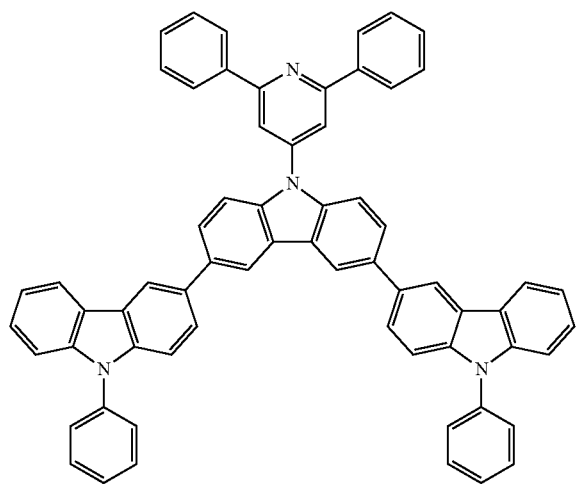
[Chemical Formula 19b]
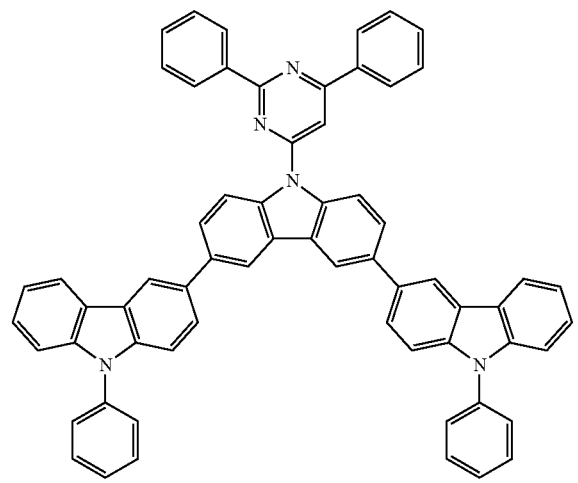
[Chemical Formula 20b]
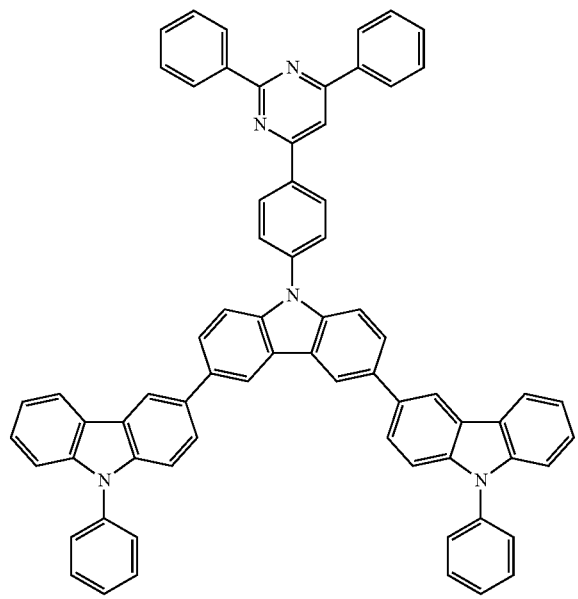
[Chemical Formula 21b]
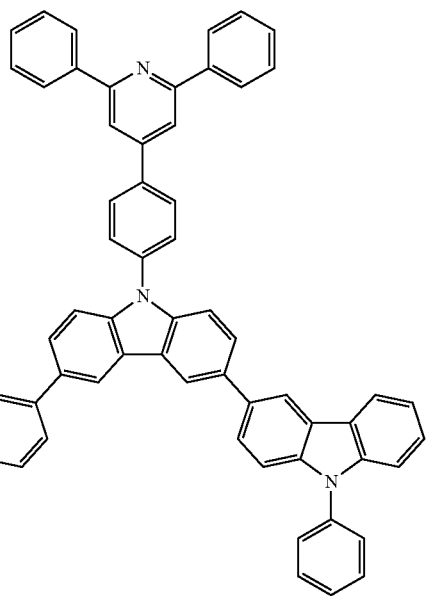
[Chemical Formula 22b]
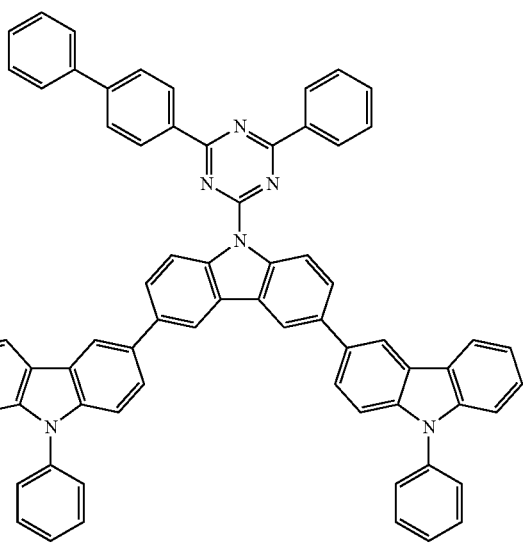

[Chemical Formula 23b]
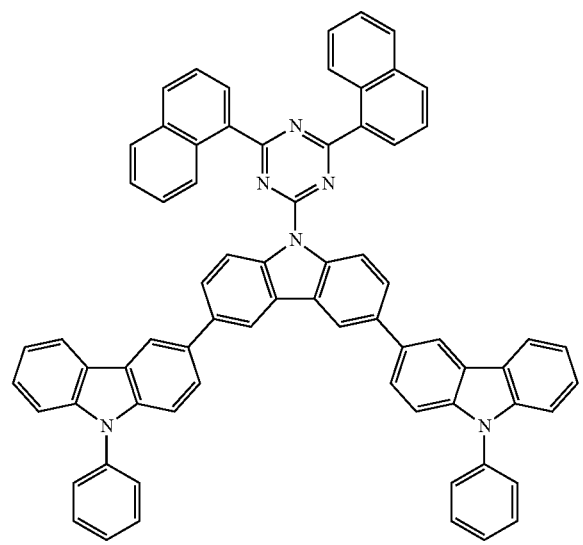
[Chemical Formula 25b]
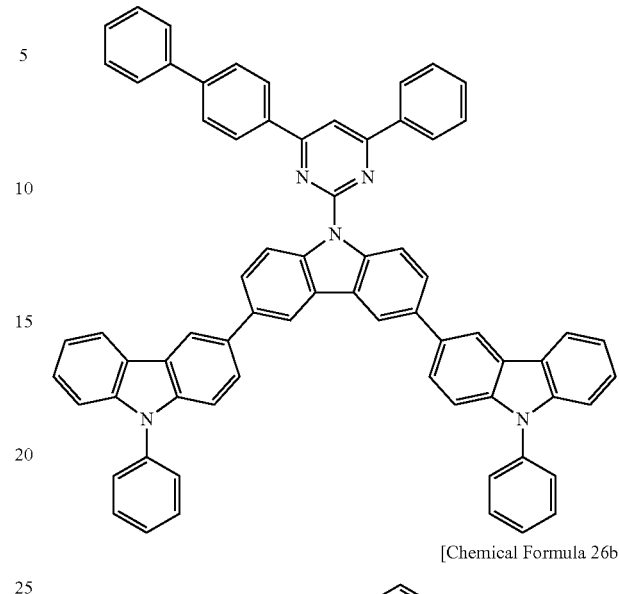
[Chemical Formula 26b]
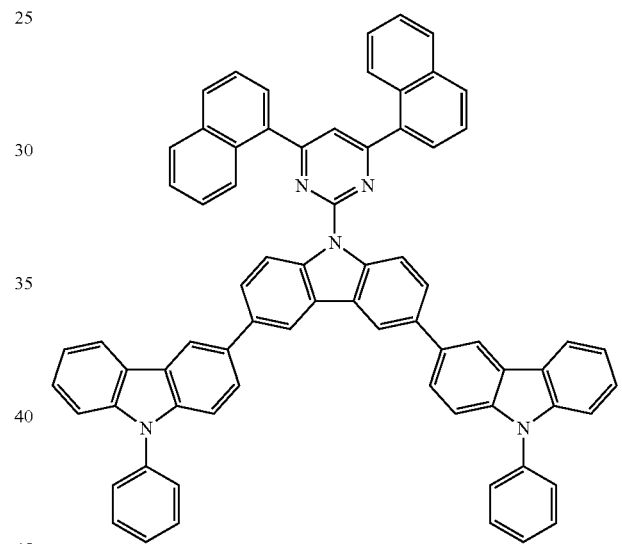
[Chemical Formula 24b]
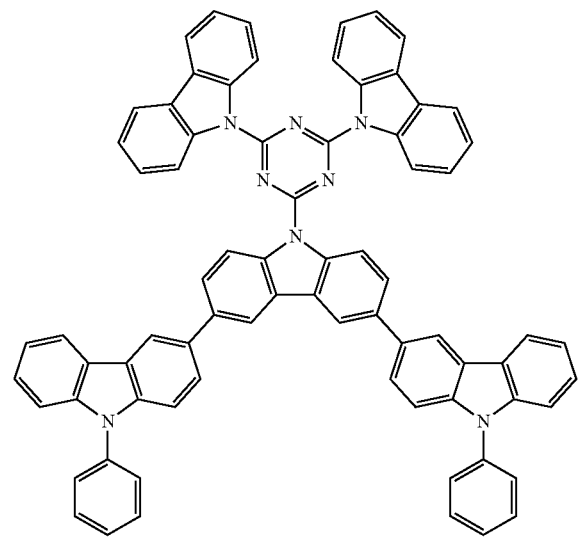
[Chemical Formula 27b]
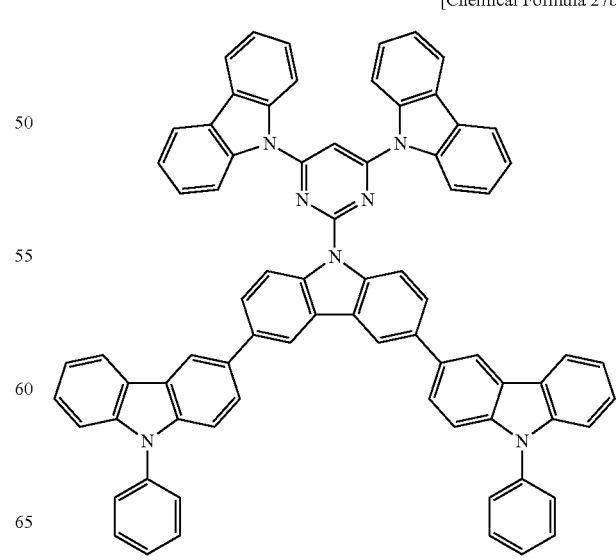

[Chemical Formula 28b]
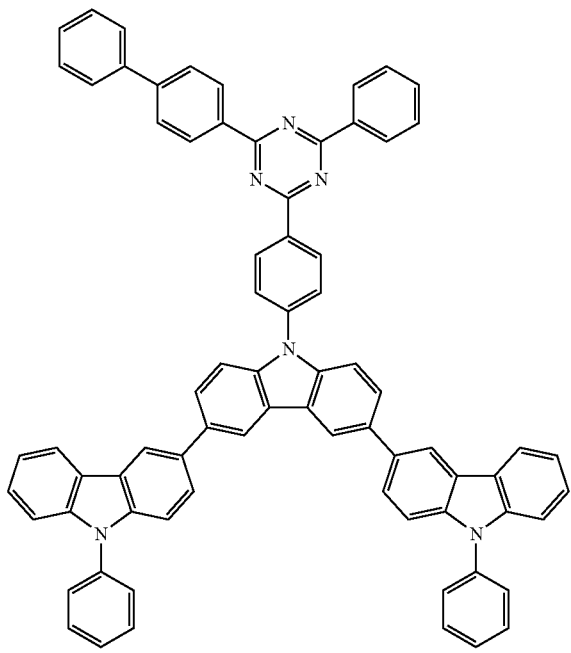
[Chemical Formula 30b]
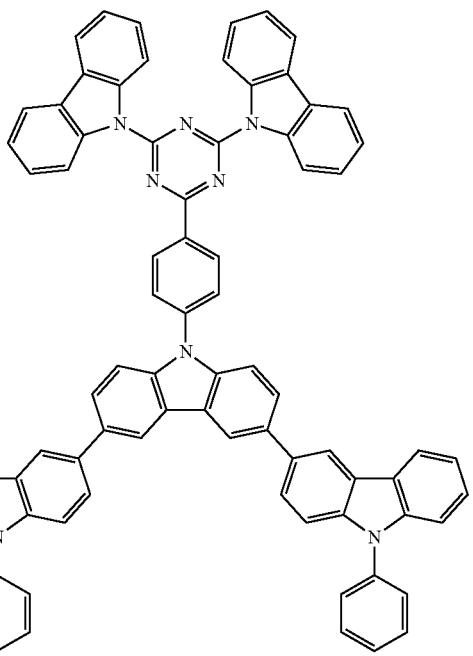
[Chemical Formula 29b]
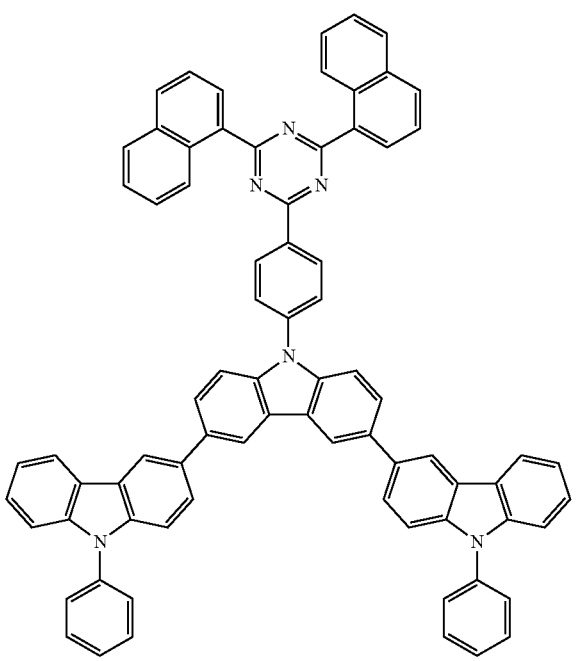
[Chemical Formula 31b]
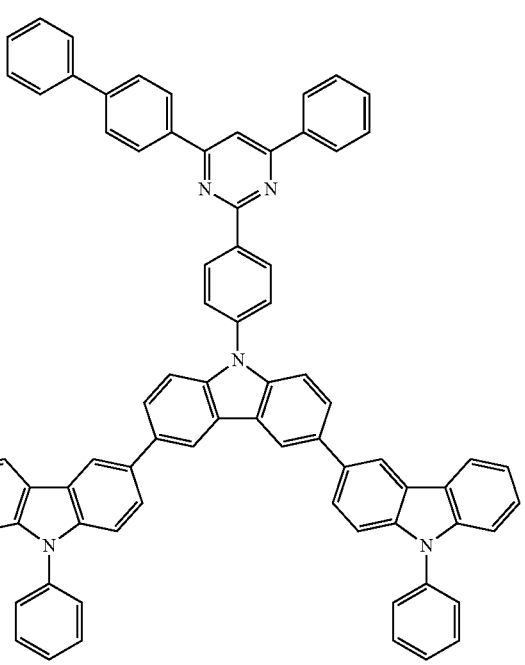

[Chemical Formula 32b]
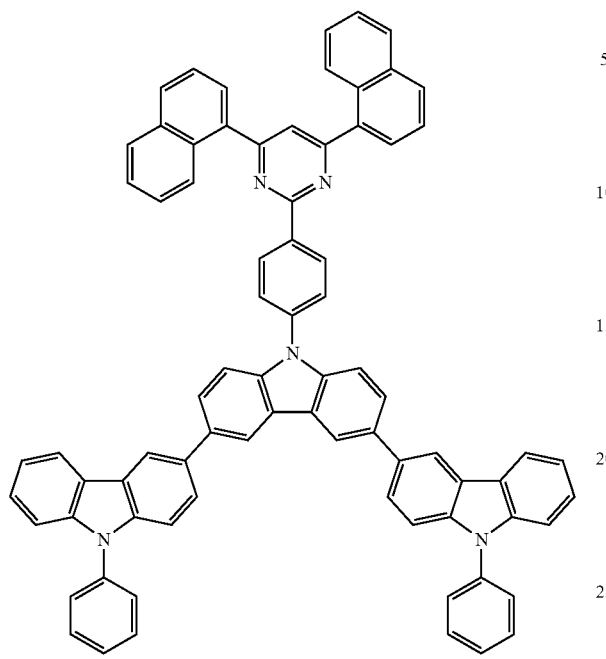
[Chemical Formula 33b]
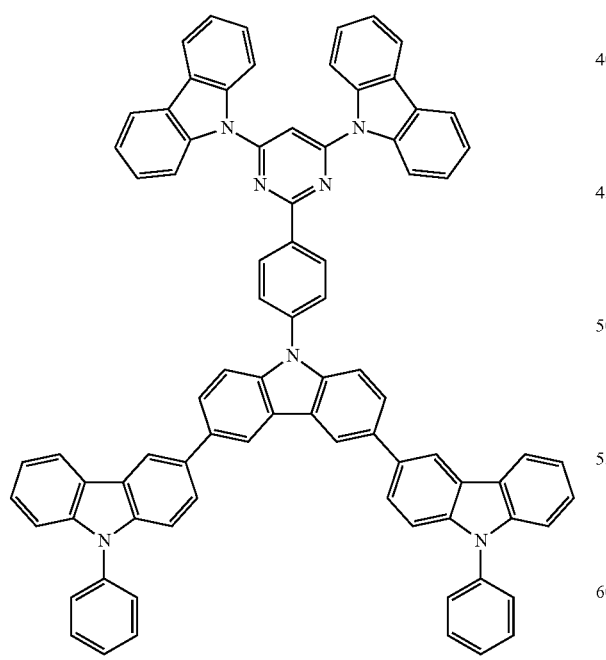
[Chemical Formula 1c]
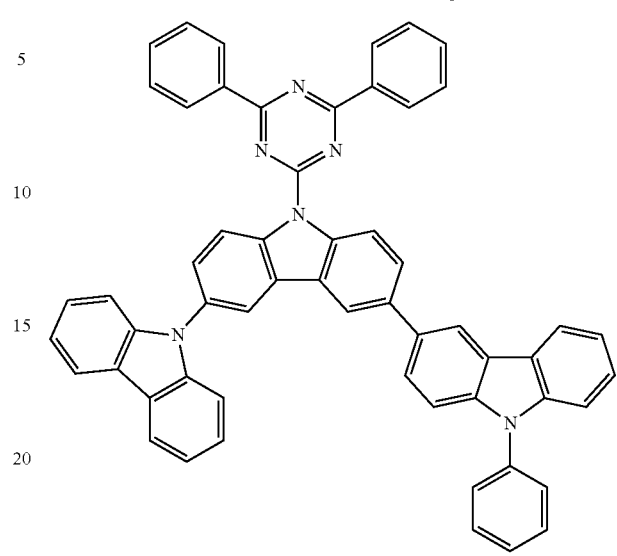
[Chemical Formula 2c]
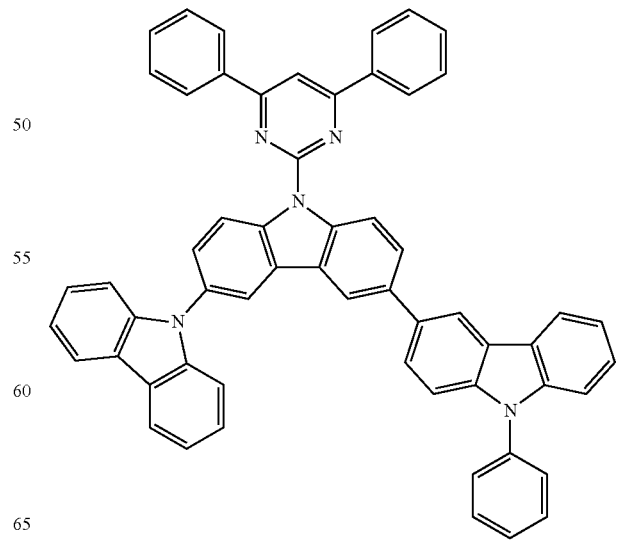
The compound for an organic optoelectronic device may be a compound represented by, e.g., one of the following Chemical Formulae 1c to 37c.

[Chemical Formula 3c]
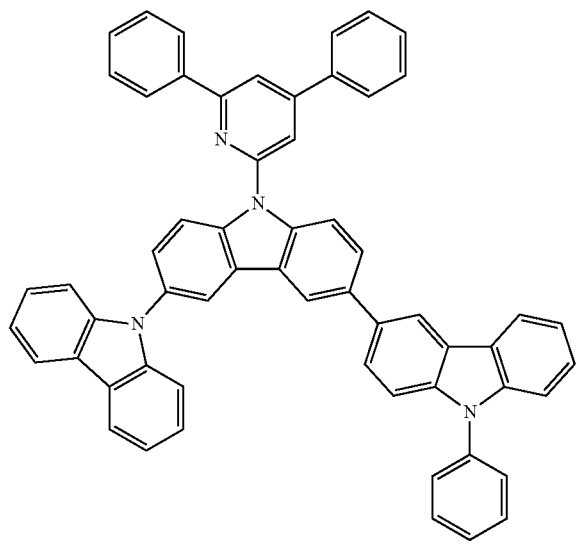
[Chemical Formula 4c]
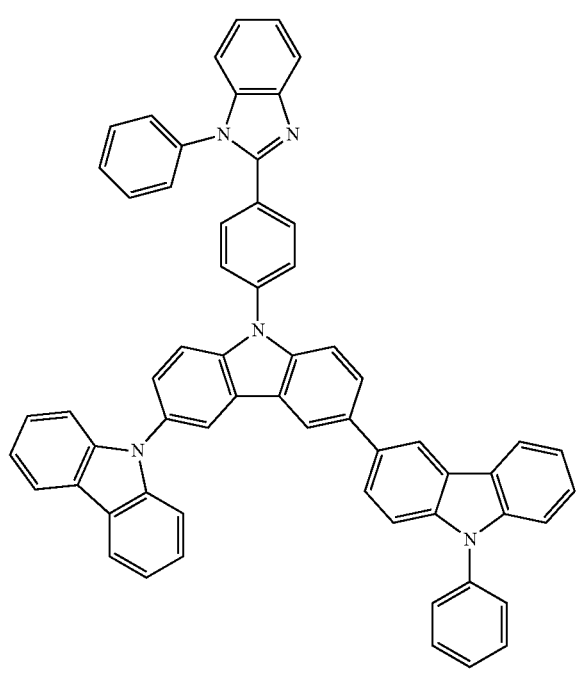
[Chemical Formula 5c]
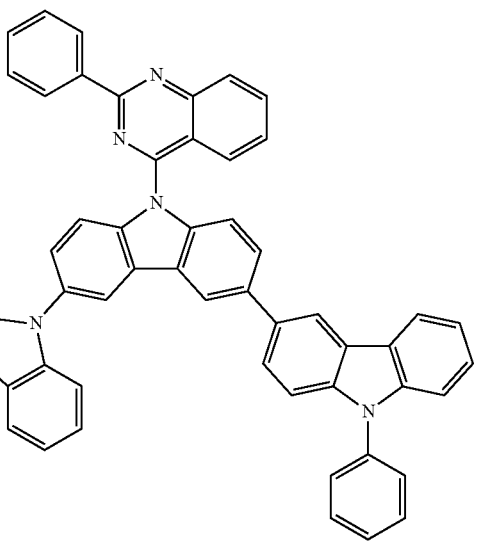
[Chemical Formula 6c]
[Chemical Formula 7c]
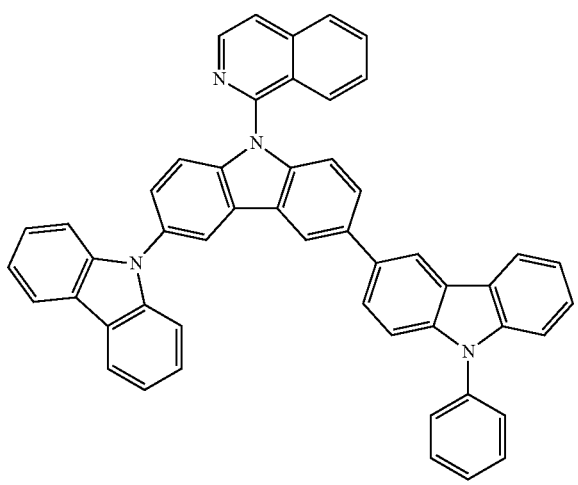

[Chemical Formula 8c]
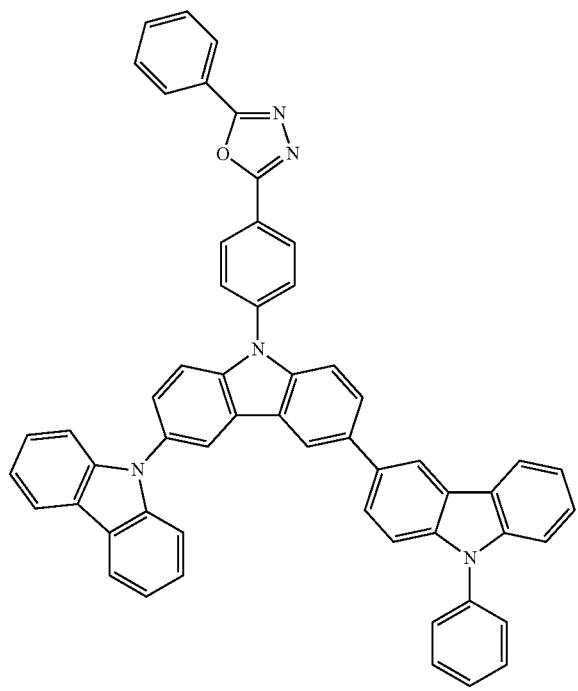
[Chemical Formula 9c]
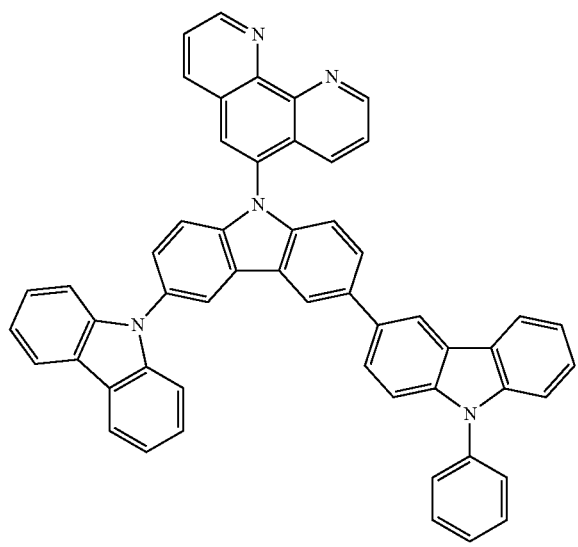
[Chemical Formula 10c]
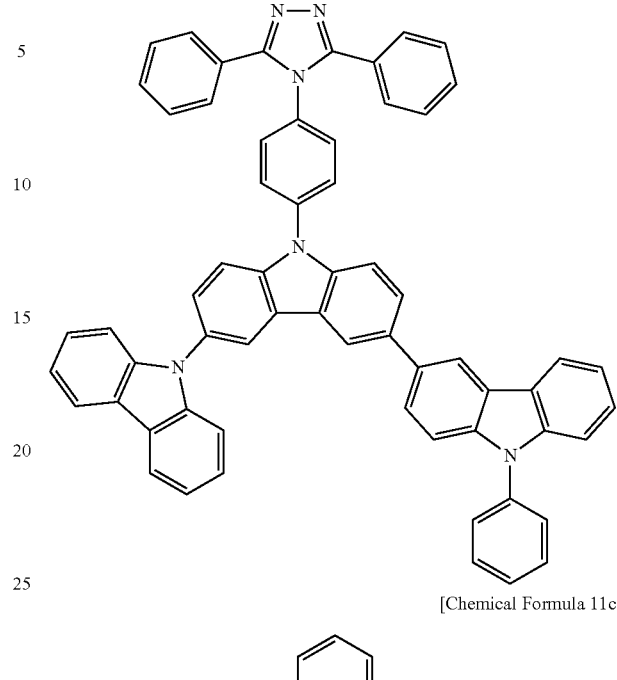
[Chemical Formula 11c]
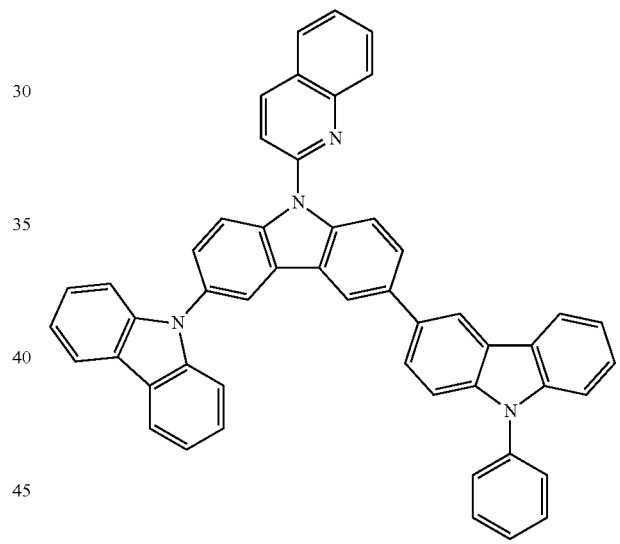
[Chemical Formula 12c]
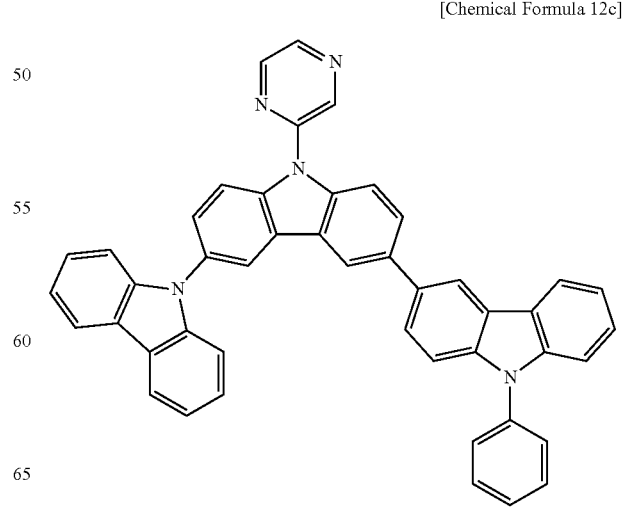

[Chemical Formula 13c]
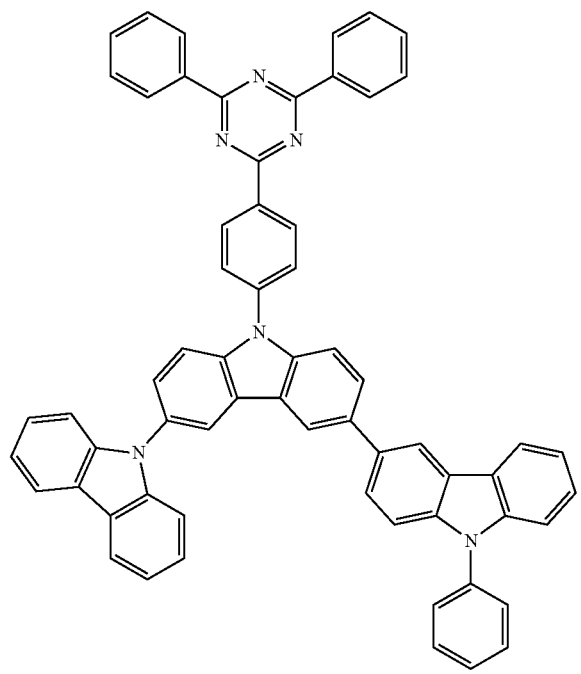
[Chemical Formula 15c]
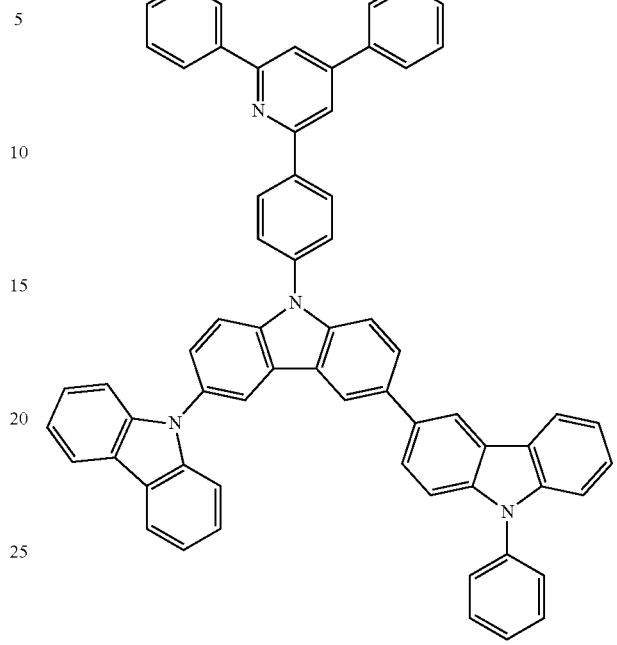
[Chemical Formula 14c]
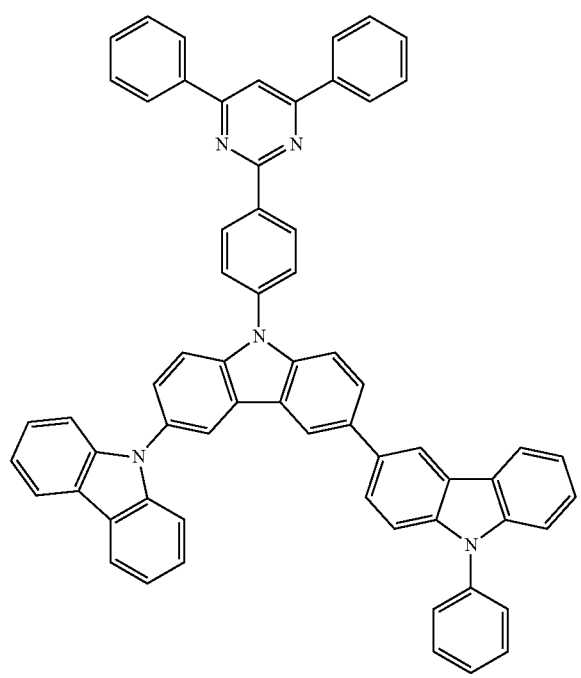
[Chemical Formula 16c]
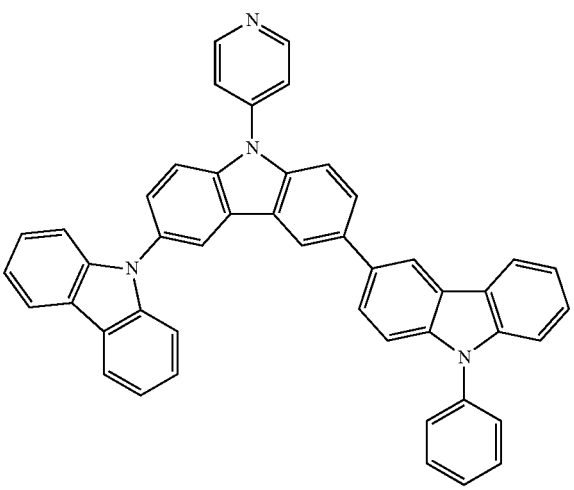

[Chemical Formula 17c]
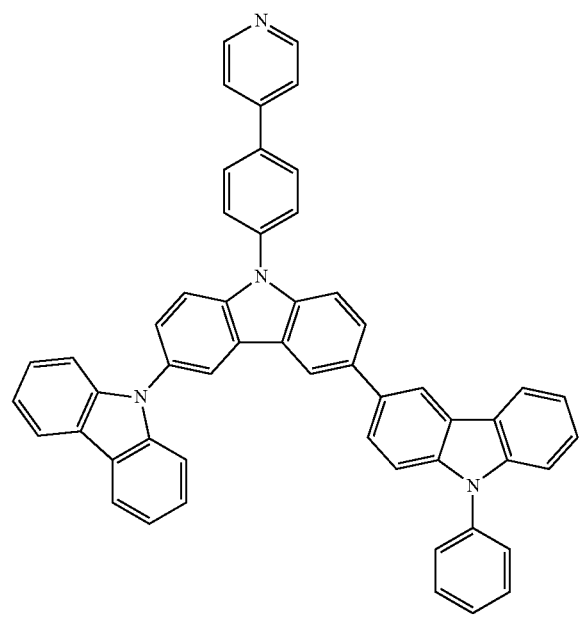
[Chemical Formula 19c]
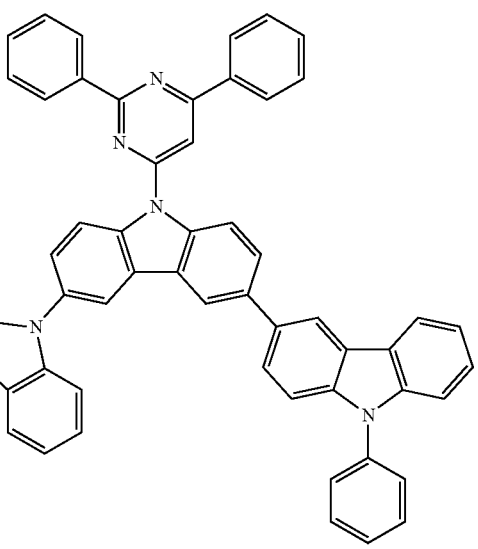
[Chemical Formula 18c]
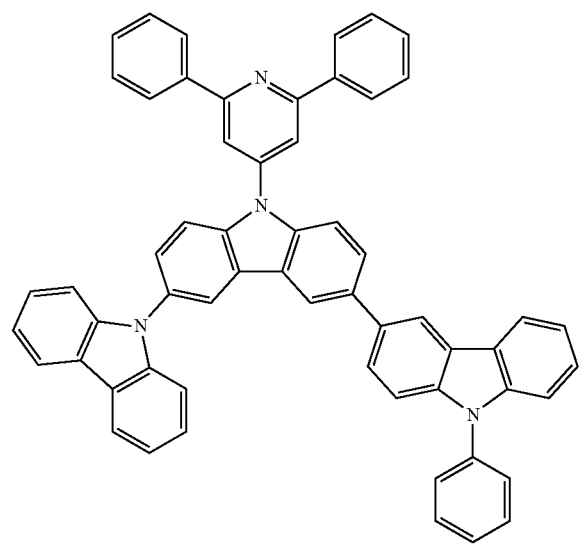
[Chemical Formula 20c]
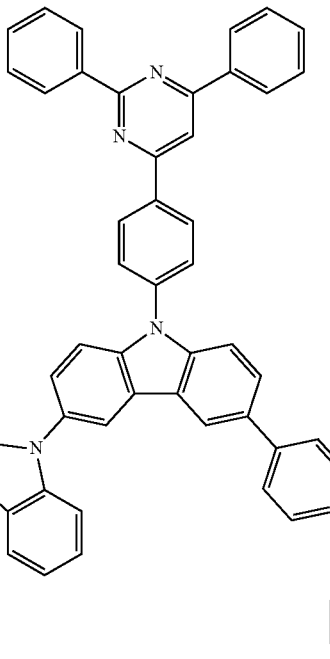

[Chemical Formula 21c]
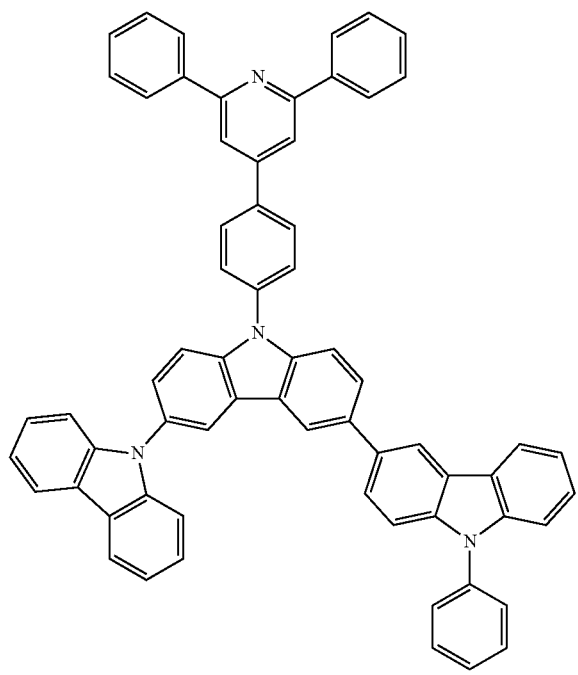
[Chemical Formula 23c]
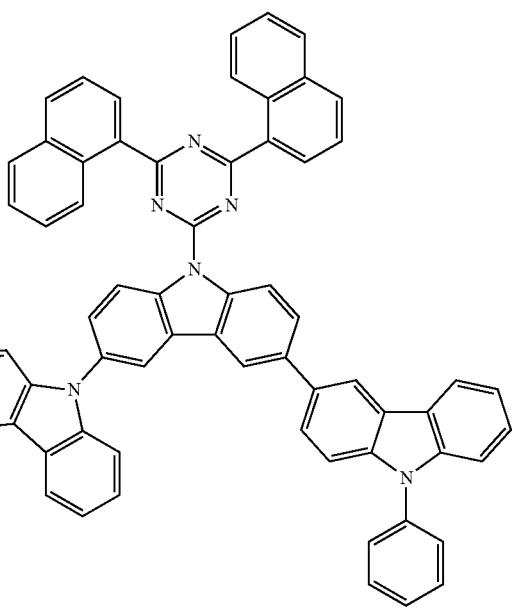
[Chemical Formula 22c]
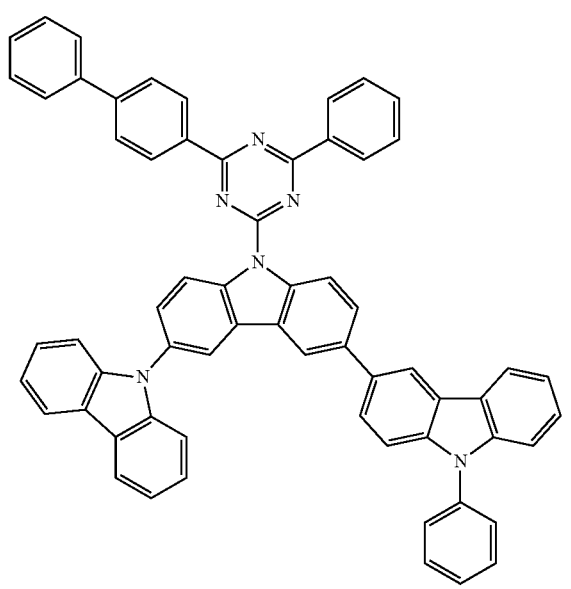
[Chemical Formula 24c]

[Chemical Formula 25c]
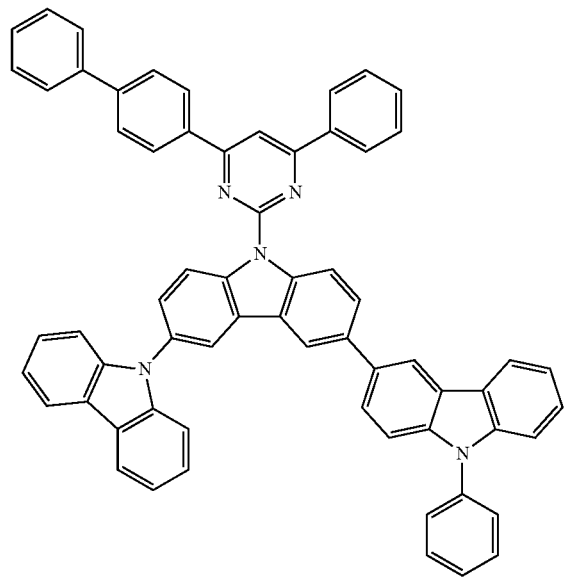
[Chemical Formula 27c]
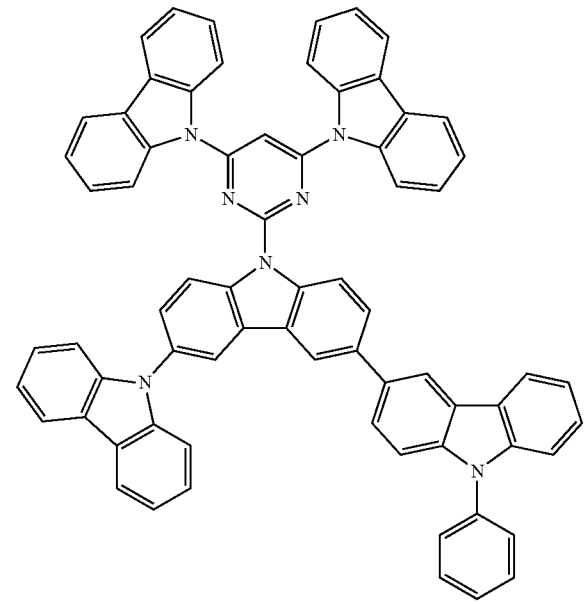
[Chemical Formula 26c]
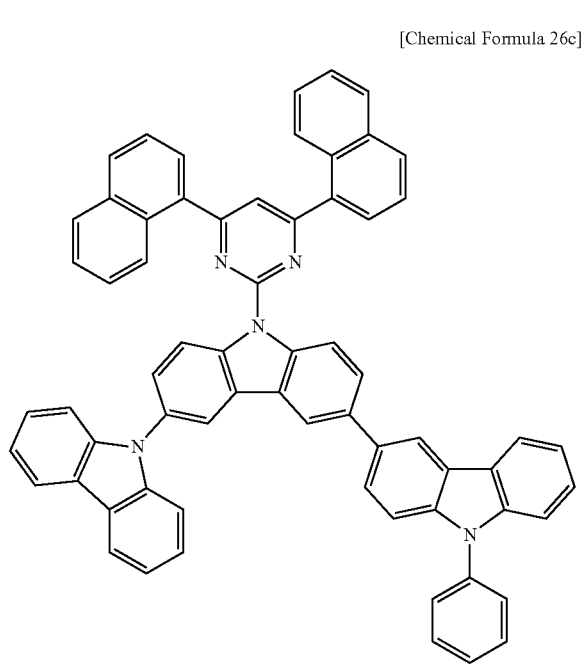
[Chemical Formula 28c]
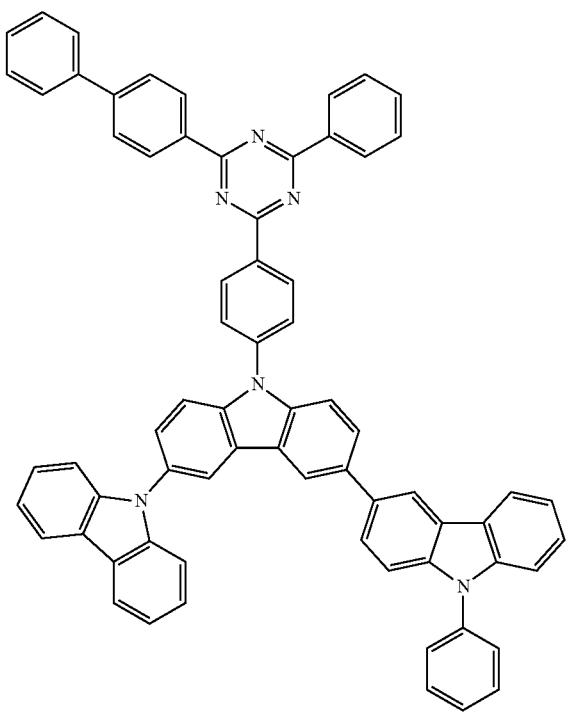

[Chemical Formula 29c]
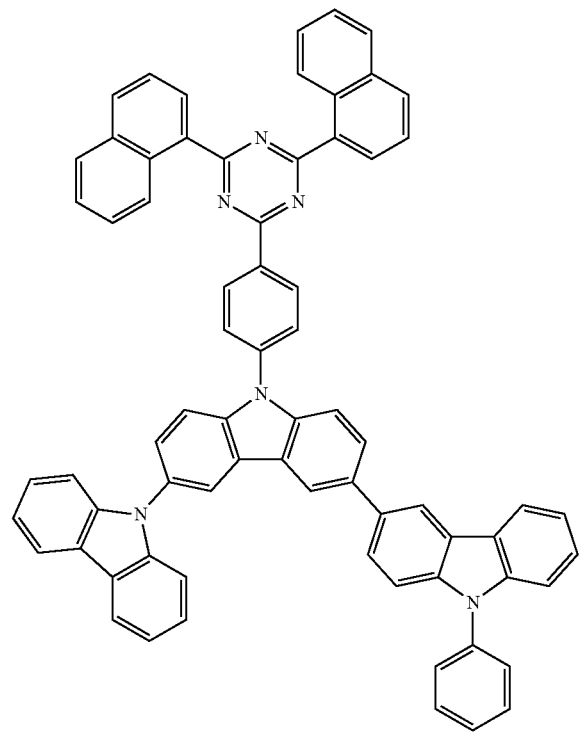
[Chemical Formula 31c]
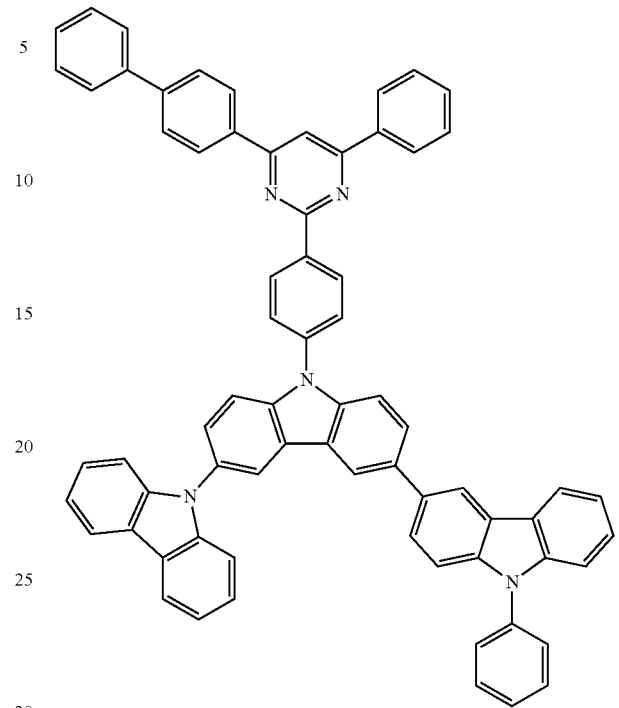
[Chemical Formula 30c]
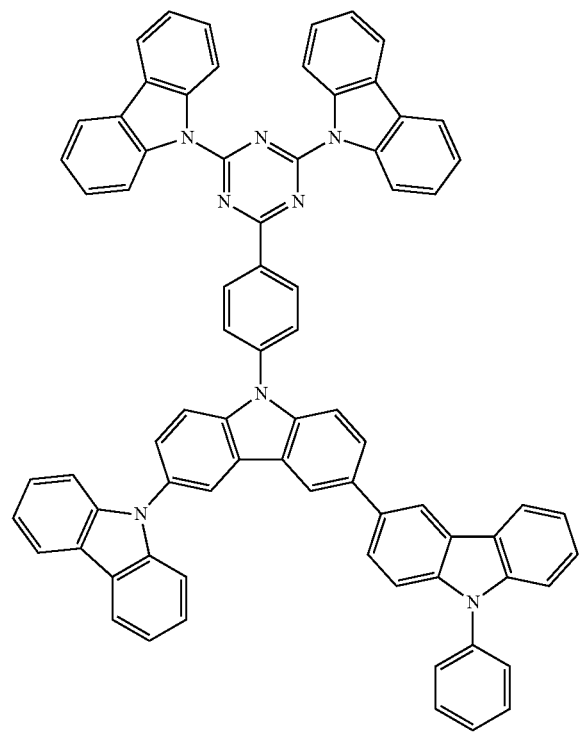
[Chemical Formula 32c]
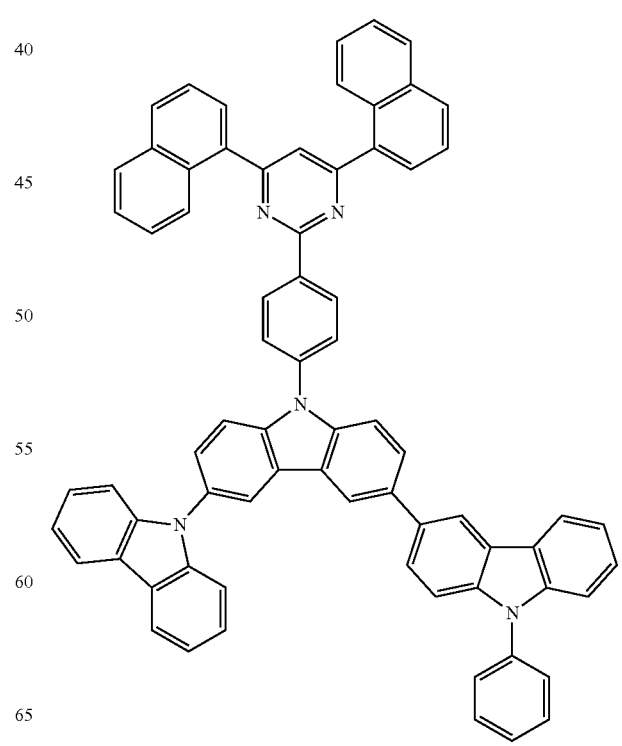

[Chemical Formula 33c]
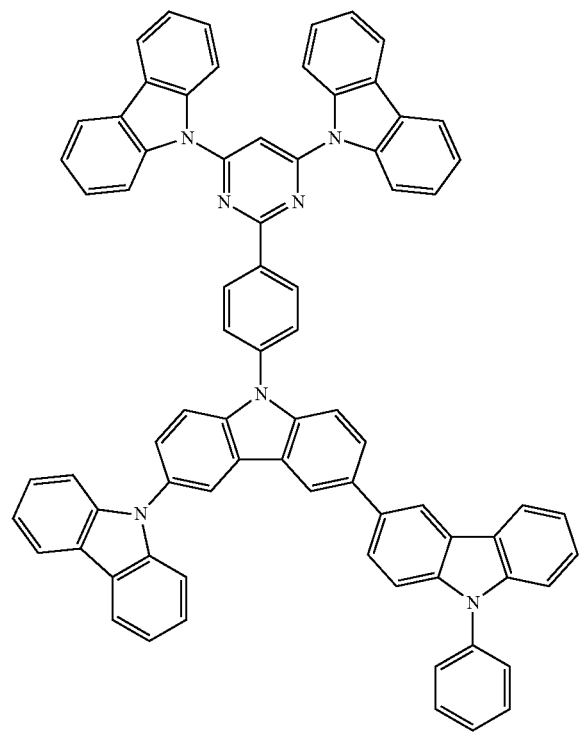
[Chemical Formula 34c]
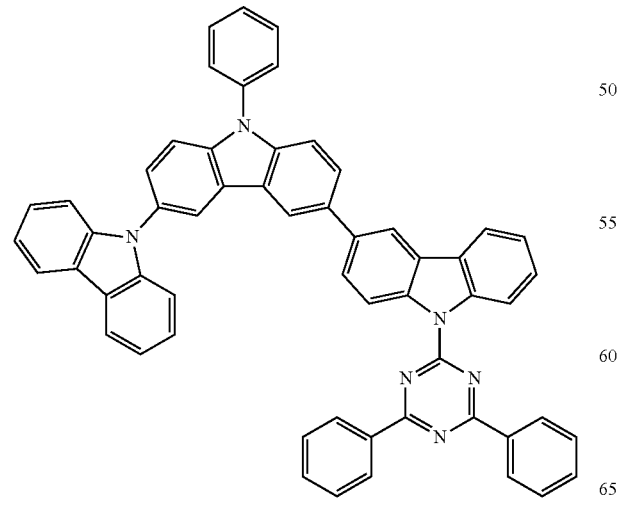
[Chemical Formula 35c]
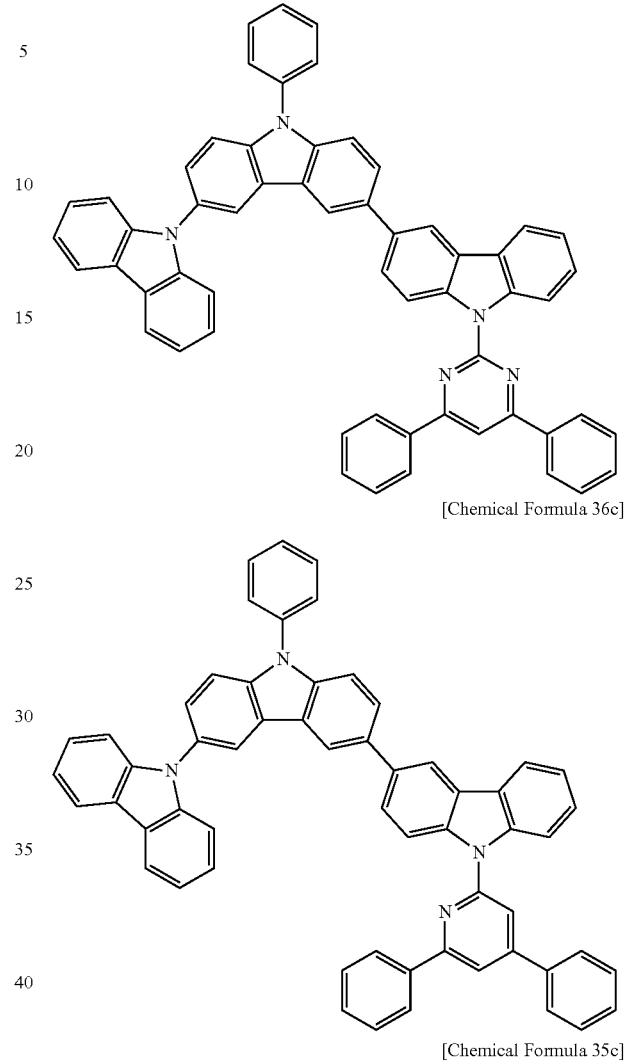
[Chemical Formula 36c]
[Chemical Formula 35c]
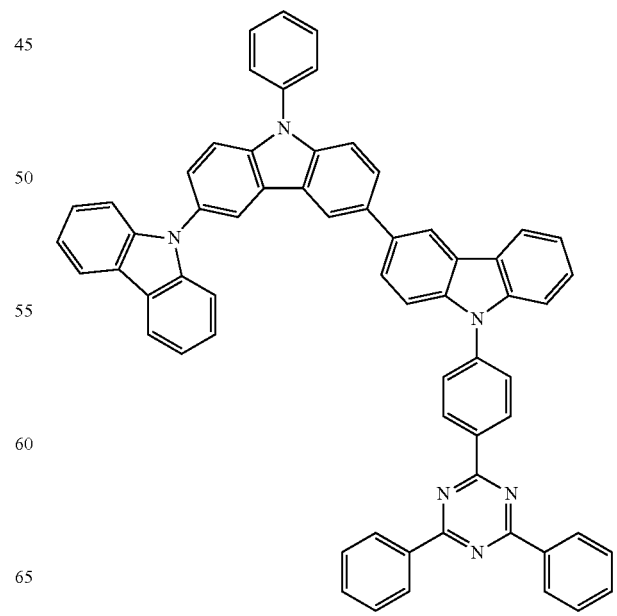

[Chemical Formula 36c]
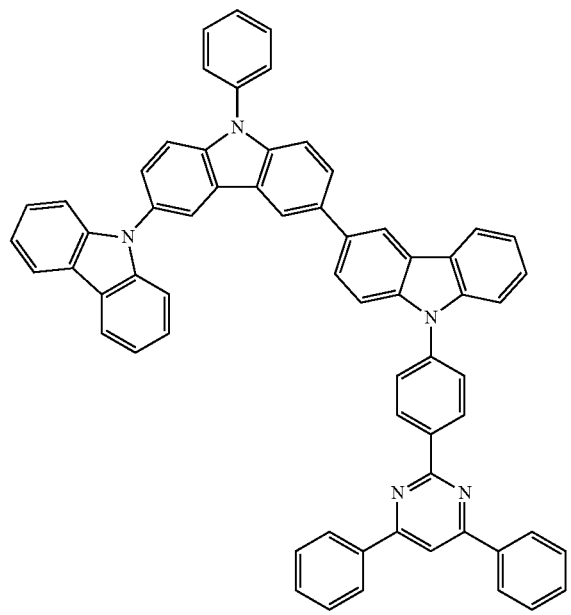
[Chemical Formula 1d]
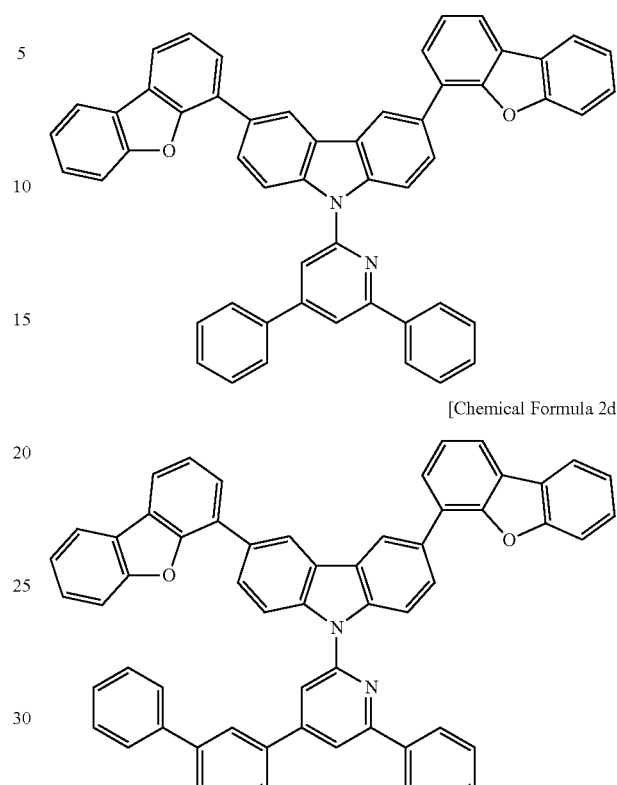
[Chemical Formula 2d]
[Chemical Formula 3d]
[Chemical Formula 37c]
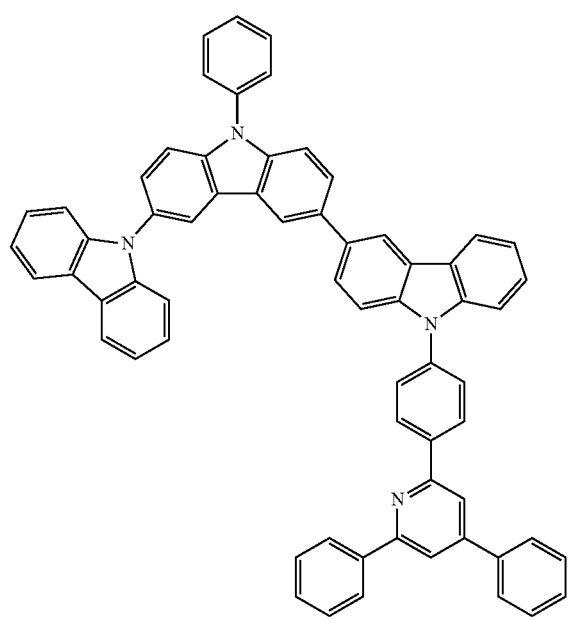
[Chemical Formula 4d]
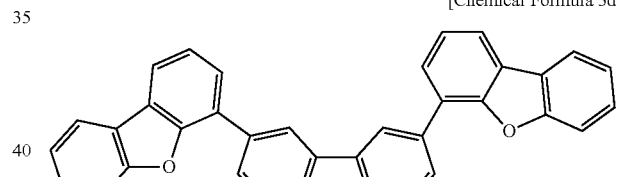
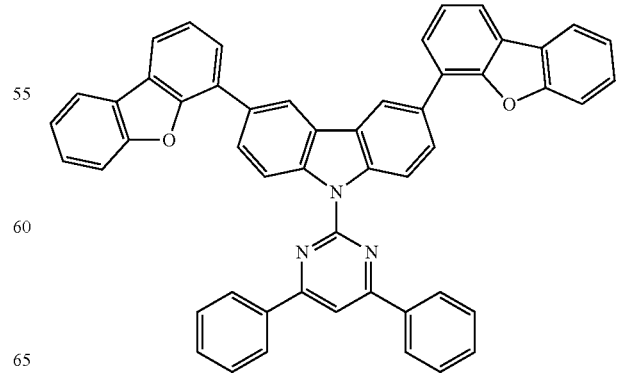
The compound for an organic optoelectronic device may be a compound represented by, e.g., one of the following Chemical Formulae 1d to 33d.

[Chemical Formula 5d]
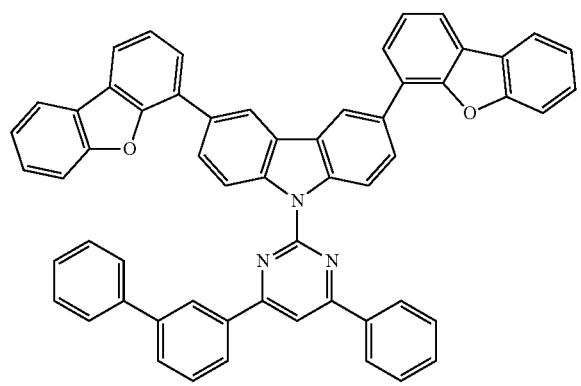
[Chemical Formula 6d]
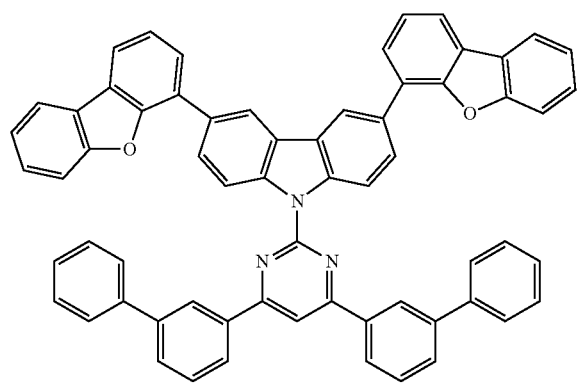
[Chemical Formula 7d]
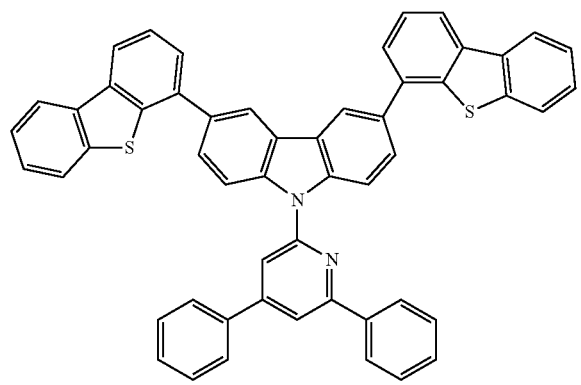
[Chemical Formula 8d]
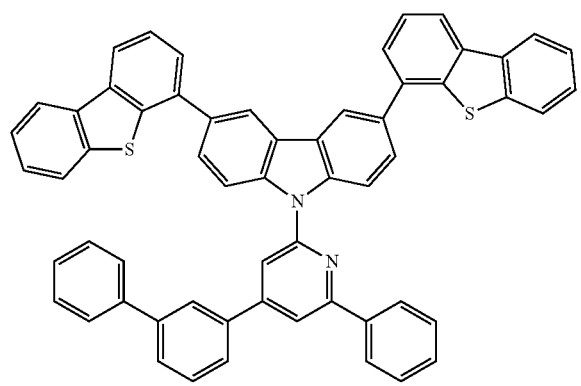
[Chemical Formula 9d]
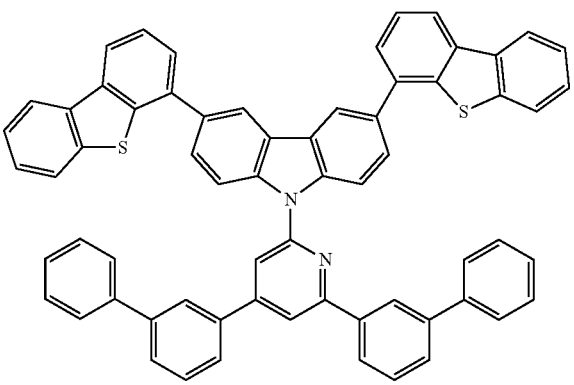
[Chemical Formula 10d]
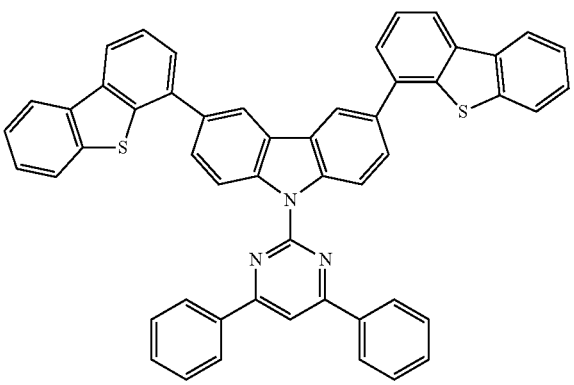
[Chemical Formula 11d]
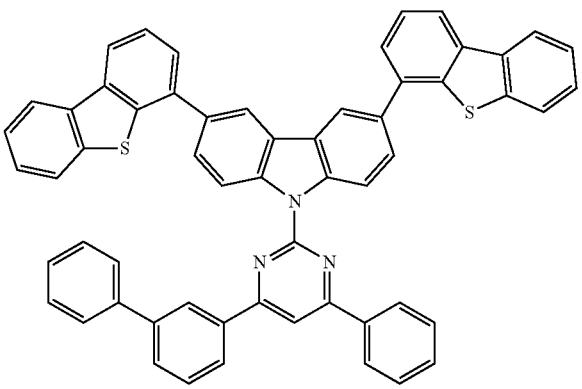
[Chemical Formula 12d]
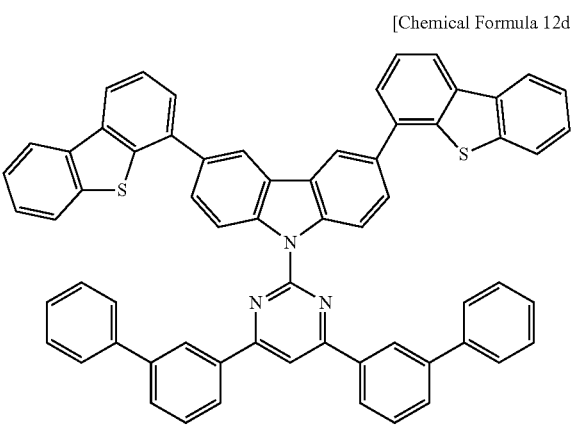

[Chemical Formula 13d]
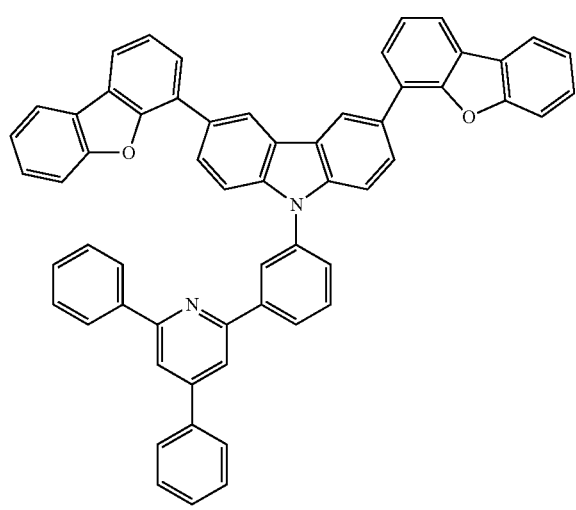
[Chemical Formula 14d]
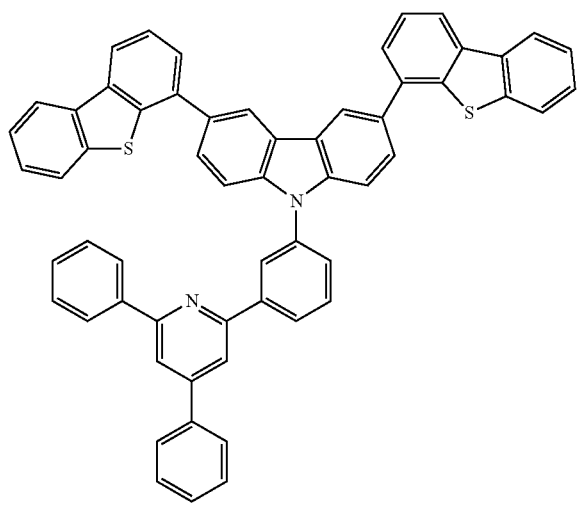
[Chemical Formula 15d]
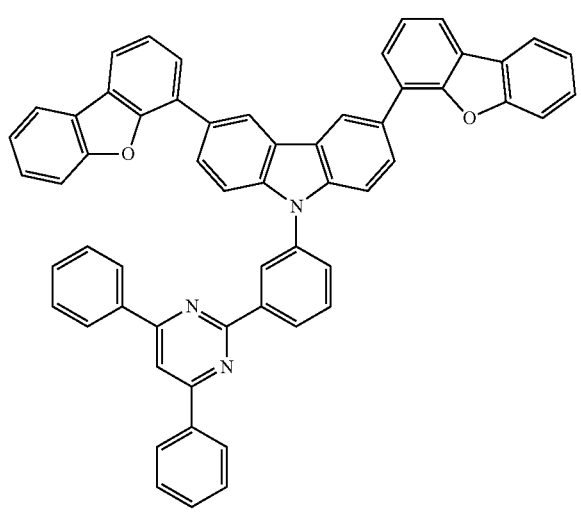
[Chemical Formula 16d]
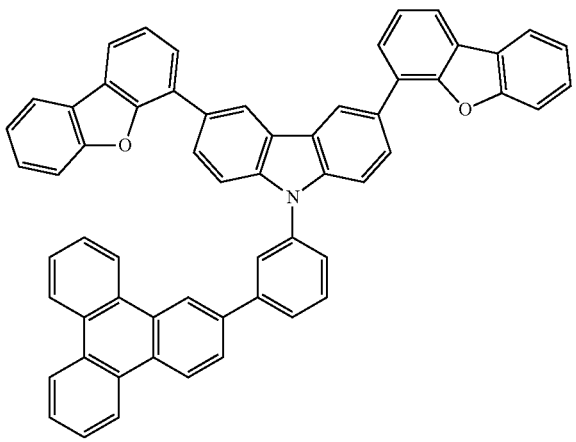
[Chemical Formula 17d]
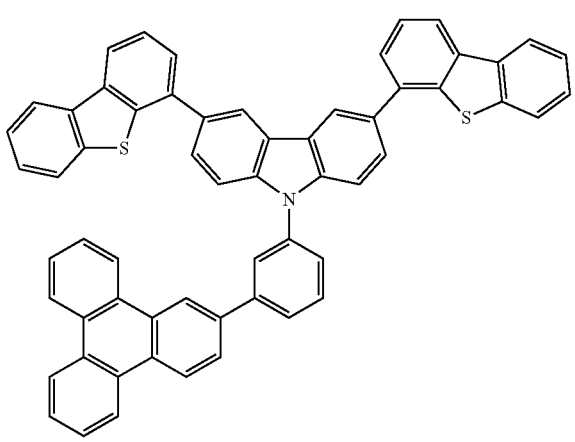
[Chemical Formula 18d]
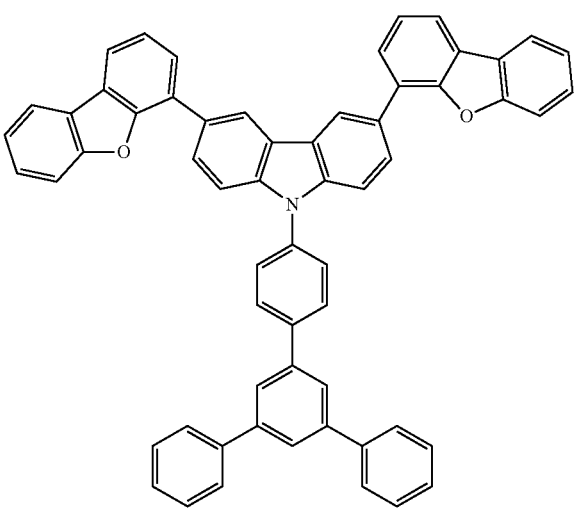

[Chemical Formula 19d]
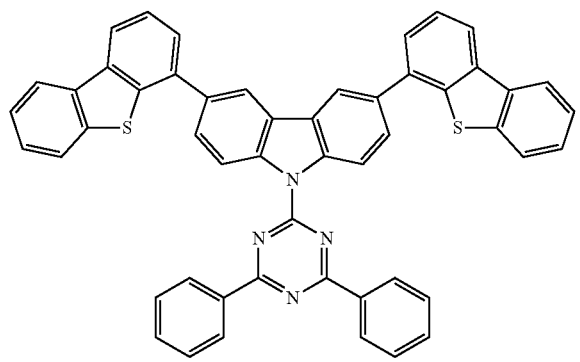
[Chemical Formula 20d]
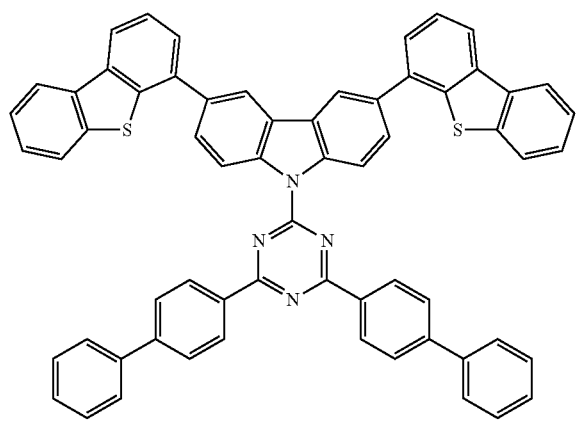
[Chemical Formula 21d]
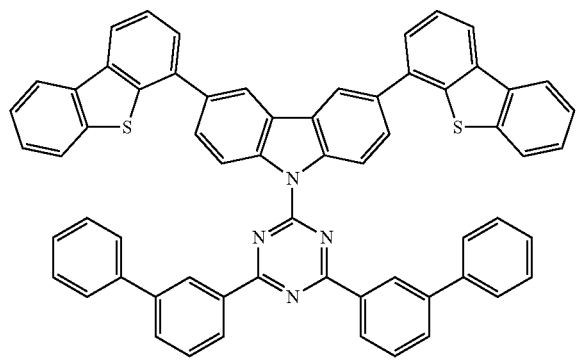
[Chemical Formula 22d]
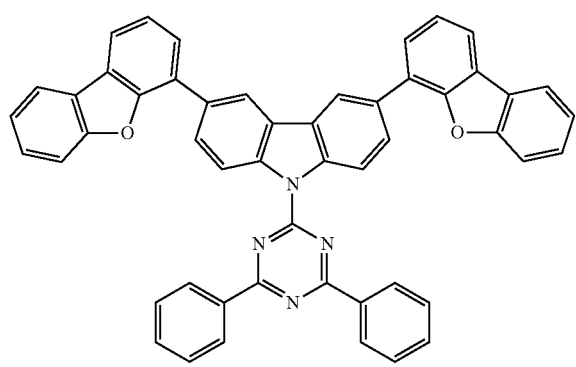
[Chemical Formula 23d]
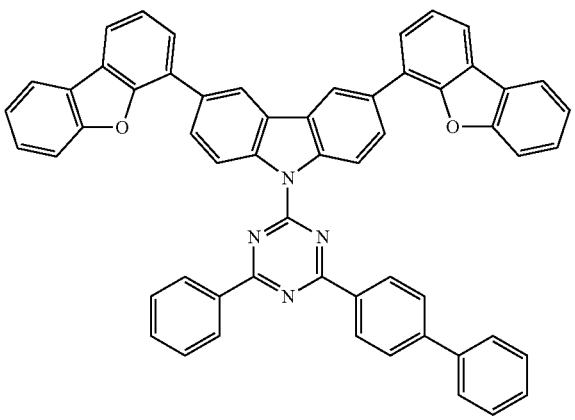
[Chemical Formula 24d]
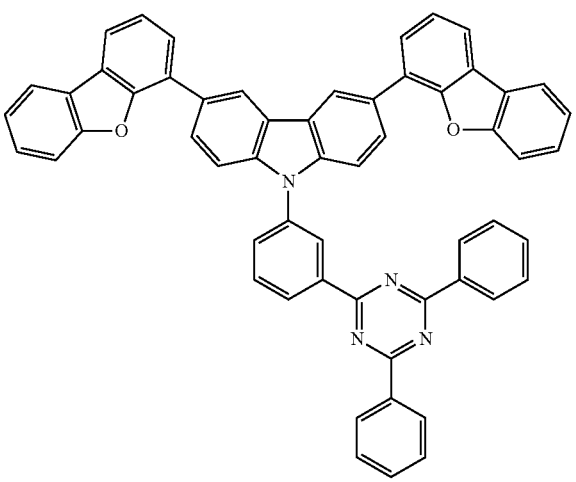
[Chemical Formula 25d]
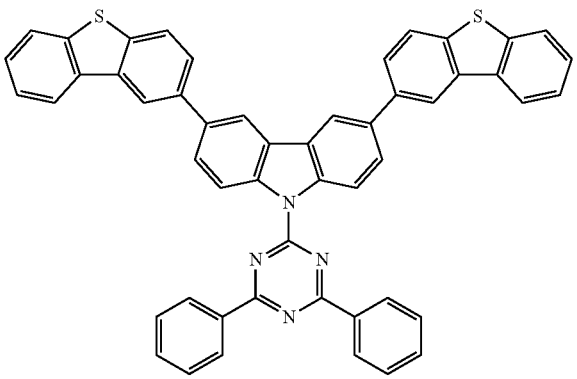

-continued
[Chemical Formula 26d]
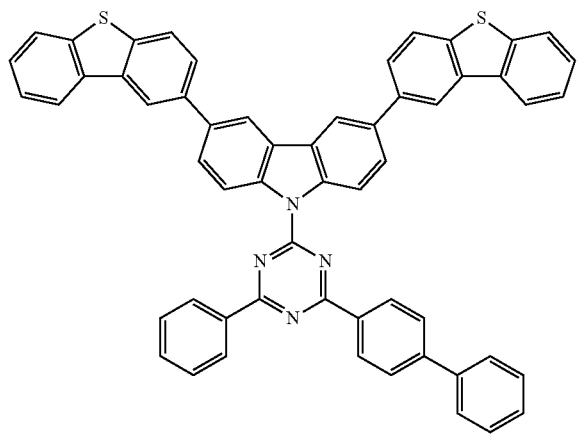
[Chemical Formula 27d]
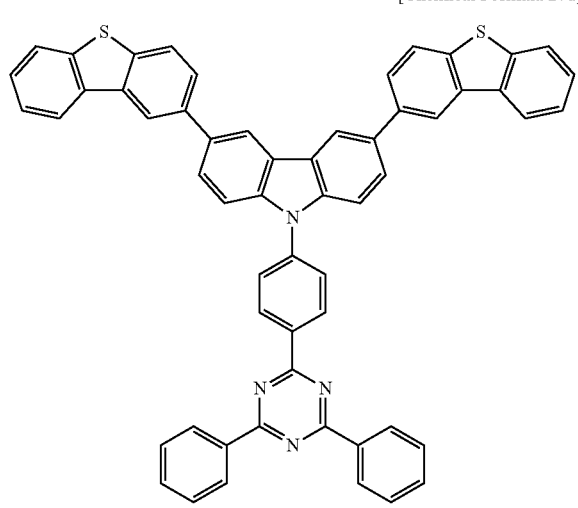
[Chemical Formula 28d]
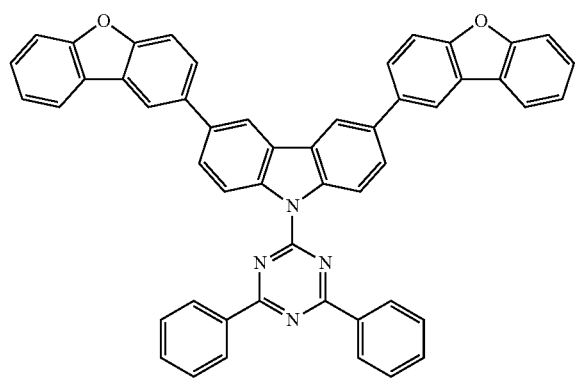
-continued
[Chemical Formula 29d]
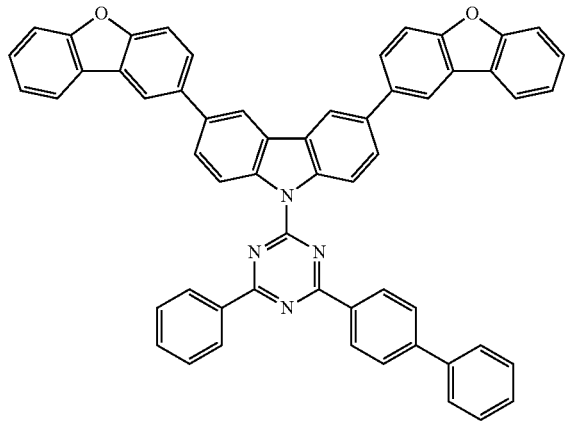
[Chemical Formula 30d]
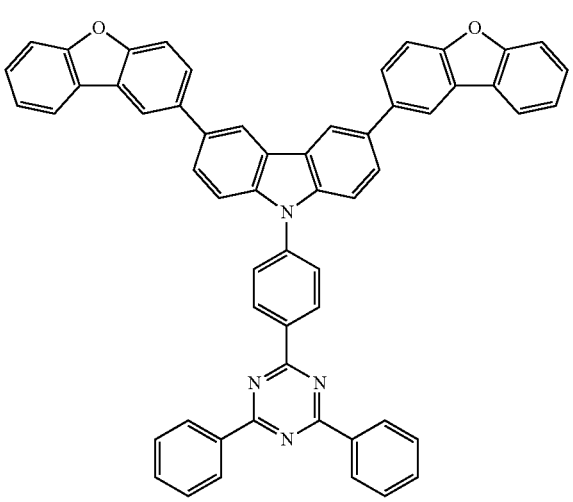
[Chemical Formula 31d]
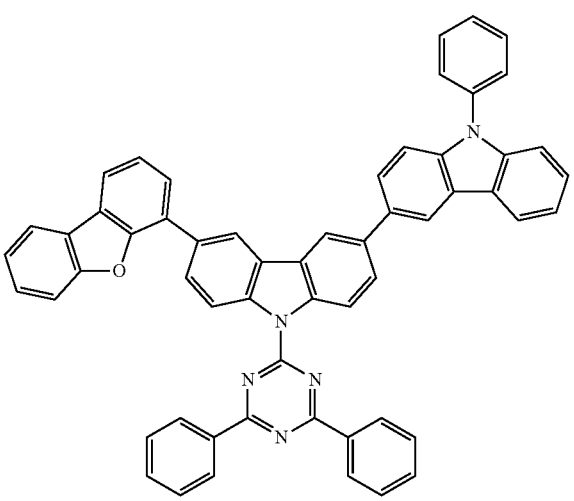

-continued

[Chemical Formula 32d]

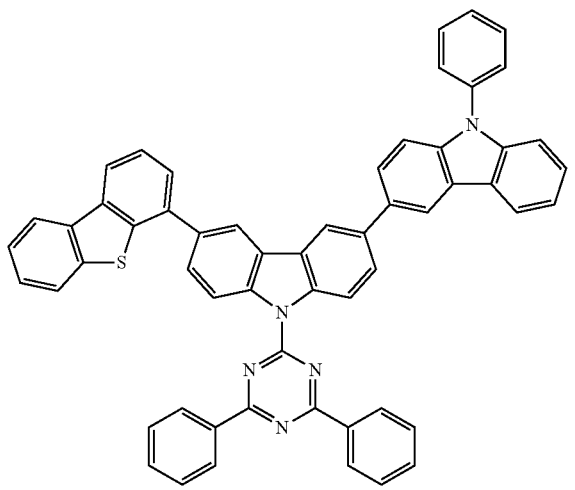

[Chemical Formula 33d]

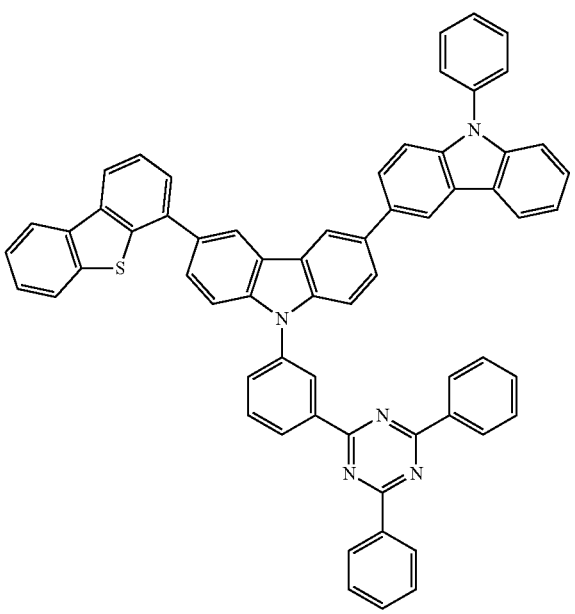

The compound for an organic optoelectronic device such as the above compounds may exhibit a glass transition temperature of greater than or equal to 110° C. and a thermal decomposition temperature of greater than or equal to 400° C., indicating improved thermal stability. Thereby, it may be possible to produce an organic optoelectronic device having a high efficiency.

The compound for an organic optoelectronic device including the above compounds may play a role for emitting light or injecting and/or transporting electrons, and also act as a light emitting host with an appropriate dopant. Thus, the compound for an organic optoelectronic device may be used as, e.g., a phosphorescent or fluorescent host material, a blue light emitting dopant material, or an electron transport material.

The compound for an organic optoelectronic device according to an example embodiment may used for an organic thin layer, and it may improve the life-span characteristic, efficiency characteristic, electrochemical stability, and thermal stability of an organic optoelectronic device and decrease the driving voltage.

Therefore, according to another example embodiment, an organic optoelectronic device that includes the compound for an organic optoelectronic device is provided. The organic optoelectronic device may include an organic photoelectric device, an organic light emitting diode, an organic solar cell, an organic transistor, an organic photo conductor drum, an organic memory device, and the like. For example, the compound for an organic optoelectronic device according to an example embodiment may be included in an electrode or an electrode buffer layer in the organic solar cell to improve the quantum efficiency, and it may be used as an electrode material for a gate, a source-drain electrode, or the like in the organic transistor.

Another example embodiment provides an organic light emitting diode that includes an anode, a cathode, and at least one organic thin layer between the anode and the cathode, and the at least one organic thin layer may include the compound for an organic optoelectronic device according to an example embodiment.

The organic thin layer that may include the compound for an organic optoelectronic device may include a layer selected from the group of an emission layer, a hole transport layer (HTL), a hole injection layer (HIL), an electron transport layer (ETL), an electron injection layer (EIL), a hole blocking layer, or a combination thereof. The at least one layer includes the compound for an organic optoelectronic device according to an example embodiment. For example, the compound for an organic optoelectronic device according to an example embodiment may be included in an electron transport layer (ETL) or an electron injection layer (EIL). In addition, when the compound for an organic optoelectronic device is included in the emission layer, the compound for an organic optoelectronic device may be included as a phosphorescent or fluorescent host, and, for example, as a fluorescent blue dopant material.

FIGS. 1 to 5 are cross-sectional views showing organic light emitting diodes including the compound for an organic optoelectronic device according to an example embodiment.

Referring to FIGS. 1 to 5, organic light emitting diodes 100, 200, 300, 400, and 500 according to an example embodiment include at least one organic thin layer 105 interposed between an anode 120 and a cathode 110.

The anode 120 includes an anode material having a large work function to help hole injection into an organic thin layer. The anode material includes: a metal such as nickel, platinum, vanadium, chromium, copper, zinc, and gold, or alloys thereof; a metal oxide such as zinc oxide, indium oxide, indium tin oxide (ITO), and indium zinc oxide (IZO); a bonded metal and oxide such as ZnO:Al or $SnO_2$:Sb; or a conductive polymer such as poly(3-methylthiophene), poly [3,4-(ethylene-1,2-dioxy)thiophene] (PEDT), polypyrrole, and polyaniline, etc. A transparent electrode including indium tin oxide (ITO) may be included an anode.

The cathode 110 includes a cathode material having a small work function to help electron injection into an organic thin layer. The cathode material includes: a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, $LiO_2$/Al, LiF/Ca, LiF/Al, and $BaF_2$/Ca, etc. A metal electrode including aluminum may be included as a cathode.

Referring to FIG. 1, the organic light emitting diode 100 includes an organic thin layer 105 including only an emission layer 130.

Figure 2:
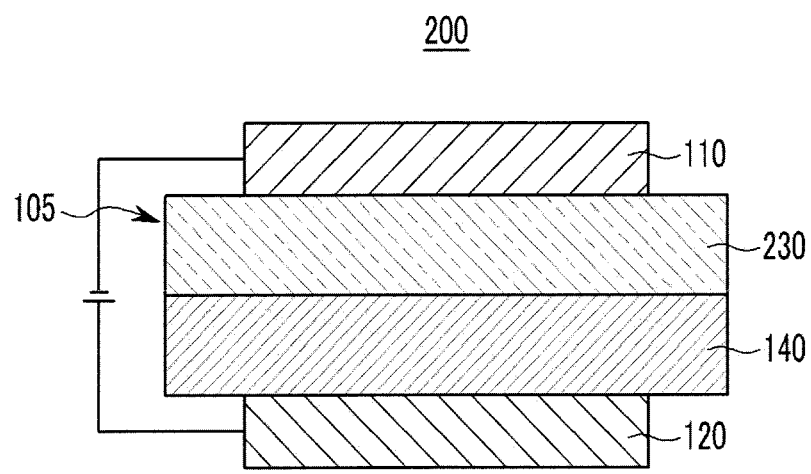

Referring to FIG. 2, a double-layered organic light emitting diode 200 includes an organic thin layer 105 including an emission layer 230 including an electron transport layer (ETL), and a hole transport layer (HTL) 140. As shown in FIG. 2, the organic thin layer 105 includes a double layer of the emission layer 230 and hole transport layer (HTL) 140. The emission layer 130 also functions as an electron transport layer (ETL), and the hole transport layer (HTL) 140 layer may have an excellent binding property with a transparent electrode such as ITO or an excellent hole transport capability.

Figure 3:
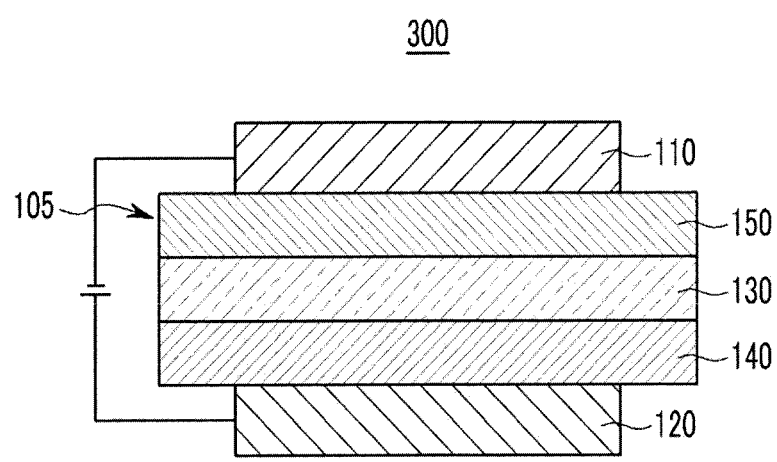

Referring to FIG. 3, a three-layered organic light emitting diode 300 includes an organic thin layer 105 including an electron transport layer (ETL) 150, an emission layer 130, and a hole transport layer (HTL) 140. The emission layer 130 may independently installed, and layers having an excellent electron transport capability or an excellent hole transport capability may be separately stacked.

Figure 4:
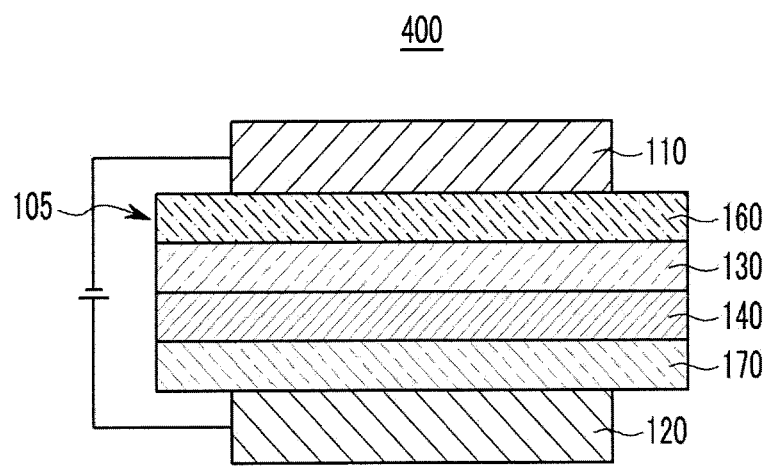

As shown in FIG. 4, a four-layered organic light emitting diode 400 includes an organic thin layer 105 including an electron injection layer (EIL) 160, an emission layer 130, a hole transport layer (HTL) 140, and a hole injection layer (HIL) 170 for adherence with the cathode of ITO.

Figure 5:
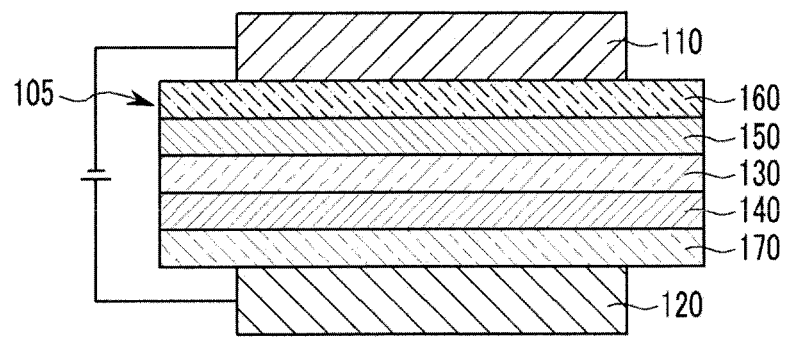

As shown in FIG. 5, a five layered organic light emitting diode 500 includes an organic thin layer 105 including an electron transport layer (ETL) 150, an emission layer 130, a hole transport layer (HTL) 140, and a hole injection layer (HIL) 170, and further includes an electron injection layer (EIL) 160 to help achieve a low voltage.

In FIGS. 1 to 5, the organic thin layer 105 including at least one selected from the group of an electron transport layer (ETL) 150, an electron injection layer (EIL) 160, emission layers 130 and 230, a hole transport layer (HTL) 140, a hole injection layer (HIL) 170, and combinations thereof includes a compound for an organic optoelectronic device. The compound for an organic optoelectronic device may be used for an electron transport layer (ETL) 150 including the electron transport layer (ETL) 150 or electron injection layer (EIL) 160. When it is used for the electron transport layer (ETL), it may be possible to provide an organic light emitting diode having a more simple structure because it does not require an additional hole blocking layer (not shown).

Furthermore, when the compound for an organic optoelectronic device is included in the emission layers 130 and 230, the material for the organic photoelectric device may be included as a phosphorescent or fluorescent host or a fluorescent blue dopant.

The organic light emitting diode may be fabricated by: forming an anode on a substrate; forming an organic thin layer in accordance with a dry coating method such as evaporation, sputtering, plasma plating, and ion plating or a wet coating method such as spin coating, dipping, and flow coating; and providing a cathode thereon.

Another example embodiment provides a display device including the organic light emitting diode according to the above embodiment.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Preparation of Compound for Organic Optoelectronic Device

Example 1

Synthesis of Compound Represented by Chemical Formula 1b

A compound represented by the above Chemical Formula 1b as a compound for an organic optoelectronic device was synthesized according to the following Reaction Scheme 1.

[Reaction Scheme 1]

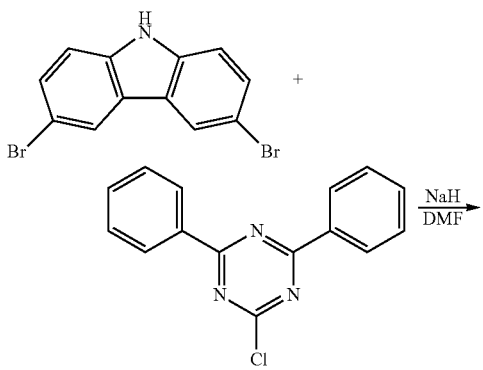

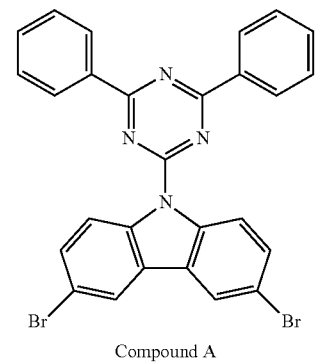

Compound A

Compound A +

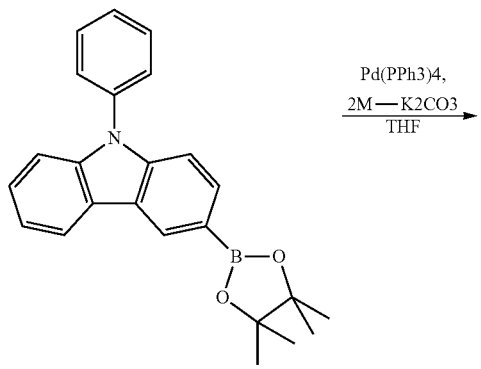

-continued

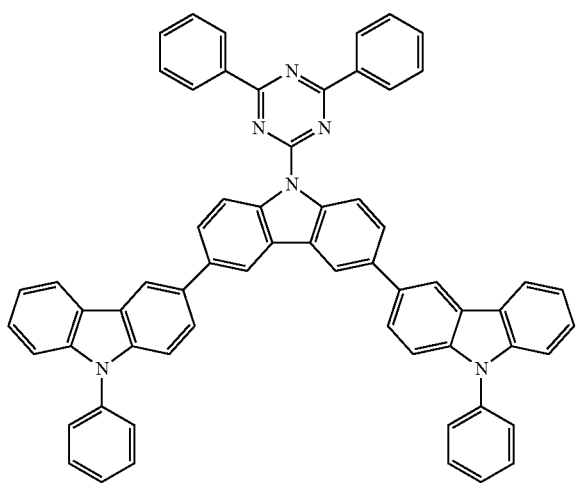

Synthesis Step 1

1.7 g (69.2 mmol) of sodium hydride (NaH) was put in a 500 mL round flask, and 50 mL of dimethylformamide (DMF) was added thereto. 15 g (46.2 mmol) of 3,6-dibromocarbazole dissolved in 100 mL of dimethylformamide was slowly added in a dropwise fashion, and then the resultant was agitated at room temperature for 40 minutes. 13.6 g (50.8 mmol) of 2-chloro-4,6-diphenyl-1,3,5-triazine dissolved in 150 mL of dimethylformamide was slowly added in a dropwise fashion, and then the resultant was agitated for 6 hours. The reactants were poured into water to complete the reaction, and a solid produced therein was filtered. The solid was washed with water and methanol and then heated and dissolved in 200 mL of toluene, and hexane was added thereto for solidification. The obtained solid was dried in a vacuum oven, obtaining 20 g of a compound A (a yield: 80%).

Synthesis Step 2

9 g (16.2 mmol) of the compound A synthesized in the step 1 was mixed with 15 g (40.4 mmol) of N-phenylcarbazol-3-boronic acid pinacol ester and 200 mL of tetrahydrofuran in a 500 mL flask. 100 mL of a 2 M potassium carbonate aqueous solution and 0 0.93 g (0.08 mmol) of tetrakistriphenylphosphine palladium (0) were added and then the resultant was heated and refluxed for 12 hours under a nitrogen gas stream.

An organic layer produced therein was separated and dried with anhydrous sodium sulfate, and an organic solvent therein was distillated and removed under a reduced pressure. The obtained product was purified through silica gel chromatography, obtaining 10 g of a compound represented by Chemical Formula 1b (a yield: 71%).

The compound represented by Chemical Formula 1b was element-analyzed. The results are as follows.

calcd. $C_{63}H_{40}N_6$: C, 85.88; H, 4.58; N, 9.54. found: C, 85.75; H, 4.60; N, 9.61.

Example 2

Synthesis of Compound Represented by Chemical Formula 4a

[Reaction Scheme 2]

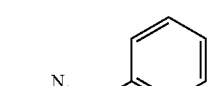

+

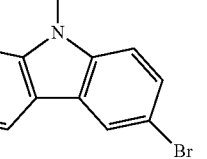

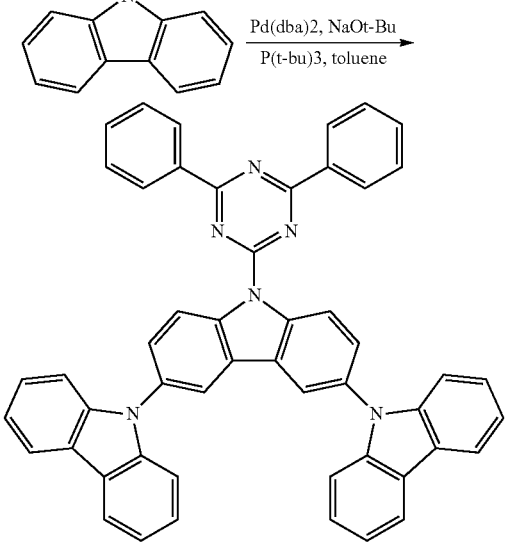

4.7 g (8.46 mmol) of the compound B, 3.53 g (21.15 mmol) of carbazole, and 2.44 g (25.38 mmol) of sodium tert-butoxide were put in a 250 mL round flask, and 120 mL of toluene was added thereto. The mixture was nitrogen-bubbled. 0.49 g (0.85 mmol) of palladium dibenzylideneacetone as a catalyst and 1 g of tri-tert-butylphosphine (50% in toluene) were added followed by heating up to 110° C. When the reaction was complete, a solvent in the mixture was removed, and a remaining product was heated and dissolved in chlorobenzene. The solution was charcoal-treated. After removing a solvent, the remaining product was recrystallized in chlorobenzene and hexane, obtaining 5.2 g of a compound represented by Chemical Formula 4a (a yield: 84%). The compound represented by Chemical Formula 4a was element-analyzed. The result was as follows.

calcd. $C_{51}H_{32}N_6$: C, 84.04; H, 4.43; N, 11.53. found: C, 84.15; H, 4.33; N, 11.65

Example 3

Synthesis of Compound Represented by Chemical Formula 34c

[Reaction Scheme 3]

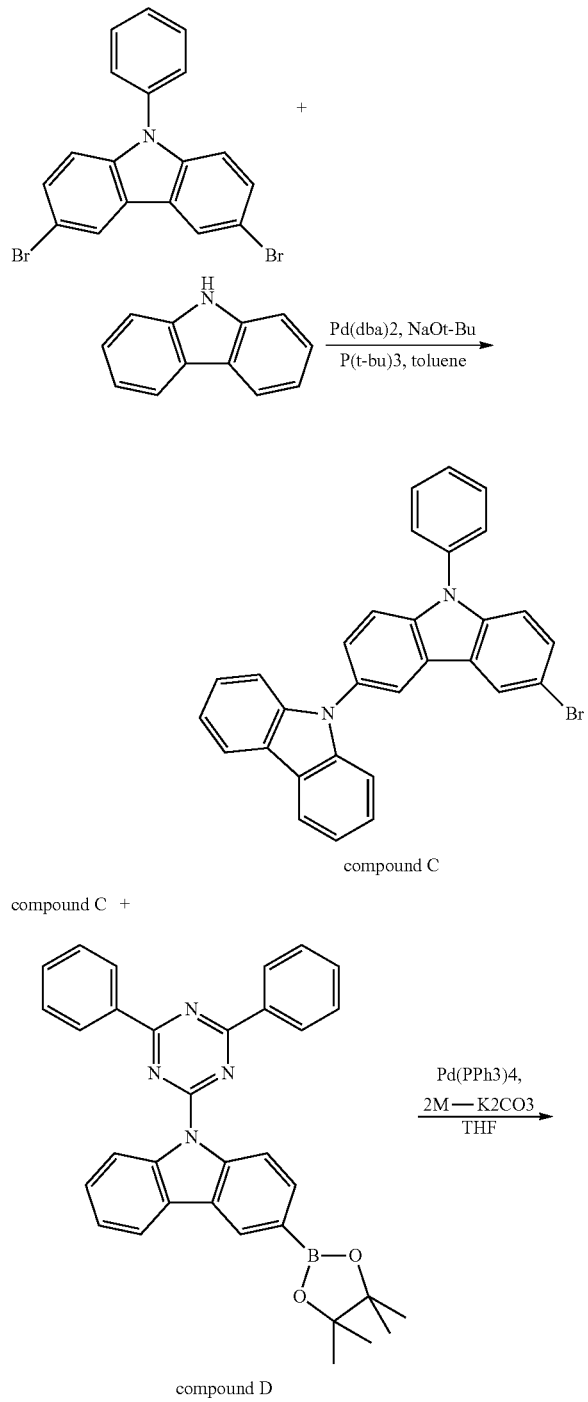

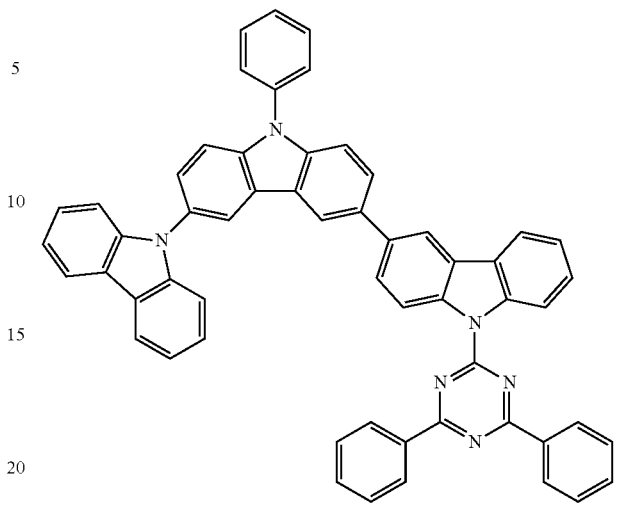

Synthesis Step 1

10 g (25.03 mmol) of 3,6-dibromo-N-phenylcarbazole, 4.6 g (27.53 mmol) of carbazole, and 3.61 g (37.55 mmol) of sodium tert-butoxide were put in a 250 mL round flask, and 150 mL of toluene was added thereto. The mixture was nitrogen-bubbled. Next, 0.43 g (0.75 mmol) of palladium dibenzylidene acetone as a catalyst and 0.8 g of tri-tert-butylphosphine (50% in toluene) were added followed by heating up to 110° C. When the reaction was complete, a solvent therein was removed, and the remaining product was heated and dissolved in chlorobenzene. The solution was charcoal-treated. The charcoal-treated solution was treated through silica gel chromatography, separating 6 g of a compound C (a yield: 50%).

Synthesis Step 2

6 g (12.4 mmol) of the compound C synthesized in the step 1 and 7.82 g (14.91 mmol) of a compound D were mixed with 100 mL of tetrahydrofuran in a 250 mL flask. 50 mL of a 2 M potassium carbonate aqueous solution and 0.72 g (0.62 mmol) of tetrakistriphenyl phosphine palladium (0) were added followed by heating and refluxing for 12 hours under a nitrogen gas stream.

The reactant was cooled down to room temperature, and a solid produced therein was filtered. The solid was washed with water and methanol and then dissolved in chlorobenzene and charcoal-treated. After removing all the solvent therein, the remaining product was recrystallized in chlorobenzene and hexane, obtaining 5.5 g of a compound represented by Chemical Formula 34c (a yield: 55%).

The compound represented by Chemical Formula 34c was element-analyzed. The result is as follows.

calcd. $C_{57}H_{36}N_6$: C, 85.05; H, 4.51; N, 10.44. found: C, 85.55; H, 4.80; N, 10.74.

Example 4

Synthesis of Compound Represented by Chemical Formula 10d

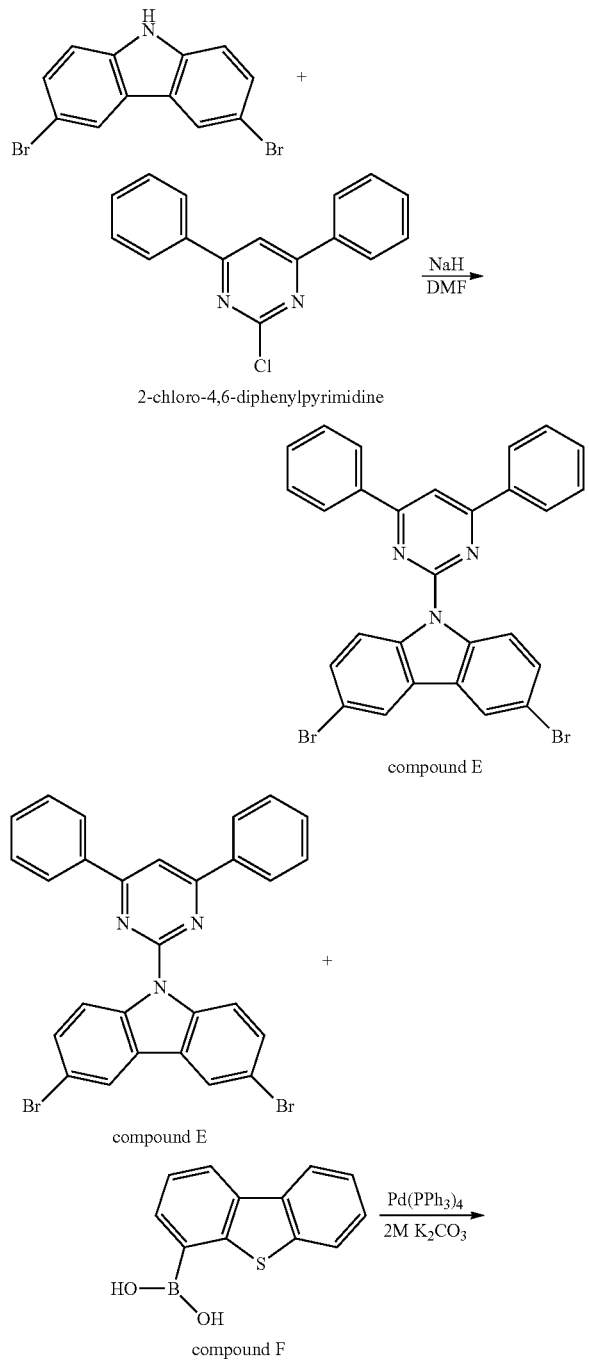

compound F

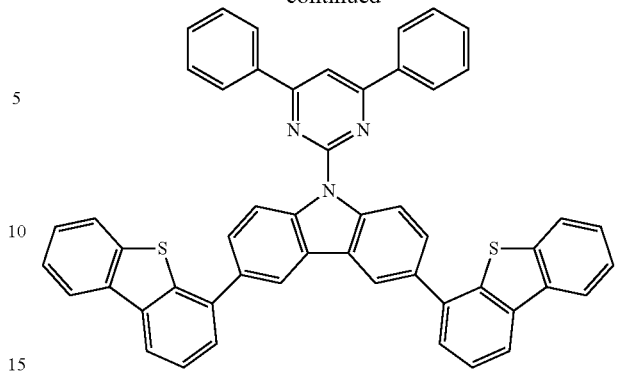

Synthesis Step 1

4.05 g (101.3 mmol) of sodium hydride (NaH) was put in a 1 L round flask, and 100 mL of dimethylformamide (DMF) was added thereto. Next, a solution prepared by dissolving 21.95 g (67.5 mmol) of 3,6-dibromocarbazole in 100 mL of DMF was slowly added in a dropwise fashion and then the resultant was agitated at room temperature for 40 minutes. 21.62 g (81.0 mmol) of 2-chloro-4,6-diphenylpyrimidine was slowly added in a dropwise fashion, and the mixture was agitated for 6 hours. The resulting reactant was poured into water to complete the reaction, and a solid produced therein was filtered. The solid was washed with water and methanol and then heated and dissolve in 400 mL of chlorobenzene, and hexane was added thereto for solidification. The obtained solid was filtered and dried in a vacuum oven, obtaining 34.9 g of a compound E (a yield 93%).

Synthesis Step 2

17.50 g (31.5 mmol) of the compound E synthesized in the step 1, 17.97 g (78.8 mmol) of a compound F, and 3.64 g (3.2 mmol) of tetrakistriphenyl phosphine palladium (0) were put in a 1 L flask, and 200 mL of a 2 M potassium carbonate aqueous solution and 200 mL of tetrahydrofuran and 200 mL of toluene as a solvent were added and the resultant was heated and refluxed for 12 hours under a nitrogen gas stream.

A solid produced was filtered during the reaction. 200 mL of methanol was added to the filtered solution, and a solid additionally produced therein was filtered. The solid and the former solid were washed with 1 L of methanol. The washed solids were heated and dissolved in 100 mL of chlorobenzene, and 200 mL of methanol was added thereto for solidification. Then, the solid was dried in a vacuum oven, obtaining 10 g of a compound represented by Chemical Formula 10d (a yield: 50%).

The compound represented by Chemical Formula 10d was element-analyzed. The result is as follows.

calcd. $C_{52}H_{31}N_3S_2$: C, 81.97; H, 4.10; N, 5.51; S, 8.42. found: C, 82.34; H, 4.61; N, 5.80; S, 8.30

Comparative Example 1

Carbazole Biphenyl (CBP)

A common carbazole biphenyl was used.

Manufacture of Organic Light Emitting Diode

Example 5

Manufacture of Organic Light Emitting Diode Using Compound of Example 1

The compound synthesized in Example 1 was used as a host, and $Ir(PPy)_3$ was used as a dopant to manufacture an organic light emitting diode. 1000 Å-thick ITO was used as an anode, while 1000 Å-thick aluminum (Al) was used as a cathode.

For example, a method of manufacturing the organic light emitting diode included cutting an ITO glass substrate having sheet resistance of 15 Ω/cm² into a size of 50 mm×50 mm×0.7 mm and ultrasonic wave-cleaning it in acetone, isopropylalcohol, and pure water for 15 minutes respectively and then, UV-ozone cleaning it for 30 minutes.

On the substrate, a 800 Å-thick hole transport layer (HTL) was formed by depositing N,N'-di(1-naphthyl)-N,N'-diphenylbenzidine (NPB) (70 nm) and 4,4',4''-tri(N-carbazolyl)triphenylamine (TCTA) (10 nm) under conditions of a vacuum degree of 650×10⁻⁷ Pa and a deposition rate of 0.1 to 0.3 nm/s.

Then, a 300 Å-thick emission layer was formed thereon using the compound according to Example 1 under the same vacuum deposit conditions, and Ir(PPy)₃ as a phosphorescent dopant was simultaneously deposited. Then, a 300 Å-thick emission layer was formed thereon using the compound according to Example 2 under the same vacuum deposit conditions, and Ir(PPy)₃ as a phosphorescent dopant was simultaneously deposited.

On the emission layer, bis(8-hydroxy-2-methylquinolinolato)-aluminumbiphenoxide (BAlq) was deposit to form a 50 Å-thick hole blocking layer under the same vacuum deposit conditions.

Subsequently, a 200 Å-thick electron transport layer (ETL) was formed thereon by depositing Alq₃ under the same vacuum deposit conditions.

On the electron transport layer (ETL), LiF and Al were sequentially deposited to form a cathode, manufacturing an organic light emitting diode.

The organic photoelectric device had a structure of ITO/NPB (70 nm)/TCTA (10 nm)/EML (the compound of Example 1 (93 wt %)+Ir(PPy)₃ (7 wt %), 30 nm)/Balq (5 nm)/Alq₃ (20 nm)/LiF (1 nm)/Al (100 nm).

Example 6

Manufacture of Organic Light Emitting Diode Using Compound of Example 2

An organic light emitting diode was manufactured according to the same method as Example 4 except that the compound synthesized in Example 2 was used instead of the compound synthesized in Example 1.

Example 7

Manufacture of Organic Light Emitting Diode Using Compound of Example 3

An organic light emitting diode was manufactured according to the same method as Example 4 except that the compound synthesized in Example 3 was used instead of the compound synthesized in Example 1.

Comparative Example 2

Manufacture of Organic Light Emitting Diode Using Compound of Comparative Example 3

An organic light emitting diode was manufactured according to the same method as Example 4 except that the compound synthesized in Comparative Example 1 was used instead of the compound synthesized in Example 1.

Performance Measurement of Organic Light Emitting Diode

EXPERIMENTAL EXAMPLE

Each organic light emitting diode according to Example 5 and Comparative Example 1 was measured regarding current density and luminance changes depending on voltage and luminous efficiency. The measurements were specifically performed in the following method. The results are provided in the following Table 1.

(1) Measurement of Current Density Change Depending on Voltage Change

The manufactured organic light emitting diodes were measured for current value flowing in the unit device while increasing the voltage from 0 V to 10 V using a current-voltage meter (Keithley 2400), and the measured current value was divided by area to provide the result.

(2) Measurement of Luminance Change Depending on Voltage Change

The manufactured organic light emitting diodes were measured for luminance while increasing the voltage form 0V to 10V using a luminance meter (Minolta Cs-1000A).

(3) Measurement of Luminous Efficiency

Current efficiency (cd/A) and electric power efficiency (lm/W) at the same luminance (1000 cd/m²) were calculated by using luminance and current density from the item (1) and (2) and voltage.

(4) Color coordinate was measured using a luminance meter (Minolta Cs1000A), and the results are shown.

TABLE 1

| | Results at 9000 cd/m² | | | | |
|---|---|---|---|---|---|
| | Driving voltage (V) | Luminous efficiency (cd/A) | Electric power efficiency (lm/W) | Color coordinate (x, y) | Time lapsed until 10% luminous efficiency decreases |
| Example 5 | 4.7 | 50.6 | 33.6 | 0.345, 0.622 | 20 h |
| Comparative Example 2 | 7.7 | 26 | 10.6 | 0.328, 0.63 | 1 h |

The organic light emitting diode according to Example 4 using the compound for an organic optoelectronic device of Example 1 shows about twice improved luminous efficiency and three times electric power efficiency than that of Comparative Example 2. In addition, a driving voltage may be lowered by 3 V or more.

In terms of life-span, a time lapsed until 10% luminous efficiency decreases shows about 20 times difference. Thus, the compound of the Example 1 may improve luminous efficiency and life-span of an organic light emitting diode remarkably.

By way of summation and review, an organic light emitting diode may convert electrical energy into light by applying current to an organic light emitting material. It may have a structure in which a functional organic material layer is interposed between an anode and a cathode. The organic material layer may include a multi-layer including different materials, for example a hole injection layer (HIL), a hole transport layer (HTL), an emission layer, an electron transport layer (ETL), and an electron injection layer (EIL), in order to improve efficiency and stability of an organic light emitting diode.

In such an organic light emitting diode, when a voltage is applied between an anode and a cathode, holes from the anode and electrons from the cathode are injected to an organic material layer and recombined to generate excitons having high energy. The generated excitons generate light having certain wavelengths while shifting to a ground state.

A phosphorescent light emitting material may be used for a light emitting material of an organic light emitting diode in addition to the fluorescent light emitting material. Such a phosphorescent material emits lights by transporting the electrons from a ground state to an exited state, non-radiance transiting of a singlet exciton to a triplet exciton through intersystem crossing, and transiting a triplet exciton to a ground state to emit light.

As described above, in an organic light emitting diode, an organic material layer includes a light emitting material and a charge transport material, for example a hole injection material, a hole transport material, an electron transport material, an electron injection material, and the like.

The light emitting material may classified as blue, green, and red light emitting materials according to emitted colors, and yellow and orange light emitting materials to emit colors approaching natural colors.

When one material is used as a light emitting material, a maximum light emitting wavelength may shifted to a long wavelength or color purity may decrease because of interactions between molecules, or device efficiency may decrease because of a light emitting quenching effect. Therefore, a host/dopant system may be included as a light emitting material in order to improve color purity and increase luminous efficiency and stability through energy transfer.

In order to implement excellent performance of an organic light emitting diode, a material constituting an organic material layer, for example a hole injection material, a hole transport material, a light emitting material, an electron transport material, an electron injection material, and a light emitting material such as a host and/or a dopant, should be stable and have good efficiency. However, development of an organic material layer forming material for an organic light emitting diode has thus far not been satisfactory and thus there is a need for a novel material. This material development is also required for other organic optoelectronic devices.

A low molecular weight organic light emitting diode may be manufactured as a thin film in a vacuum deposition method, and may have good efficiency and life-span performance. A polymer organic light emitting diode manufactured in an inkjet or spin coating method has an advantage of low initial cost and being suitable for large sizes.

Both low molecular weight organic light emitting and polymer organic light emitting diodes have an advantage of self-light emitting, high speed response, wide viewing angle, ultra-thinness, high image quality, durability, large driving temperature range, and the like. In particular, they have good visibility due to the self-light emitting characteristic compared with a conventional LCD (liquid crystal display) and have an advantage of decreasing thickness and weight of an LCD by up to a third, because they do not need a backlight.

In addition, since they have a response speed of a microsecond unit, which may 1000 times faster than an LCD, they may realize a perfect motion picture without an after-image. Based on these advantages, they have been remarkably developed to have 80 times the efficiency and more than 100 times the life-span since they first came out in the late 1980s. Recently, they have become rapidly larger such that a 40-inch organic light emitting diode panel is now possible.

They should simultaneously have improved luminous efficiency and life-span in order to be larger. Herein, their luminous efficiency is enhanced by smooth combination between holes and electrons in an emission layer. However, since an organic material in general may have slower electron mobility than hole mobility, it may provide less efficient combination between holes and electrons. Accordingly, increasing electron injection and mobility from a cathode and simultaneously preventing movement of holes is desired.

As described above, embodiments may provide a compound for an organic optoelectronic device that may act as a light emitting or electron injection and transport material, and also act as a light emitting host along with an appropriate dopant.

Embodiments may provide an organic optoelectronic device having excellent life-span, efficiency, driving voltage, electrochemical stability, and thermal stability.

Embodiments may provide an organic optoelectronic device having excellent electrochemical and thermal stability and life-span characteristics, and high luminous efficiency at a low driving voltage.

<Description of symbols of drawings>

| | |
|---|---|
| 100: organic light emitting diode | 110: cathode |
| 120: anode | 105: organic thin layer |
| 130: emission layer | 140: hole transport layer (HTL) |
| 150: electron transport layer (ETL) | 160: electron injection layer (EIL) |
| 170: hole injection layer (HIL) | |
| 230: emission layer + electron transport layer (ETL) | |

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope as set forth in the following claims.

What is claimed is:

1. A compound for an organic optoelectronic device, the compound being represented by the following Chemical Formula 1:

[Chemical Formula 1]

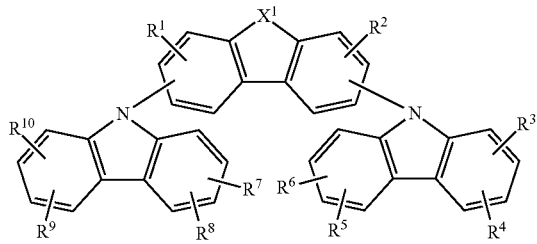

wherein, in the above Chemical Formula 1,
X¹ is —NR'—,
the R' is hydrogen; deuterium; a substituted or unsubstituted C1 to C20 alkyl group; a substituted or unsubstituted C6 to C30 aryl group; or a substituted or unsubstituted C2 to C30 heteroaryl group;
$R^1$ to $R^{10}$ are the same or different and are independently hydrogen; deuterium; a substituted or unsubstituted C1 to C20 alkyl group; a substituted or unsubstituted C6 to C30 aryl group; or a substituted or unsubstituted C2 to C30 heteroaryl group; and
at least one of the $R^1$ to $R^{10}$ or R' is a substituted or unsubstituted C6 to C30 aryl group having electron characteristics; or a substituted or unsubstituted C2 to C30 heteroaryl group having electron characteristics.

2. The compound for an organic optoelectronic device as claimed in claim 1, wherein the compound includes the substituted or unsubstituted C6 to C30 aryl group having electron characteristics, and the substituted or unsubstituted C6 to C30 aryl group having electron characteristics is a substituted or unsubstituted triperylenyl group, a substituted or unsubstituted fluorenyl group, a substituted or unsubstituted spirofluorenyl group, a substituted or unsubstituted terphenyl group, a substituted or unsubstituted pyrenyl group, a substituted or unsubstituted perylenyl group, a substituted or unsubstituted phenanthrenyl group, or a combination thereof.

3. The compound for an organic optoelectronic device as claimed in claim 1, wherein the compound includes the substituted or unsubstituted C2 to C30 heteroaryl group having electron characteristics, and the substituted or unsubstituted C2 to C30 heteroaryl group having electron characteristics is a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof.

4. The compound for an organic optoelectronic device as claimed in claim 1, wherein the R' is a substituted or unsubstituted C6 to C30 aryl group having electron characteristics; or a substituted or unsubstituted C2 to C30 heteroaryl group having electron characteristics.

5. A compound for an organic optoelectronic device, wherein the compound is at least one selected from the group of Chemical Formulae 1a to 33a

[Chemical Formula 1a]

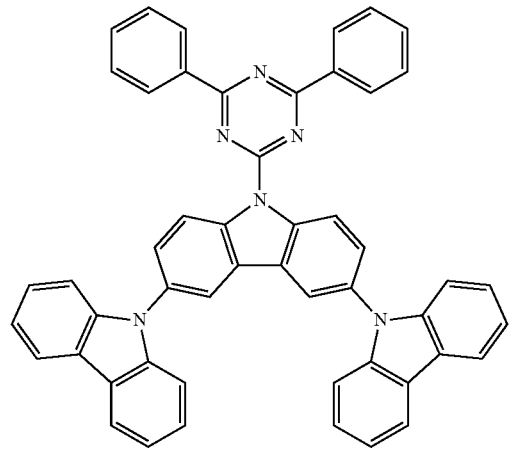

[Chemical Formula 2a]

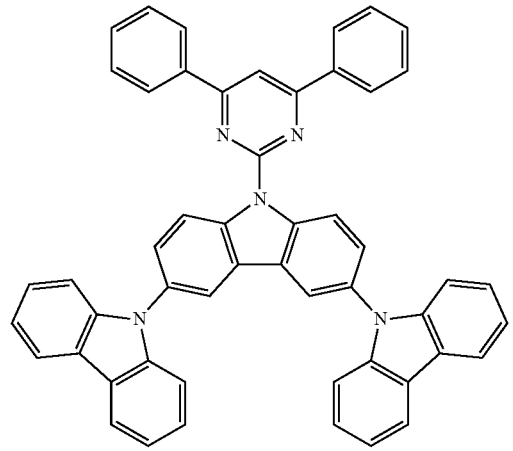

[Chemical Formula 3a]

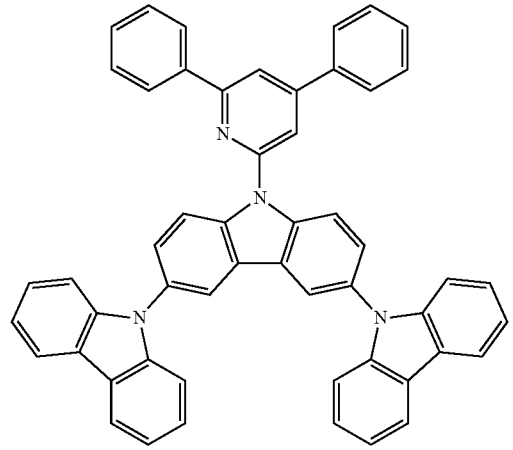

-continued
[Chemical Formula 4a]
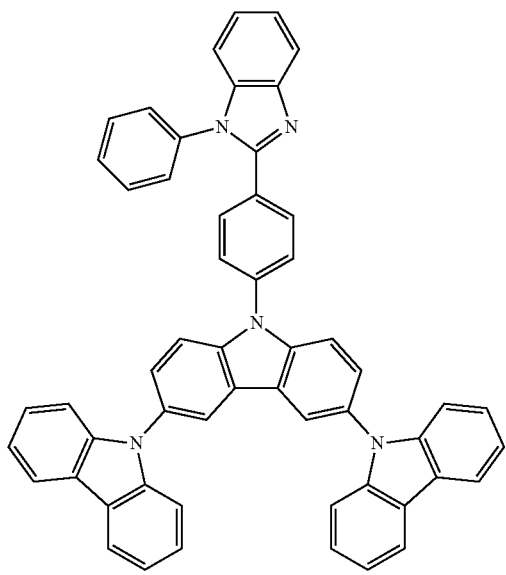
[Chemical Formula 5a]
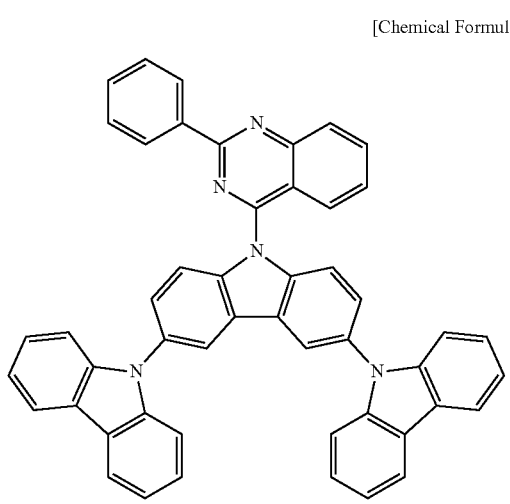
[Chemical Formula 6a]
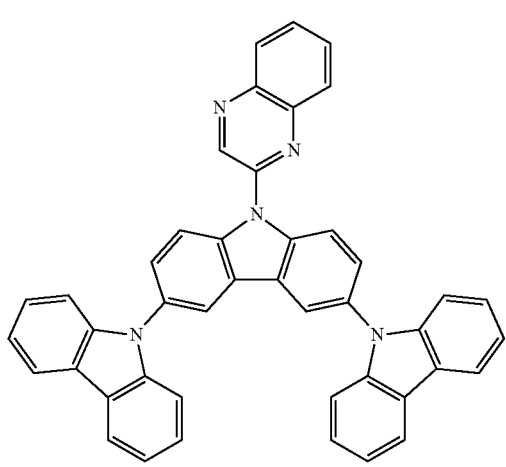
-continued
[Chemical Formula 7a]
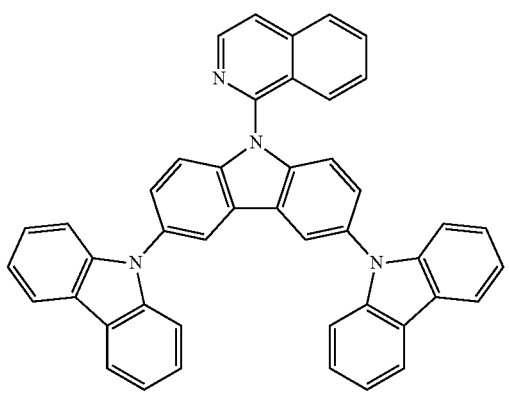
[Chemical Formula 8a]
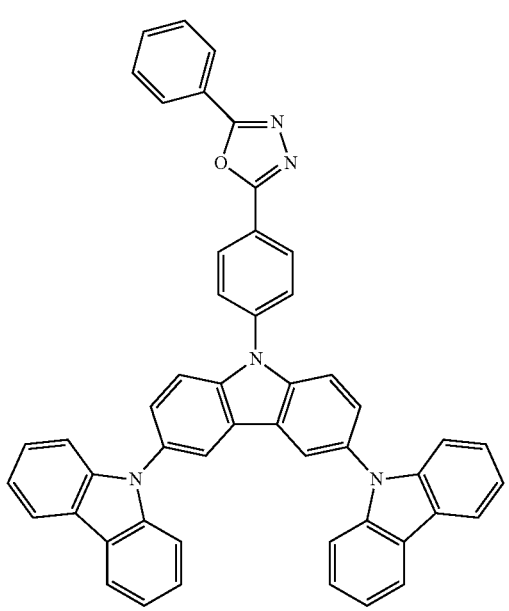
[Chemical Formula 9a]
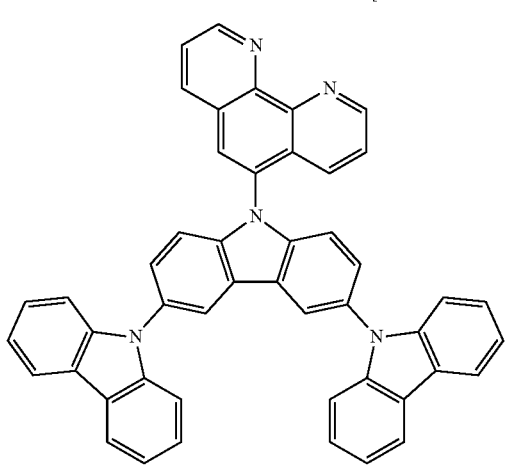

[Chemical Formula 10a]
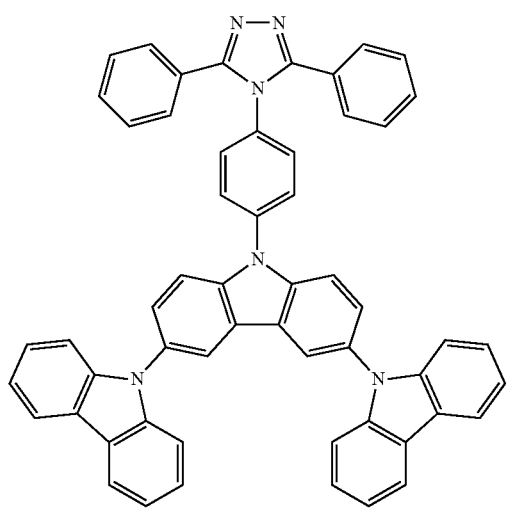
[Chemical Formula 11a]
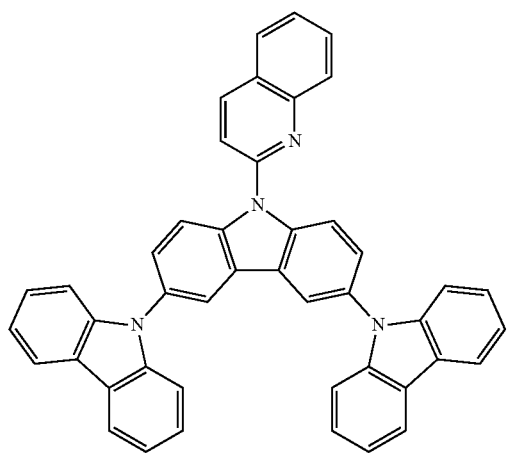
[Chemical Formula 12a]
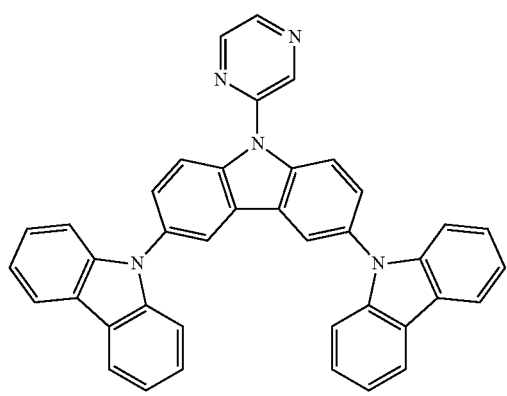
[Chemical Formula 13a]
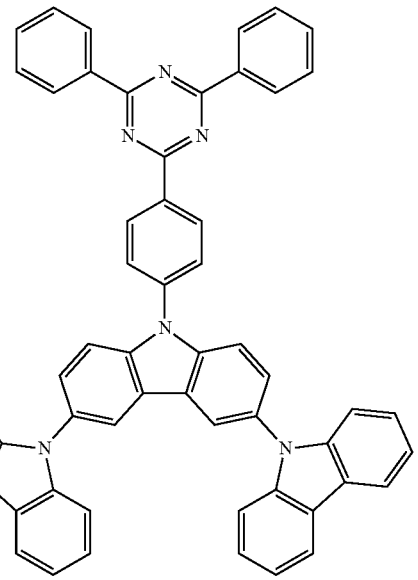
[Chemical Formula 14a]
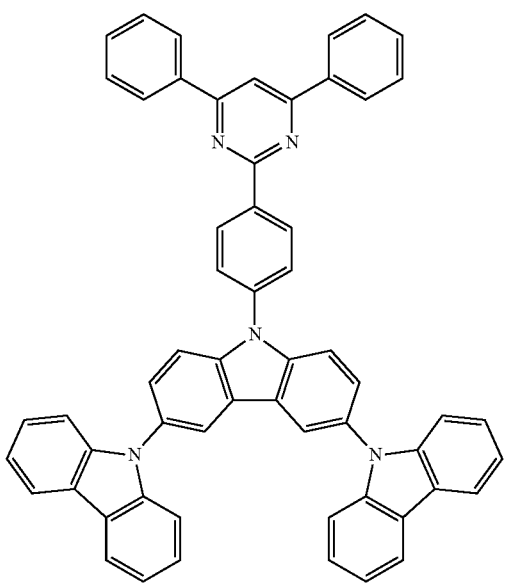

[Chemical Formula 15a]
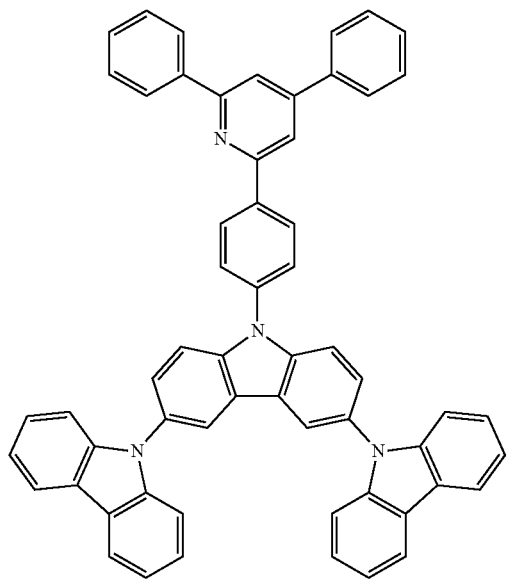
[Chemical Formula 16a]
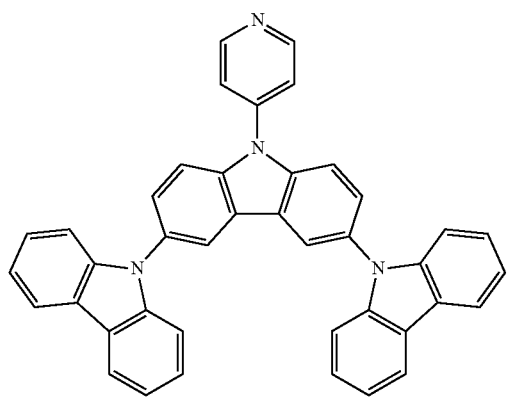
[Chemical Formula 17a]
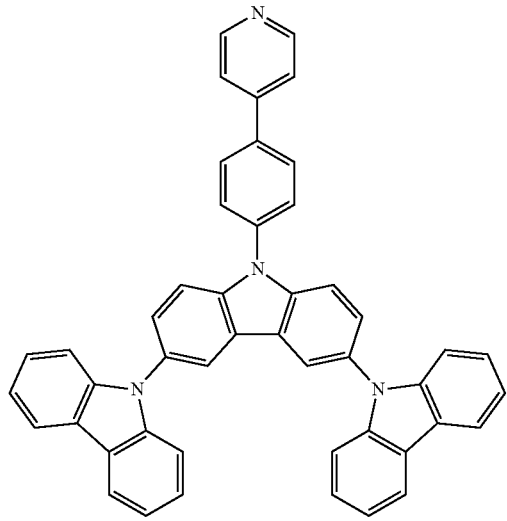
[Chemical Formula 18a]
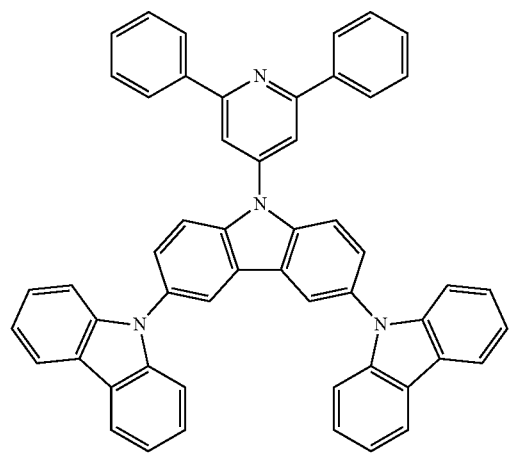
[Chemical Formula 19a]
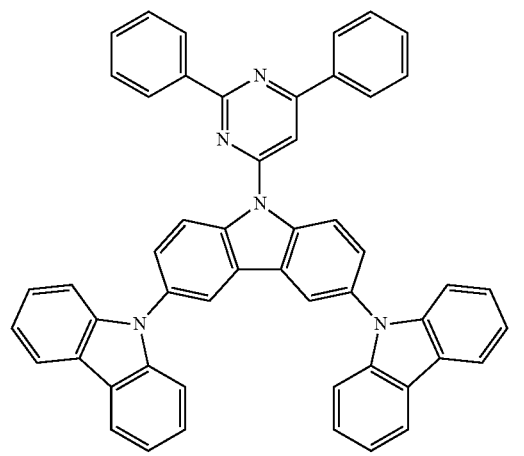
[Chemical Formula 20a]
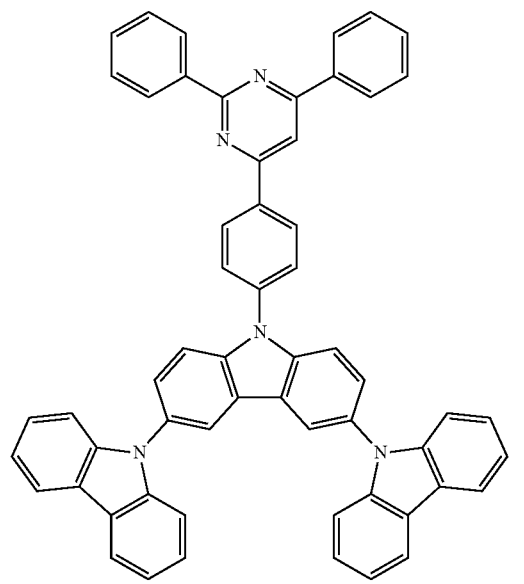

[Chemical Formula 21a]
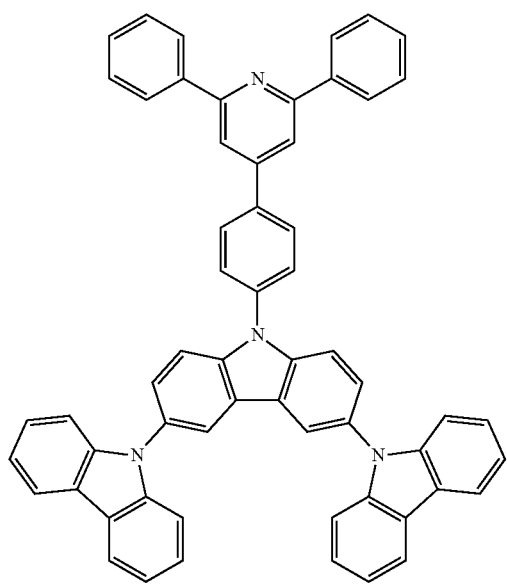
[Chemical Formula 22a]
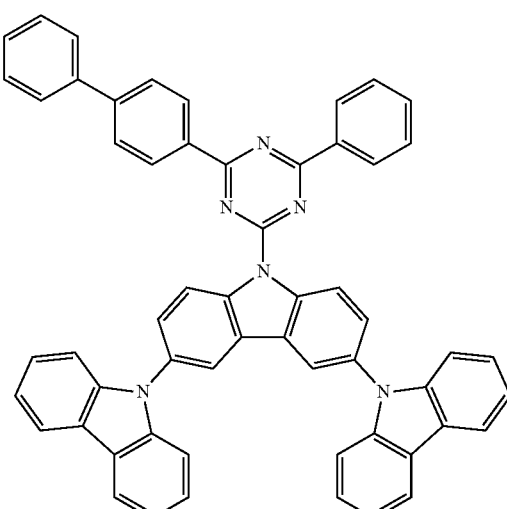
[Chemical Formula 23a]
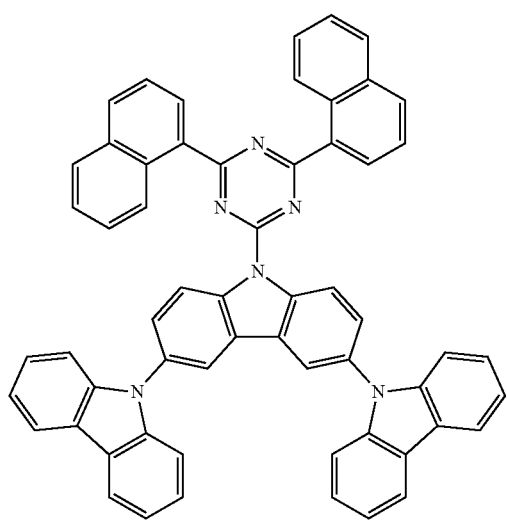
[Chemical Formula 24a]
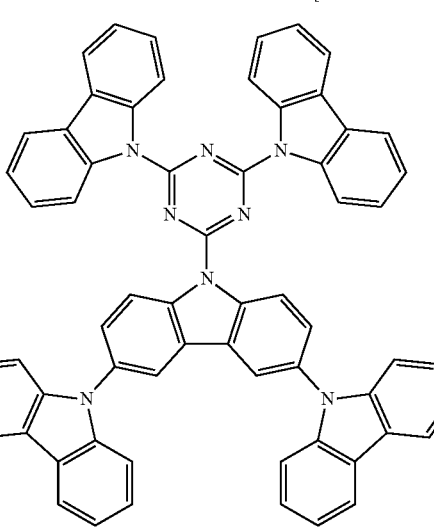
[Chemical Formula 25a]
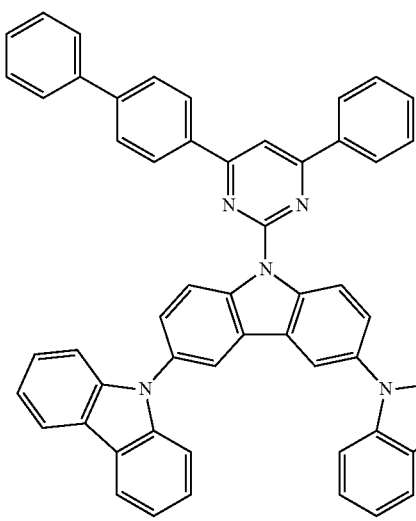
[Chemical Formula 26a]
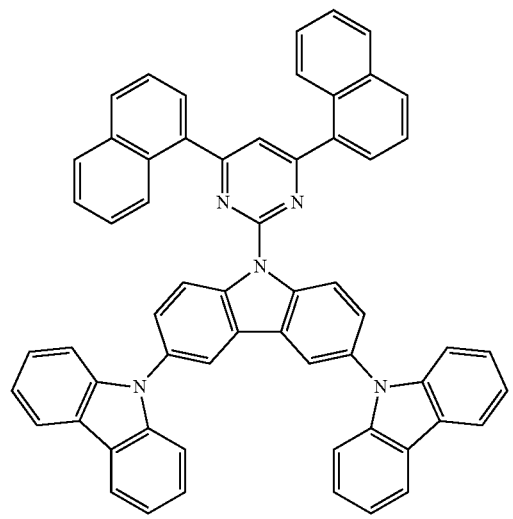

[Chemical Formula 27a]
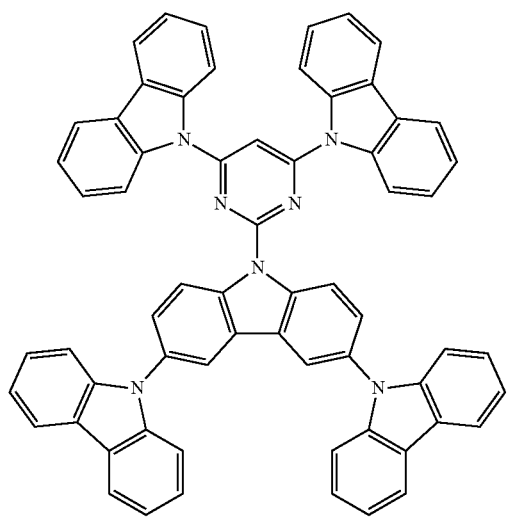
[Chemical Formula 28a]
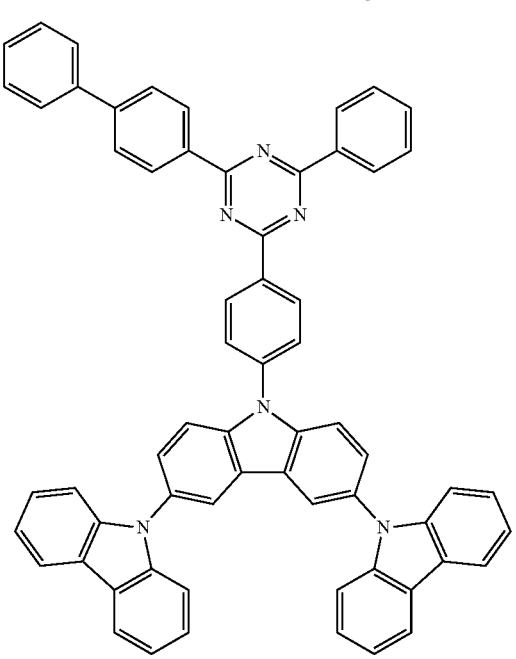
[Chemical Formula 29a]
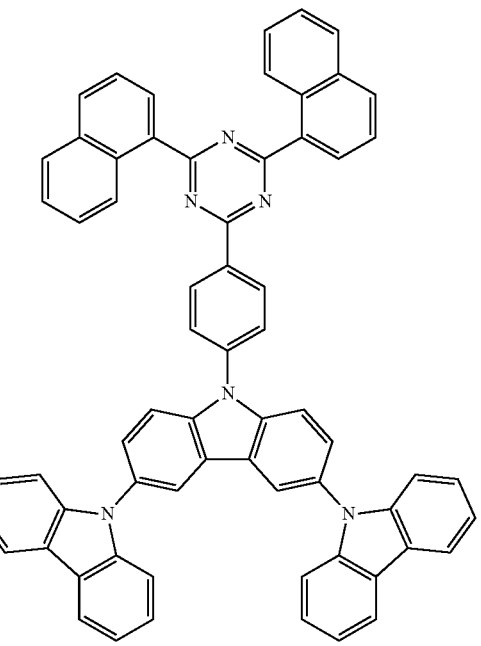
[Chemical Formula 30a]
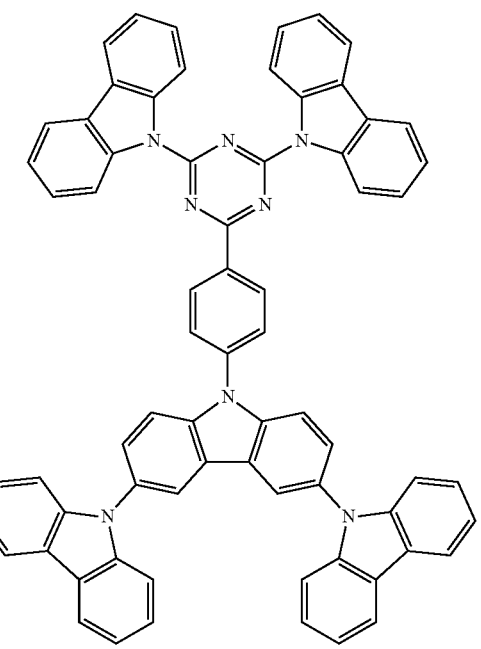

[Chemical Formula 31a]

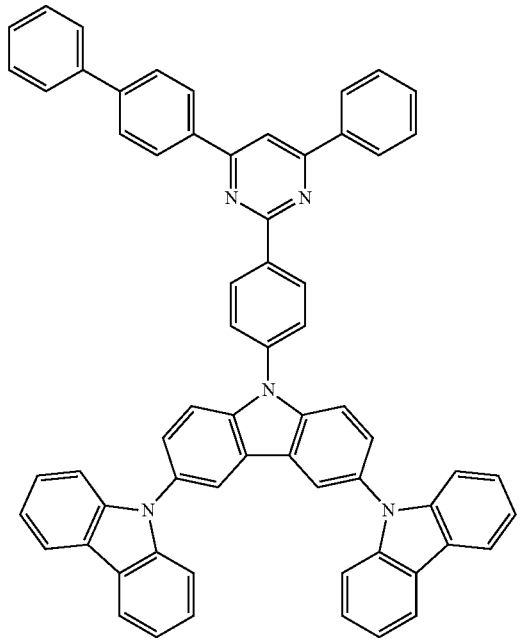

[Chemical Formula 32a]

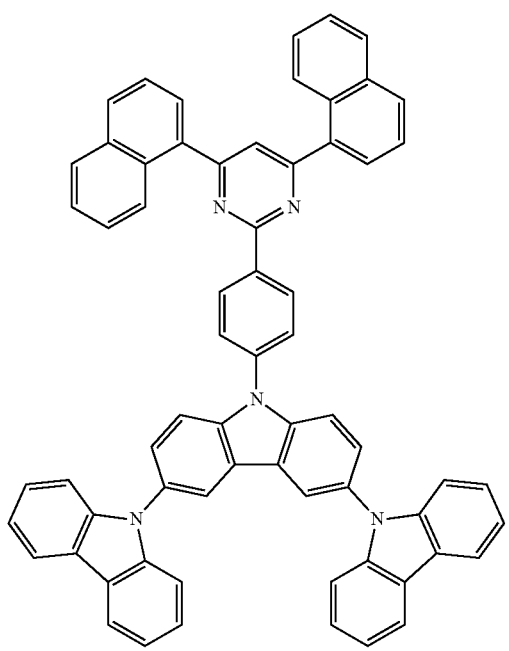

[Chemical Formula 33a]

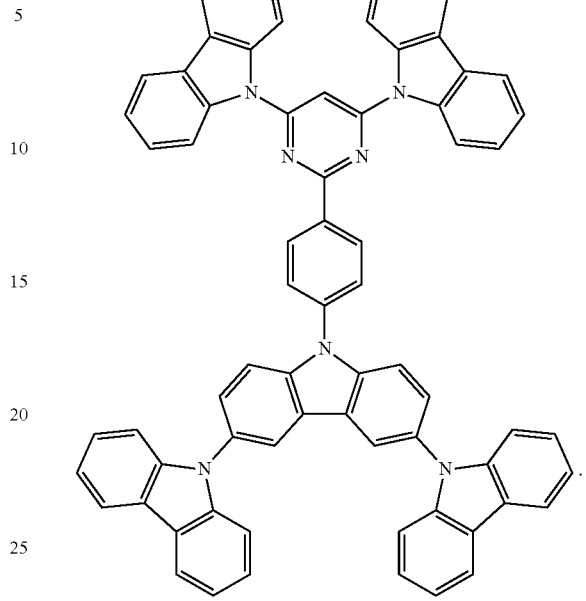

6. An organic light emitting diode, comprising
an organic light emitting diode including an anode, a cathode, and at least one organic thin layer between the anode and the cathode,
wherein the at least one organic thin layer includes the compound for an organic optoelectronic device according to claim 1.

7. The organic light emitting diode as claimed in claim 6, wherein the at least one organic thin layer includes an emission layer, a hole transport layer (HTL), a hole injection layer (HIL), an electron transport layer (ETL), an electron injection layer (EIL), a hole blocking layer, or a combination thereof.

8. The organic light emitting diode as claimed in claim 7, wherein the at least one organic thin layer includes the emission layer, and the compound for an organic optoelectronic device is included in the emission layer.

9. A display device comprising the organic light emitting diode as claimed in claim 6.

10. An organic light emitting diode, comprising
an organic light emitting diode including an anode, a cathode, and at least one organic thin layer between the anode and the cathode,
wherein the at least one organic thin layer includes the compound for an organic optoelectronic device according to claim 5.

11. The organic light emitting diode as claimed in claim 10, wherein the at least one organic thin layer includes an emission layer, a hole transport layer (HTL), a hole injection layer (HIL), an electron transport layer (ETL), an electron injection layer (EIL), a hole blocking layer, or a combination thereof.

12. The organic light emitting diode as claimed in claim 11, wherein the at least one organic thin layer includes the emission layer, and the compound for an organic optoelectronic device is included in the emission layer.

13. A display device comprising the organic light emitting diode as claimed in claim 10.

14. A compound for an organic optoelectronic device, the compound being represented by the following Chemical Formula 1:

[Chemical Formula 1]

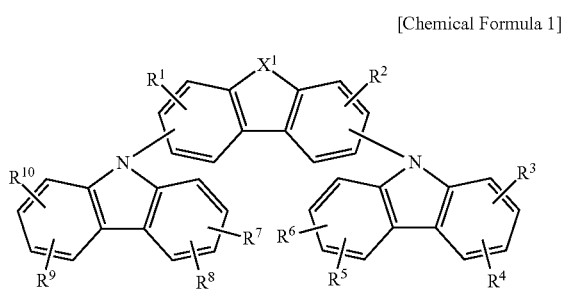

wherein, in the above Chemical Formula 1,

X$^1$ is —NR'—, —O—, —Se—, —PR'— or —S—, the R' is hydrogen; deuterium; a substituted or unsubstituted C1 to C20 alkyl group; a substituted or unsubstituted C6 to C30 aryl group; or a substituted or unsubstituted C2 to C30 heteroaryl group;

R$^1$ to R$^{10}$ are the same or different and are independently hydrogen; deuterium; a substituted or unsubstituted C1 to C20 alkyl group; a substituted or unsubstituted C6 to C30 aryl group; or a substituted or unsubstituted C2 to C30 heteroaryl group; and at least one of the R$^1$ to R$^{10}$ or R' is a substituted or unsubstituted triperylenyl group, a substituted or unsubstituted fluorenyl group, a substituted or unsubstituted spirofluorenyl group, a substituted or unsubstituted terphenyl group, a substituted or unsubstituted pyrenyl group, a substituted or unsubstituted perylenyl group, a substituted or unsubstituted phenanthrenyl group, a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof.

15. An organic light emitting diode, comprising:

an organic light emitting diode including an anode, a cathode, and at least one organic thin layer between the anode and the cathode, wherein the at least one organic thin layer includes the compound for an organic optoelectronic device according to claim 14.

16. The organic light emitting diode as claimed in claim 15, wherein the at least one organic thin layer includes an emission layer, a hole transport layer (HTL), a hole injection layer (HIL), an electron transport layer (ETL), an electron injection layer (EIL), a hole blocking layer, or a combination thereof.

17. The organic light emitting diode as claimed in claim 16, wherein the at least one organic thin layer includes the emission layer, and the compound for an organic optoelectronic device is included in the emission layer.

18. A display device comprising the organic light emitting diode as claimed in claim 15.

* * * * *